United States Patent
Kirby et al.

(10) Patent No.: US 10,338,038 B2
(45) Date of Patent: Jul. 2, 2019

(54) ESTABLISHING FLUIDIC CONNECTIONS BETWEEN CHROMATOGRAPHY COMPONENTS

(71) Applicant: Waters Technologies Corporation, Milford, MA (US)

(72) Inventors: Peter Kirby, Derry, NH (US); Marcos O. Peroza, Methuen, MA (US); Steven D. Trudeau, Webster, MA (US); Ryan Hill, Durham, NC (US); Raymond P. Fisk, Norton, MA (US); Jonathan Belanger, Whitinsville, MA (US); Wade P. Leveille, Douglas, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 951 days.

(21) Appl. No.: 14/367,245

(22) PCT Filed: Dec. 10, 2012

(86) PCT No.: PCT/US2012/068712
§ 371 (c)(1),
(2) Date: Jun. 20, 2014

(87) PCT Pub. No.: WO2013/095964
PCT Pub. Date: Jun. 27, 2013

(65) Prior Publication Data
US 2015/0323509 A1    Nov. 12, 2015

Related U.S. Application Data

(60) Provisional application No. 61/578,257, filed on Dec. 21, 2011.

(51) Int. Cl.
*G01N 30/60* (2006.01)
*F16L 19/00* (2006.01)
(Continued)

(52) U.S. Cl.
CPC ......... *G01N 30/6026* (2013.01); *B01D 15/10* (2013.01); *F16L 19/00* (2013.01);
(Continued)

(58) Field of Classification Search
None
See application file for complete search history.

(56) References Cited

U.S. PATENT DOCUMENTS 6,074,556 A * 6/2000 Van Davelaar ........ B01D 15/08
                                                    210/198.2
6,294,088 B1    9/2001 Allington et al.
(Continued)

FOREIGN PATENT DOCUMENTS

GB        2379487 A      3/2003
WO     2011/020803 A1    2/2011
(Continued)

OTHER PUBLICATIONS

Extended European Search Report for Application No. 12859833.1, dated Apr. 25, 2016 (8 pages).
(Continued)

*Primary Examiner* — Kara M Peo
(74) *Attorney, Agent, or Firm* — Schmeiser, Olsen & Watts LLP

(57) ABSTRACT

A clamp assembly includes a rail configured to receive a first fluidic assembly, and a carriage slidably mounted to the rail and configured to receive a second fluidic assembly. The carriage is operable to establish a first fluid tight seal between the first fluidic assembly and a chromatography column received within the clamp assembly, and to establish a second fluid tight seal between the second fluidic assembly and the chromatography column.

24 Claims, 52 Drawing Sheets

(51) Int. Cl.
 B01D 15/10 (2006.01)
 G01N 30/02 (2006.01)
 G01N 30/30 (2006.01)

(52) U.S. Cl.
 CPC ............ *G01N 30/02* (2013.01); *G01N 30/30* (2013.01); *G01N 30/6039* (2013.01); *G01N 30/6047* (2013.01); *G01N 2030/3061* (2013.01); *Y10T 29/53917* (2015.01); *Y10T 29/53952* (2015.01)

(56) References Cited

U.S. PATENT DOCUMENTS

| | | |
|---|---|---|
| 7,101,477 B1 | 9/2006 | Willis et al. |
| 2006/0008390 A1 | 1/2006 | Prentice et al. |
| 2007/0084982 A1 | 4/2007 | Marlene et al. |
| 2007/0158942 A1 | 7/2007 | Keene |
| 2010/0154207 A1 | 6/2010 | Ford et al. |
| 2011/0259827 A1 | 10/2011 | Belanger et al. |

FOREIGN PATENT DOCUMENTS

| | | |
|---|---|---|
| WO | 2011/085341 A1 | 7/2011 |
| WO | 2011/085359 A1 | 7/2011 |
| WO | 2012/058513 A1 | 5/2012 |

OTHER PUBLICATIONS

International Search Report and Written Opinion for Application No. PCT/US12/68712, dated Feb. 22, 2013 (6 pages).
Extended European Search Report for Application No. 17178189.1, dated Jan. 18, 2018 (8 pages).

\* cited by examiner

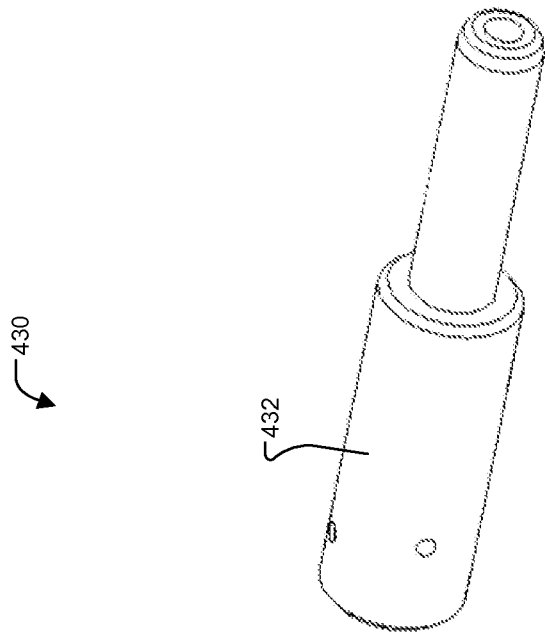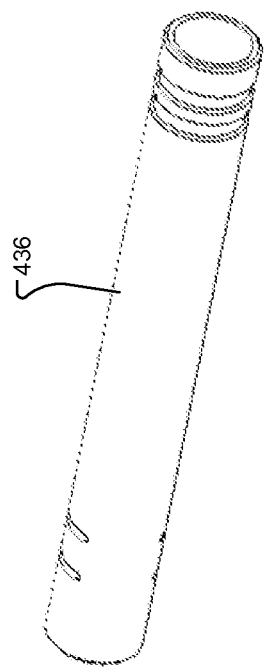
FIG. 12

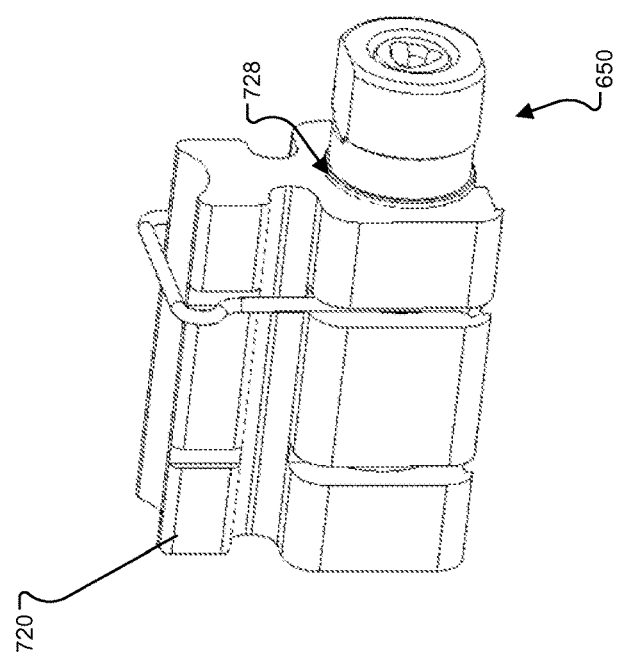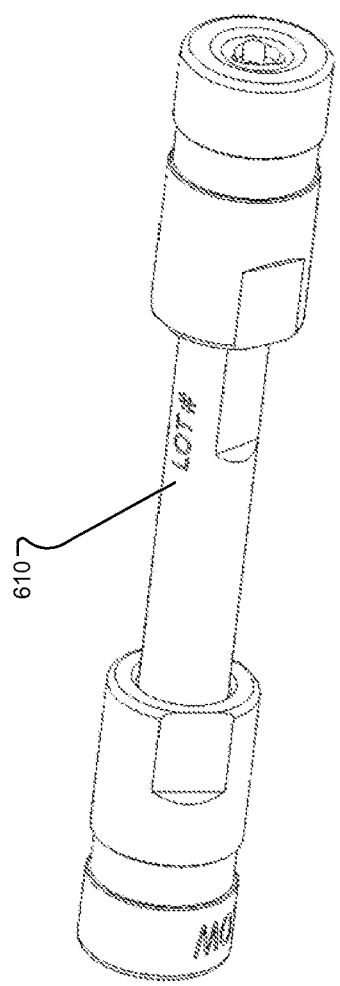
FIG. 29L

ESTABLISHING FLUIDIC CONNECTIONS BETWEEN CHROMATOGRAPHY COMPONENTS

RELATED APPLICATIONS

This application is the National Stage of International Application No. PCT/US2012/068712, filed on Dec. 10, 2012, which claims priority to and benefit of U.S. Provisional Patent Application No. 61/578,257, entitled "Establishing Fluidic Connections between Chromatography Components," filed Dec. 21, 2011. The contents and teachings of each of these applications are hereby expressly incorporated herein by reference in their entirety.

TECHNICAL FIELD

This disclosure relates to establishing fluidic connections between chromatography components.

BACKGROUND

Chromatography is a set of techniques for separating a mixture into its constituents. Generally, in a liquid chromatography analysis, a pump system takes in and delivers a mixture of liquid solvents (and/or other fluids) to a sample manager, where a sample awaits injection into the solvents. The sample is the material under analysis. Examples of samples include complex mixtures of proteins, protein precursors, protein fragments, reaction products, and other compounds, to list but a few. In an isocratic chromatography application, the composition of the liquid solvents remains unchanged, whereas in a gradient chromatography application, the solvent composition varies over time. The mobile phase, comprised of a sample dissolved in a mixture of solvents (and/or other fluids), moves to a point of use, such as a column, which includes a packing material referred to as the stationary phase.

By passing the mobile phase through the column, the various components in the sample separate from each other at different rates and thus elute from the column at different times. A detector receives the separated components from the column and produces an output from which the identity and quantity of the analytes may be determined. Temperature can influence the results of the analysis, affecting such properties as the separation performance of the column and the viscosity of a mobile phase. Therefore, maintaining an accurate constant column temperature can be important to the accuracy and reproducibility of the results.

Systems used for performing chromatography analysis often include fluidic tubing for providing fluid communication between system components. For example, chromatography systems typically include components, such as pumps, valves, columns, and detectors, that are connected together through fluidic (e.g., metallic or polymeric) tubing. The system components and the fluidic tubing are often connected using threaded fittings or bayonet fittings. Connection and disconnection of these fittings (e.g., during assembly, repair, and/or replacement) can require application of torque, e.g., by hand alone or with the use of tools, to establish a fluid tight connection. This can be time consuming, cumbersome (e.g., in cases in which multiple turns are required), and may lead to leaks and/or failure if the fittings are not threaded together properly and/or if adequate torque is not applied when the connection is made.

In modern chromatography, systems pressures are being increased and internal fluid volumes are being reduced. As a result, the reliability and seal characteristics of conventional fittings are becoming problematic. As the pressure is raised and the system internal fluid volume is reduced the fitting dead volume and sensitivity to the assemblers skill become impediments to chromatographic quality. In this regard, establishing fluid tight connections with such conventional fittings can require the use of skilled labor since it is often the case that a high degree of precision is required to ensure the connection is not only fluid tight, but is also devoid of undesirable dead volume which can lead to lost precision in the measured data.

SUMMARY

This disclosure arises, in part, from the realization that apparatus can be provided for connecting chromatography components (e.g., columns, guards, filters, tubes, etc.) without the use of hand tools (e.g., wrenches) or ferrules in such a way as to inhibit (e.g., prevent) carry-over, dispersion, or dead volume. In some cases, a fluid tight connection (e.g., up to at least 20,000 pounds per square inch) is provided which does not require the application of torque, such as is typical of conventional fluid fittings having threaded or bayonet connections, and/or which can allow for a quick and highly repeatable connection that does not require highly skilled operators to ensure that the connection is properly established.

One aspect features a clamp assembly that includes a rail configured to receive a first fluidic assembly, and a carriage slidably mounted to the rail and configured to receive a second fluidic assembly. The carriage is operable to establish a first fluid tight seal between the first fluidic assembly and a chromatography column received within the clamp assembly, and to establish a second fluid tight seal between the second fluidic assembly and the chromatography column.

Another aspect provides an apparatus that includes a first fluidic assembly, a second fluidic assembly, and a clamp assembly. The clamp assembly includes a rail configured to receive the first fluidic assembly, and a carriage slidably mounted to the rail and configured to receive the second fluidic assembly. The carriage is operable to establish a first fluid tight seal between the first fluidic assembly and a chromatography column received within the clamp assembly, and to establish a second fluid tight seal between the second fluidic assembly and the chromatography column.

Another aspect features a thermal module for pre-heating liquid flowing into a liquid chromatography column. The thermal module includes an apparatus and a trough compartment. The apparatus includes a first fluidic assembly, a second fluidic assembly, and a clamp assembly. The clamp assembly includes a rail configured to receive the first fluidic assembly, and a carriage slidably mounted to the rail and configured to receive the second fluidic assembly. The carriage is operable to establish a first fluid tight seal between the first fluidic assembly and a chromatography column received within the clamp assembly, and to establish a second fluid tight seal between the second fluidic assembly and the chromatography column. The trough compartment has two ends. One of the two ends of the trough compartment has an electrical socket. The clamp assembly is disposed within the trough compartment, and the first fluidic assembly is plugged into the electrical socket at the one end of the trough compartment.

According to another aspect, a column assembly includes a chromatography column including a compliant seal defining a fluid passage configured to seal against a tapered fluid conduit without the use of a ferrule or a threaded compression screw.

Another aspect provides an apparatus for establishing fluid communication between a chromatography column and a guard cartridge or a filter cartridge. The apparatus defines a cavity for receiving a guard cartridge or a filter cartridge, and comprising a compliant seal. The compliant seal defines a fluid passage configured to seal against a tapered fluid conduit without the use of a ferrule or a threaded compression screw.

A further aspect features a method that includes inserting a column assembly into a clamp assembly; moving a carriage of the clamp assembly into contact with the column assembly; actuating a lever on the carriage and thereby establishing a first fluid tight seal between a first fluidic assembly and a first end of the column assembly; and a second fluid tight seal between a second fluidic assembly and a second end of the column assembly.

Another aspect provides a fluidic assembly for establishing a fluidic connection with a chromatography column. The fluidic assembly includes a tubing sub-assembly that includes a needle defining a fluid passage, and an outlet capillary tube in fluid communication with the fluid passage of the needle. The fluidic assembly also includes an inner barrel sub-assembly configured to receive the tubing sub-assembly, and an outer barrel sub-assembly configured to receive the inner barrel sub-assembly.

Implementations can provide one or more of the following advantages.

These configurations can help to ensure repeatability of connection. Such configurations can also help to ensure ease of connection, and helps to provide a fluid connection which does not require highly skilled operators to ensure that the connection is properly established. In addition, less mechanical force may be required to establish the fluid connections as compared to conventional threaded fittings or bayonet fittings which require application of torque, e.g., by hand alone or with the use of tools, to establish a fluid tight connection.

Other aspects, features, and advantages are in the description, drawings, and claims.

BRIEF DESCRIPTION OF THE DRAWINGS

FIG. 12 is an isometric view of an inner barrel sub-assembly from the barrel assembly of FIG. 10.

Like reference numbers indicate like elements.

DETAILED DESCRIPTION

Systems described herein include apparatus for connecting fluidic tubing to a chromatography column to establish a fluid tight connection therebetween. The apparatus can provide a quick and highly repeatable fluid tight connection that does not require highly skilled operators to ensure that the connection is properly established. The apparatus allows for chromatography components, such as columns, guards, filters, tubing, etc., to be connected without the use of tools or ferrules and in such a way as to inhibit carry-over, dispersion, and dead volume. Various implementations of these systems relate to liquid-chromatography apparatus, for example, HPLC (High Performance Liquid Chromatography) and UPLC (Ultra Performance Liquid Chromatography) systems.

Figure 1:
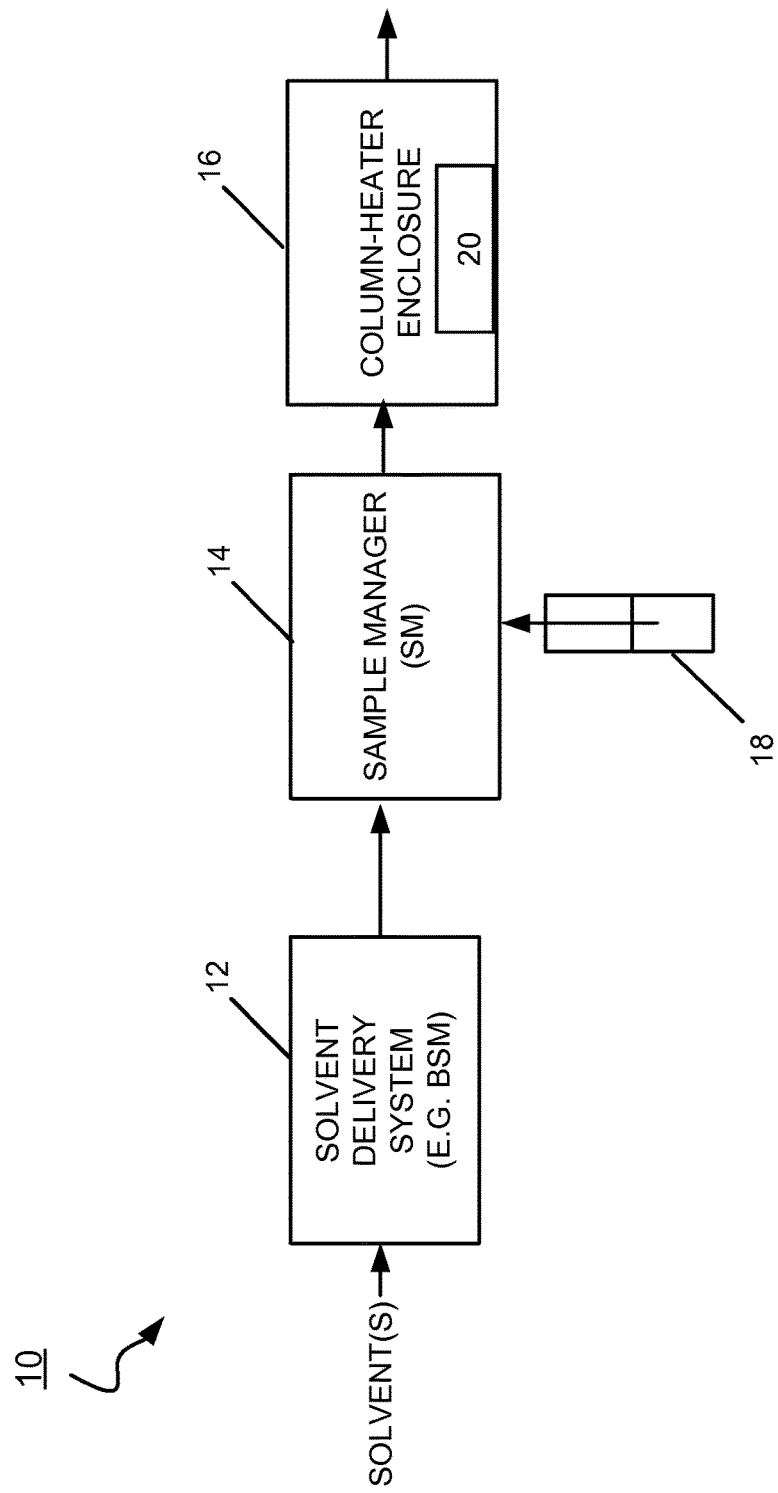
FIG. 1 is a functional block diagram of an implementation of a liquid chromatography system including a column-heater enclosure having a thermal module with an active pre-heater assembly.

FIG. 1 shows an implementation of a liquid chromatography system 10 for separating a sample into its constituents. The liquid chromatography system 10 includes a solvent delivery system 12 in fluidic communication with a sample manager 14. Generally, the solvent delivery system 12 includes pumps (not shown) in fluidic communication with solvent reservoirs from which the pumps draw solvents. The solvent delivery system 12 delivers a mixture of solvents to the sample manager 14. The sample manager 14 is in fluidic communication with a sample source 18 from which the sample manager acquires and introduces a sample to the solvent mixture arriving from the solvent delivery system 12.

In fluidic communication with the sample manager 14 is a column-heater enclosure 16 for receiving therefrom the solvent composition containing the sample. The column-heater enclosure 16 includes a thermal module 20 for providing a controlled temperature environment for a liquid chromatography column used in separating sample-solvent compositions. As described herein, the thermal module 20 includes a fluidic coupling apparatus for establishing fluidic connections between chromatography components (e.g., between fluidic tubing and the chromatography column). From the column-heater enclosure 16, the constituents of the separated sample pass to a detector or other equipment, for example, a mass spectrometer, for analyzing the separation. In one implementation, the liquid chromatography system 10 is a modified ACQUITY UPLC System the ACQUITY UPLC system available from Waters Corporation of Milford Mass.

Figure 2:
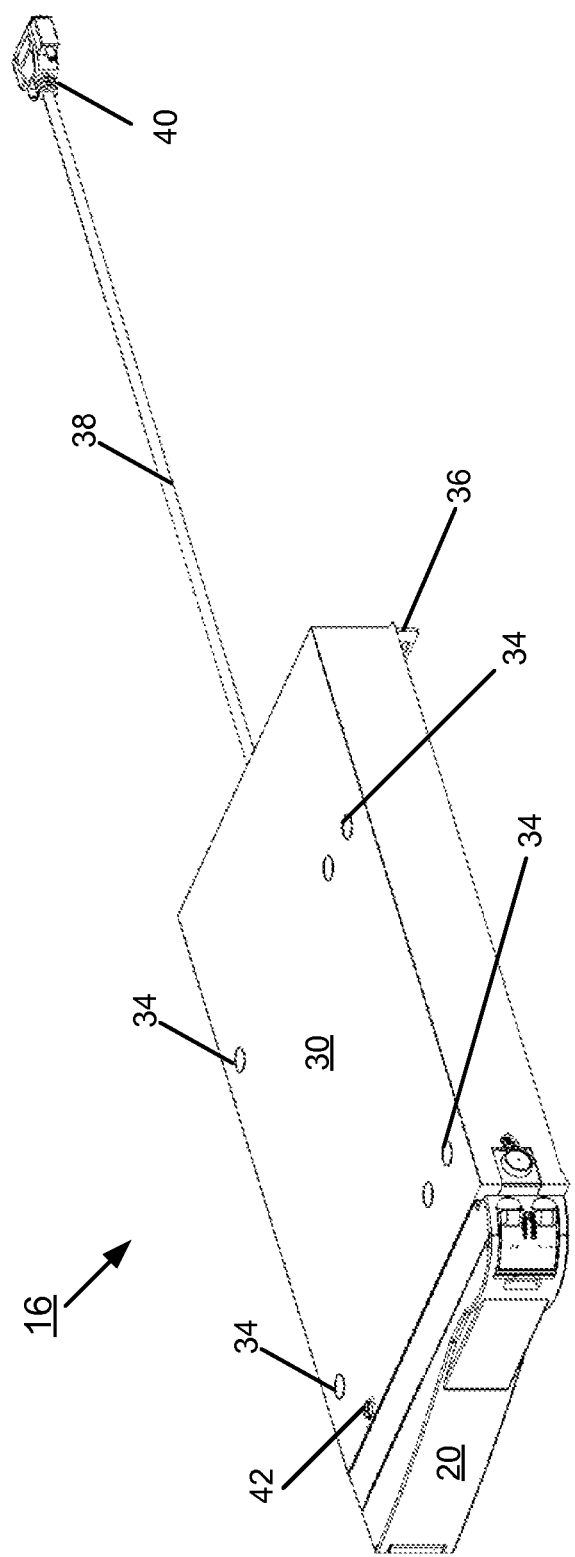
FIG. 2 is an isometric view of an implementation of the column-heater enclosure with the thermal module.

FIG. 2 shows an implementation of the column-heater enclosure 16 including the thermal module 20, which is attached to a front side of a main housing 30. In one implementation, the housing 30 is 21.1 inches in length, 13.5 inches in width, and 3.5 inches in height.

Typically, the pieces of equipment, namely the solvent delivery system 12, solvent manager 14, and column-heater enclosure 16, can be vertically stacked. Such an arrangement can help shorten the length of the plumbing between the pieces of equipment. Other pieces, for example, mass spectrometers, because of their size, are often placed to one side of or in front of an equipment stack.

A role of the main housing 30 is to provide support for another piece of equipment, such as a detector, placed on top of the column-heater enclosure 16. The top surface of the housing 30 has dimples 34, for receiving the feet of the enclosure situated above. The dimples 34 align with structural columns within the housing 30 that support the borne weight. The column-heater enclosure 16, itself, can sit physically atop another piece of equipment, such as the sample manager 14. A flange 36 with openings for mechanical fasteners extends orthogonally from the base of the housing 30 and is for mounting the column-heater enclosure 16 securely to the sample manager 14 situated below. An electrical cord 38 and connector 40 electrically connect the column-heater enclosure 16 to the sample manager 14, from which the column-heater enclosure 16 receives DC power and communications for running the thermal module 20.

Another role of the housing 30 is to provide a fluid leakage path between the equipment sitting atop the column-heater enclosure 16 and the equipment sitting below. For this role, the top surface of the housing 30 has a drainage inlet 42, which connects to a drainage outlet of the upper equipment. An internal fluidic conduit (not shown) runs from the drainage inlet 42 to an outlet (not shown) in the bottom of the housing 30; and this outlet connects to an inlet of the lower equipment.

Figure 3:
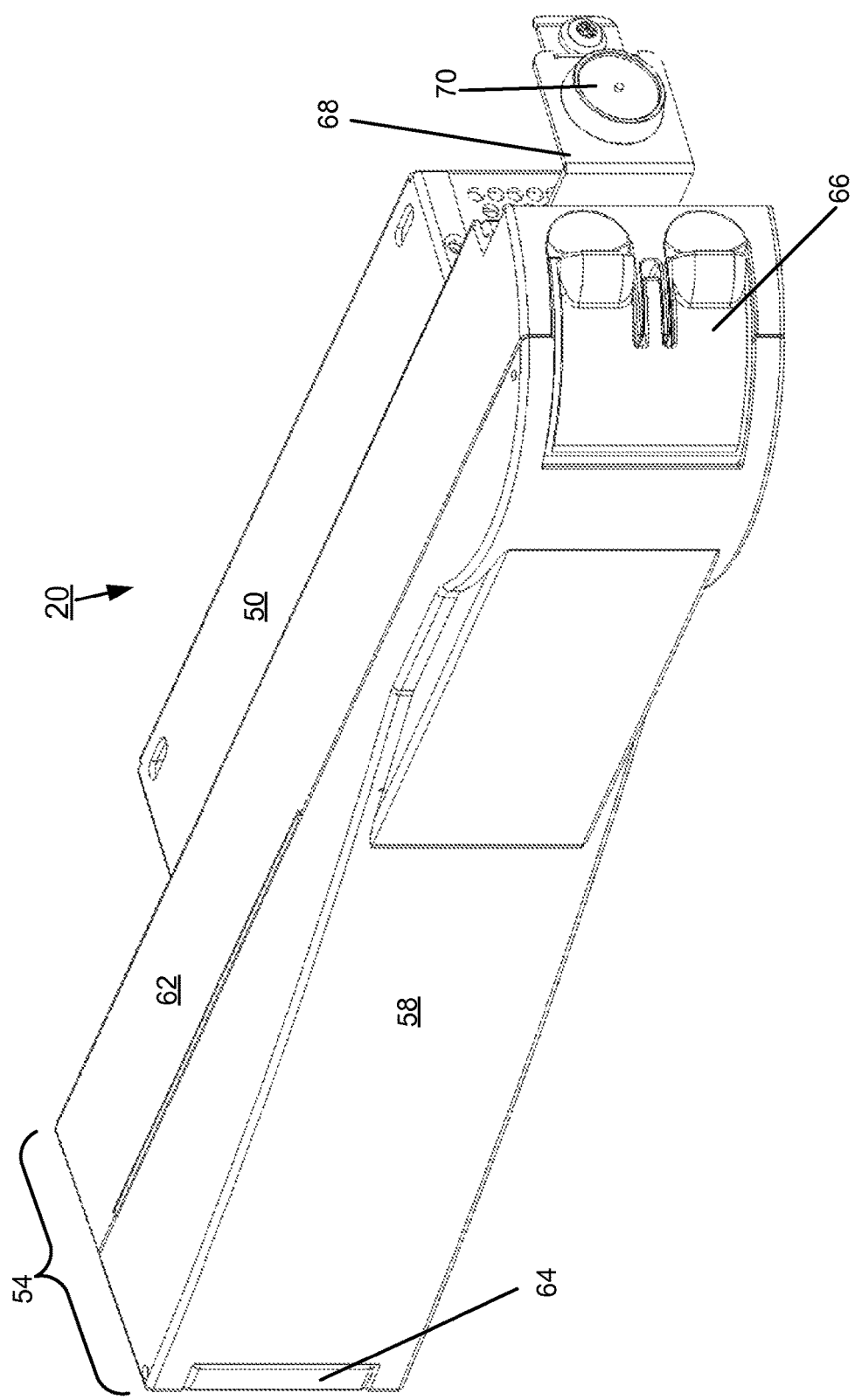
FIG. 3 is an isometric view of the thermal module.

FIG. 3 shows an implementation of the thermal module 20 including an electronics housing 50 coupled to a column housing 54. The column housing 54 comprises a front door 58 coupled at one end to a column holder 62 by a hinge 64 and, at its opposite end, secured in a closed position to the column holder 62 by a (preferably mechanical) latch 66. A bracket 68 extends from one side of the electronics housing 50. The bracket 68 and electronics housing 50 can be made from a single piece of sheet metal. An electrical device 70 is mounted on a surface of the bracket 68. The device 70 is in electrical communication with electronics within the electronics housing 50 and is used to read identification information from some types of chromatography columns.

Figure 4:
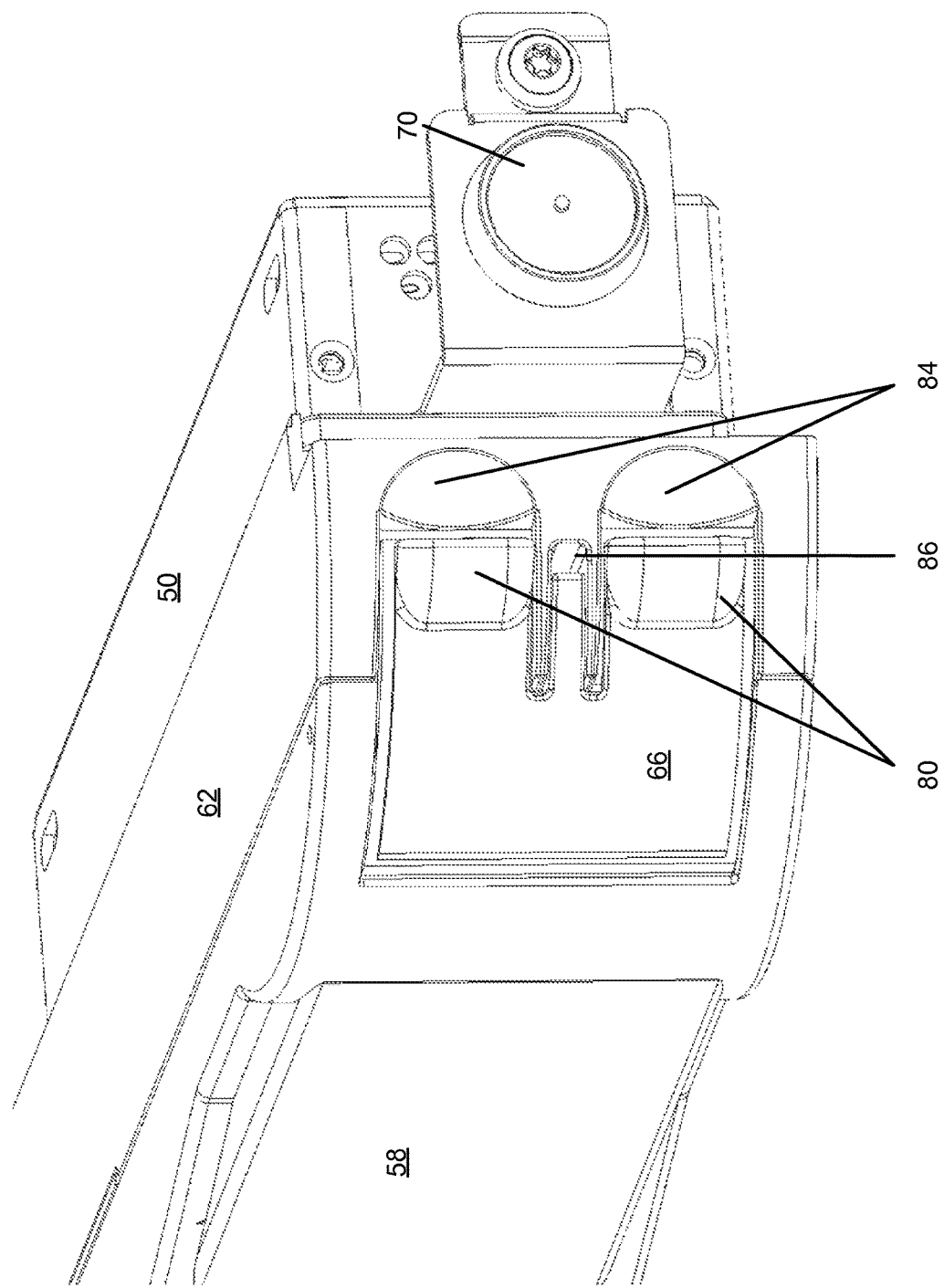
FIG. 4 is an end view of the thermal module with its door latched closed.

FIG. 4 shows an end view of the thermal module 20 with the latch 66. The latch 66 includes a pair of raised bumps 80. A curved side of each raised bump 80 extends from the surface of the latch; a planar side of each raised bump 80 provides an edge by which a human fingertip may pull upon the latch 66 in order to detach the door 58 from the column holder 62. A pair of recesses 84 at the latch end of the column holder 62 accommodates the fingertips that pull upon the raised bumps 80. With the door 58 in a closed position, a small gap 86 provides a passage for tubing into the column holder 62.

Figure 5:
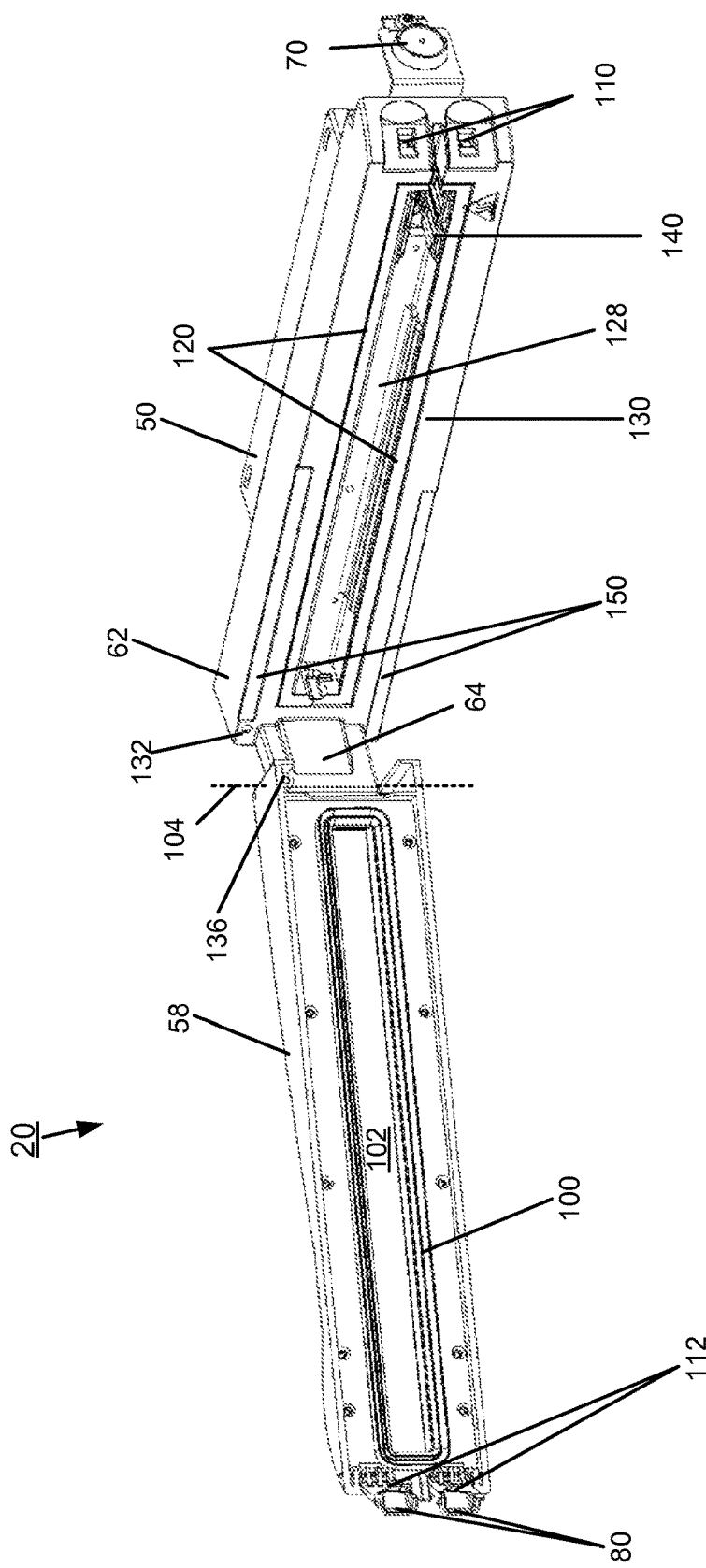
FIG. 5 is an isometric view of the thermal module with its door open.

FIG. 5 shows an isometric view of the thermal module 20 with its front door 58 open to reveal an interior side of the door 58 and the interior of the column holder 62. The interior side of the front door 58 has a generally rectangular rubber gasket 100 disposed near the door's edges. A layer of insulation covers the door interior, and a plastic panel 102 can be placed over the insulation. The door 58 is attached at one end to the hinge 64 for pivoting about axis 104 between an open and closed position. The hinge 64 extends generally orthogonally from a front face 130 of the column holder 62 at one end thereof (opposite the latch end). At the opposite (latch) end of the column 5 holder 62 are a pair of holes 110 for receiving corresponding latch elements 112 on the door 58. These latch elements 112 are interior-side extensions from the raised bumps 80 (FIG. 4) of the door latch 66 which are unlatched from the holes 110 when pulled upon by a person's fingertips.

The interior of the column holder 62 has an open-faced trough compartment 120, within which is a slidable trough 128. The trough 128 has a back surface and two opposing side surfaces. (The door 58, when closed, provides a fourth side for enclosing the trough compartment 120, the gasket 100 on the door interior pressing against and providing a tight thermal seal around the trough compartment 120.) This trough 128 can be slid to either end of the trough compartment 120, as deemed appropriate when configuring the thermal module 20 for use. Here, the slidable trough 128 is shown positioned at the end of the trough compartment 120 near the hinge 64. At the other end of the trough compartment 120 is a receptacle 140 for receiving an active pre-heater assembly, as describe in more detail below.

The front face 130 of the column holder 62 has a magnetic switch 132 located at the hinge end of the thermal module 20. The magnetic switch 132 detects when a connection is broken between the switch 132 and an opposing magnet 136 on the door 58 (i.e., when the door opens). The thermal module 20 uses signals from the magnetic switch 132 to determine whether to maintain or disconnect power to an active pre-heater assembly installed within the column holder 62.

Also near the hinge end of the thermal module, the front face 130 has two rubber gasket strips 150 at the top and bottom edges of the column holder 62. The regions of the front face 130 where the gaskets 150 reside are slightly indented so that the surface of each gasket 150 is on substantially the same plane as the rest of the front face 130 of the column holder 62; that is, when closed, the door 58 presses flush against the gaskets 150 and the front face 130, with little, if any, deformation of the gaskets 150. The resilient, pliable nature of the gaskets 150 avoids pinching tubing that enters or exits, by way of either the top edge or bottom edge, at the hinge end of the thermal module 20.

Figure 6:
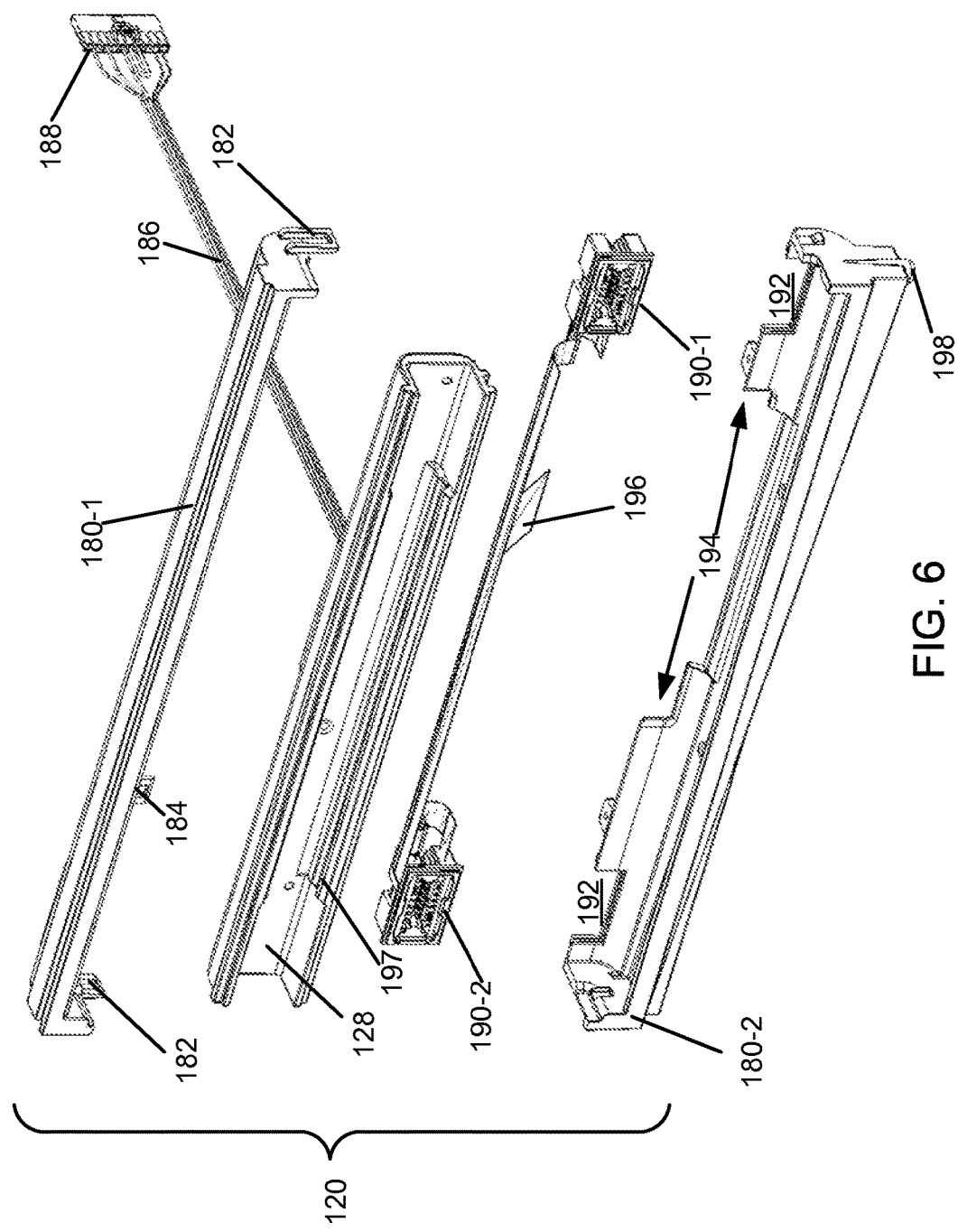
FIG. 6 is an exploded view of a trough compartment within the thermal module.

FIG. 6 shows an exploded view of the trough compartment 120 of the column holder 62. The trough compartment 120 is made of two halves 180-1, 180-2 (generally, 180) held together by two end snaps 182 and a rear snap 184. Mechanical fasteners may also be used to hold the two halves 180 together. Disposed between the two halves 180 is the trough 128 and a pair of electrical sockets 190-1, 190-2 (generally 190) used for electrical 5 connection to an active pre-heater assembly. The sockets 190 sit in appropriately sized rectangular cutout regions 192 in the lower half 180-2 of the trough compartment 120. An electrical ribbon cable 196 is connected between each electrical socket 190 and the electronics within the electronics housing 50 (FIG. 3). The trough 128 can slide to either end of the trough compartment 120 to cover one of the electrical sockets 190.

An electrical cable 186 extends from a rear side of the trough 128 to an electrical connector 188, which plugs into electronics within the housing 50. The electrical cable 186 carries electrical signals for controlling a heater (not shown) and temperature sensor (not shown) mounted to the rear side of the trough 128. The heater is used to heat the trough 128 and the temperature sensor measures temperature of the trough 128. A back surface of the lower half 180-2 of the trough compartment 120 has cutout region 194 to accommodate the cable 186 when the trough 128 slides from one end of the compartment 120 to the other. In addition, the trough 128 has a groove 197, which serves to channel any leakage into the lower half 180-2 of the trough compartment 120.

Extending from the bottom at one end of the lower half 180-2 is a spout 198 for providing a fluidic drainage path for leakage or condensation within the trough 128, the bottom of the lower half 180-2 being sloped towards the spout 198. For example, any condensation forming on the door interior drips into the trough 128 and out through the spout 198.

Figure 7:
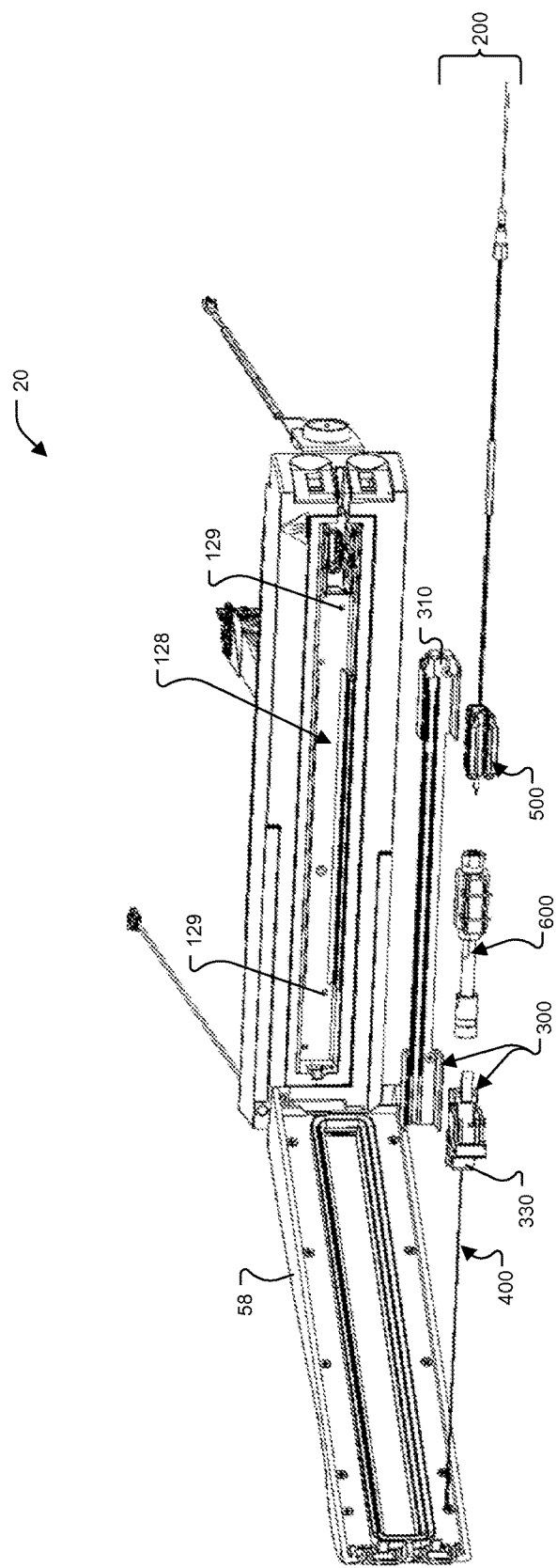
FIG. 7 is an exploded isometric view of the thermal module and a fluidic coupling apparatus.

FIG. 7 shows an isometric view of the thermal module 20 in a first configuration. The front door 58 of the thermal module 20 is open. FIG. 7 also shows an exploded view of the fluidic coupling apparatus 200 which includes of four (4) components: (i) a clamp assembly 300; (ii) a needle barrel assembly 400; (iii) an active pre-heater assembly (APH) 500; and (iv) a column assembly 600, with or without a guard or filter.

In general, the clamp assembly 300 receives and retains the column assembly 600 and establishes a fluid connection between the active pre-heater assembly 500 and the column assembly 600, and between the needle barrel assembly 400 and the column assembly 600. The clamp assembly 300 is installed in the trough 128 by securing the clamp assembly 300 to mounting holes 129 located in either end of the trough 128. The clamp assembly 300 includes a rail 310 and a carriage 330.

Figure 8:
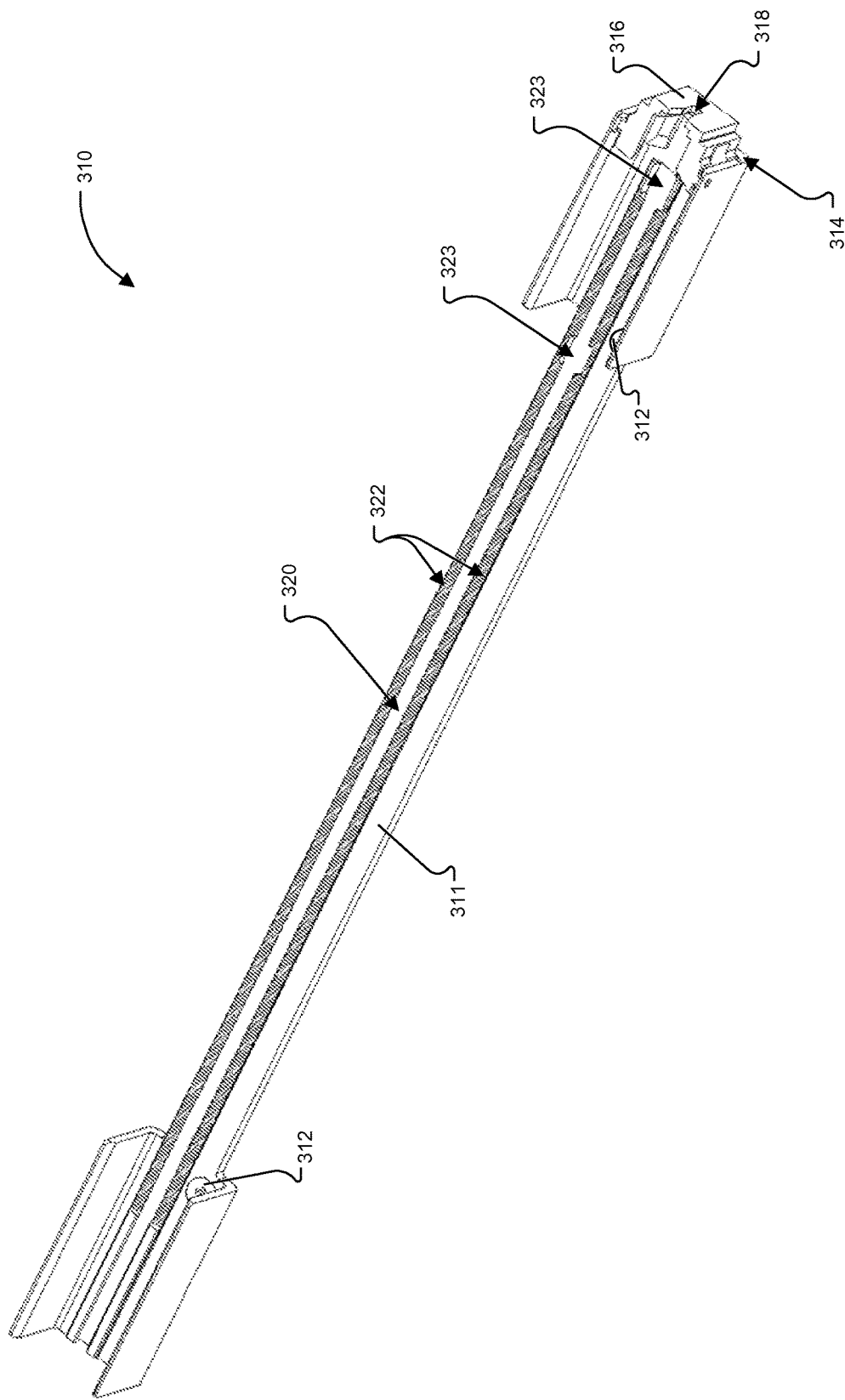
FIG. 8 is an isometric view of a rail of a clamp assembly of the fluidic coupling apparatus.

Referring to FIG. 8, the rail 310 includes a rail body 311 and a rail end cap 316 which is disposed at, and connected to, a distal end 314 of the rail body 311. The rail end cap 316 may be formed as a separate part or may be an integral part of the rail 310. The rail end cap 316 defines a fitting recess 318 that interfaces with the active pre-heater assembly 500 and acts to align an inlet needle of the active pre-heater assembly 500 for connection with the column assembly 600.

The rail body 311 includes mounting holes 312 for securing the rail 310 in the trough 128 (FIG. 7), and a dovetail groove 320 for slidably receiving the carriage 330. The dovetail groove 320 includes teeth 322, which prevent the carriage 330 from sliding relative to the rail 310 when the clamp assembly 300 is in an engaged condition. The rail body 311 also defines slots 323 in the groove 320, which allow the carriage 330 to be assembled to the rail 310. The rail body 311 can have a single piece construction, being molded, machined or otherwise formed from a suitable material such as a thermoplastic resin, or metal.

Figure 9A:
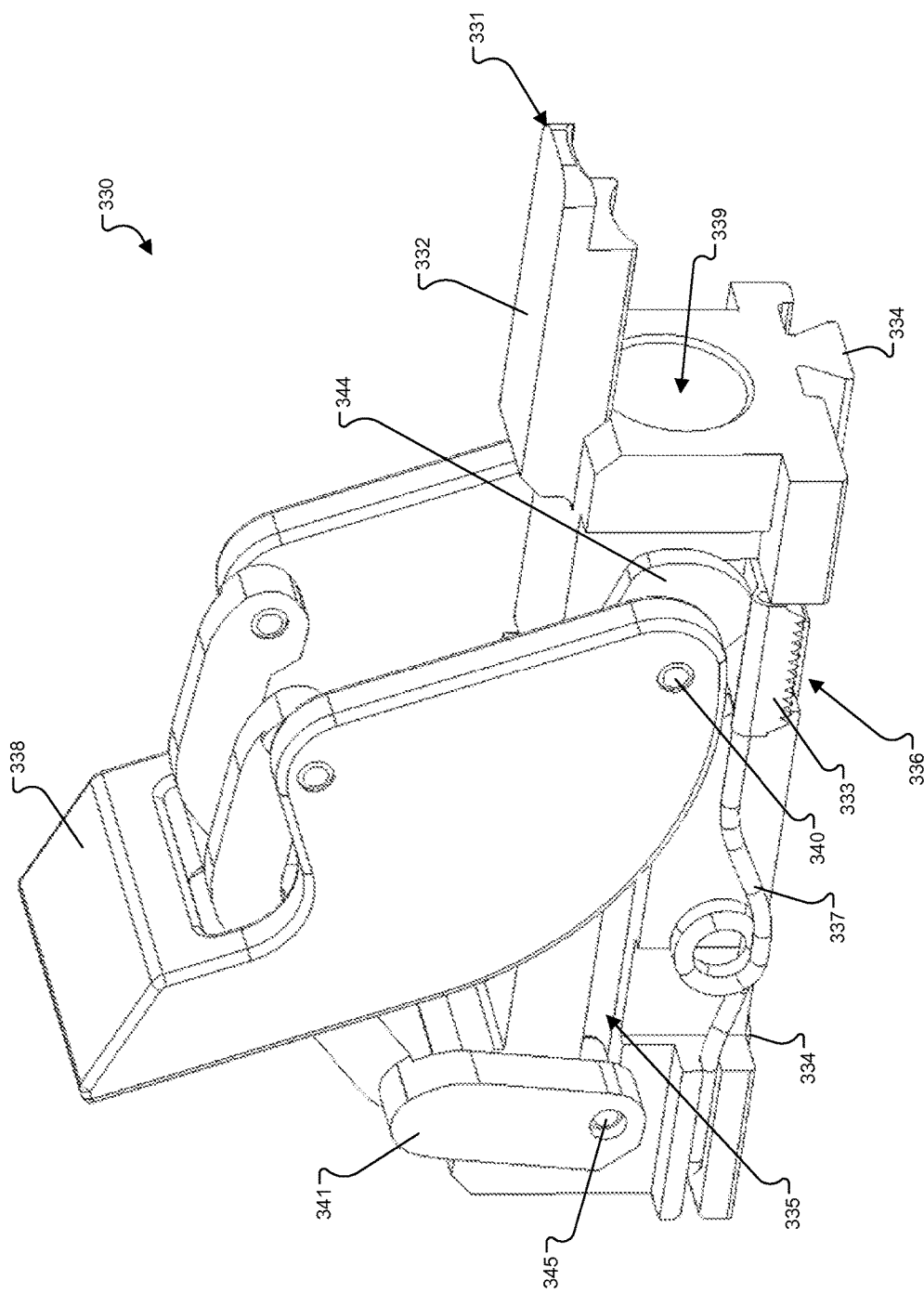
FIGS. 9A & 9B are isometric and side views, respectively, of a carriage of the clamp assembly.
Figure 9B:
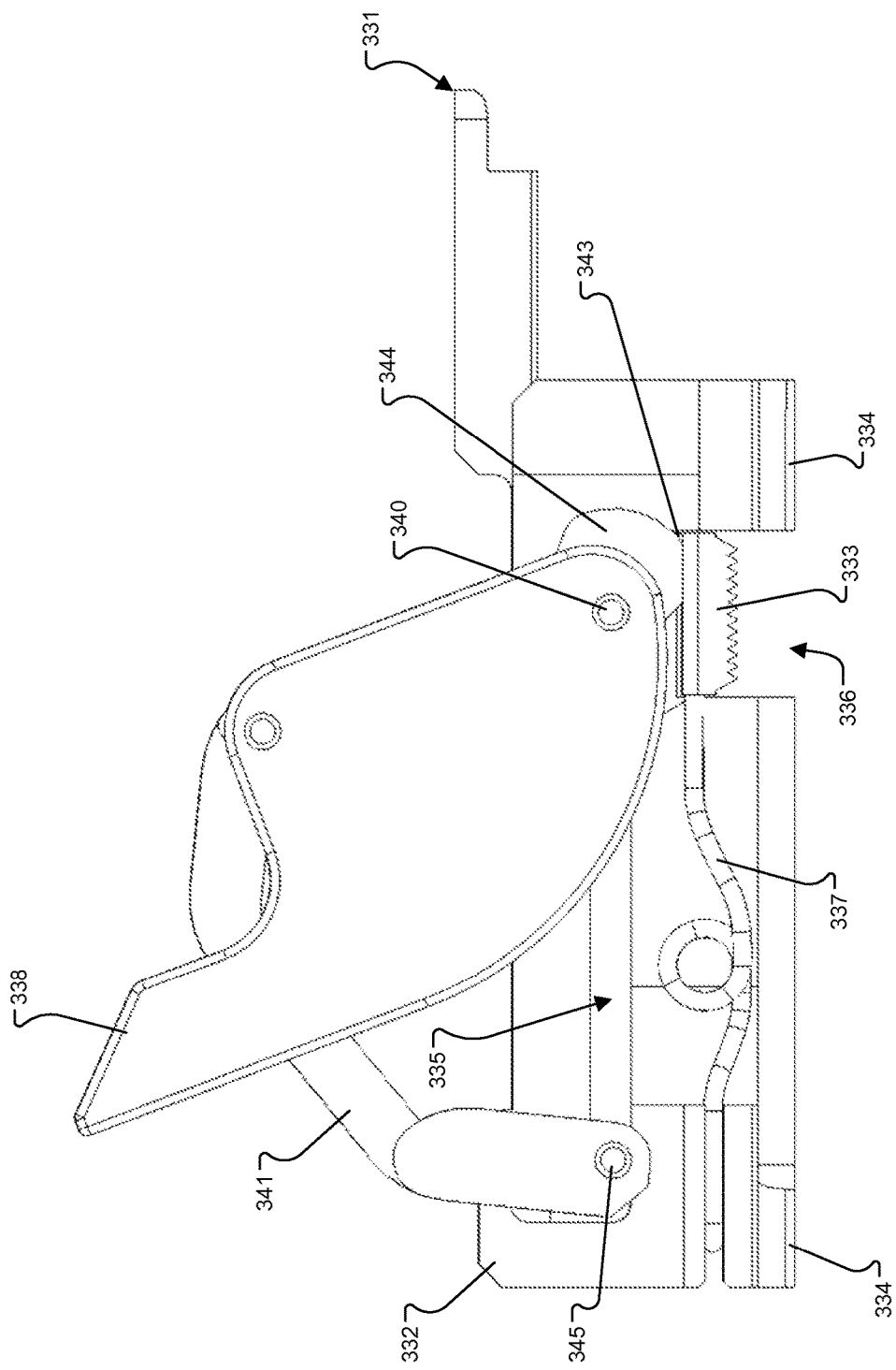

The carriage 330 is slidably mounted to the rail 310. Referring to FIGS. 9A and 9B, the carriage 330 includes a carriage body 332 with a dovetail projections 334 which fit within the slots 323 of the rail 310 (FIG. 8) and slide within the dovetail groove 320 (FIG. 8). At its distal end, the carriage body 332 includes an outwardly extending stop feature 331, which, during use, overlies the outlet end of the column assembly 600 and helps to inhibit the column assembly 600 from popping up and out of place during loading. A cylindrical bore 339 for receiving the needle barrel assembly 400 extends the length of the carriage body 332. The carriage body 332 is also provided with a slot 335 for interfacing with an arm 341 and an aperture 336 for accommodating a foot 333. The carriage body 332 can have a single piece construction, being molded, machined or otherwise formed from a suitable material such as a metal, or a thermoplastic resin.

The foot 333 is displaceable, relative to the carriage body 332, and is mounted to the carriage body 332 via a spring (e.g., a cantilever spring 337). A first end of the cantilever spring 337 is connected to the carriage body 332, and a second, opposite end of the cantilever spring 337 is connected to the foot 333. The cantilever spring 337 biases the foot 333 upwards towards the carriage body 332 such that, when the clamp assembly 300 is in a disengaged condition, teeth 342 of the foot 333 do not engage the teeth 322 of the rail 310, thus allowing the carriage body 332 to move relative to the rail 310. The foot 333 also defines an upwardly extending protrusion 343, which, as discussed below, helps to properly position the needle barrel assembly 400, relative to the carriage body 332, when the needle barrel assembly 400 is loaded into the carriage 330. The foot 333 can be molded, machined or otherwise formed from a suitable material such as a metal, or a thermoplastic resin.

The carriage 330 also includes a lever 338 that is attached to the carriage body 332 at a hinge 340. The lever 338 includes a cam 344, which, when the clamp assembly 300 is in an engaged condition, displaces the foot 333 downward, away from the carriage body 332, such that the teeth 342 of the foot 333 engage the teeth 322 of the rail 310 and thereby inhibit movement of the carriage body 332 relative to the rail 310. The lever 338 is also hingedly attached to, and controls movement of, the arm 341. The arm 341 includes a pair of pins 345, which are slidably received in the slot 335 of the carriage body 332 and which, as discussed below, engage the needle barrel assembly 400 to control movement of the needle barrel assembly 400 relative to the carriage body 332. The lever 338 and the arm 341 can be molded, machined or otherwise formed from a suitable material such as thermoplastic resin, or a metal.

Figure 10:
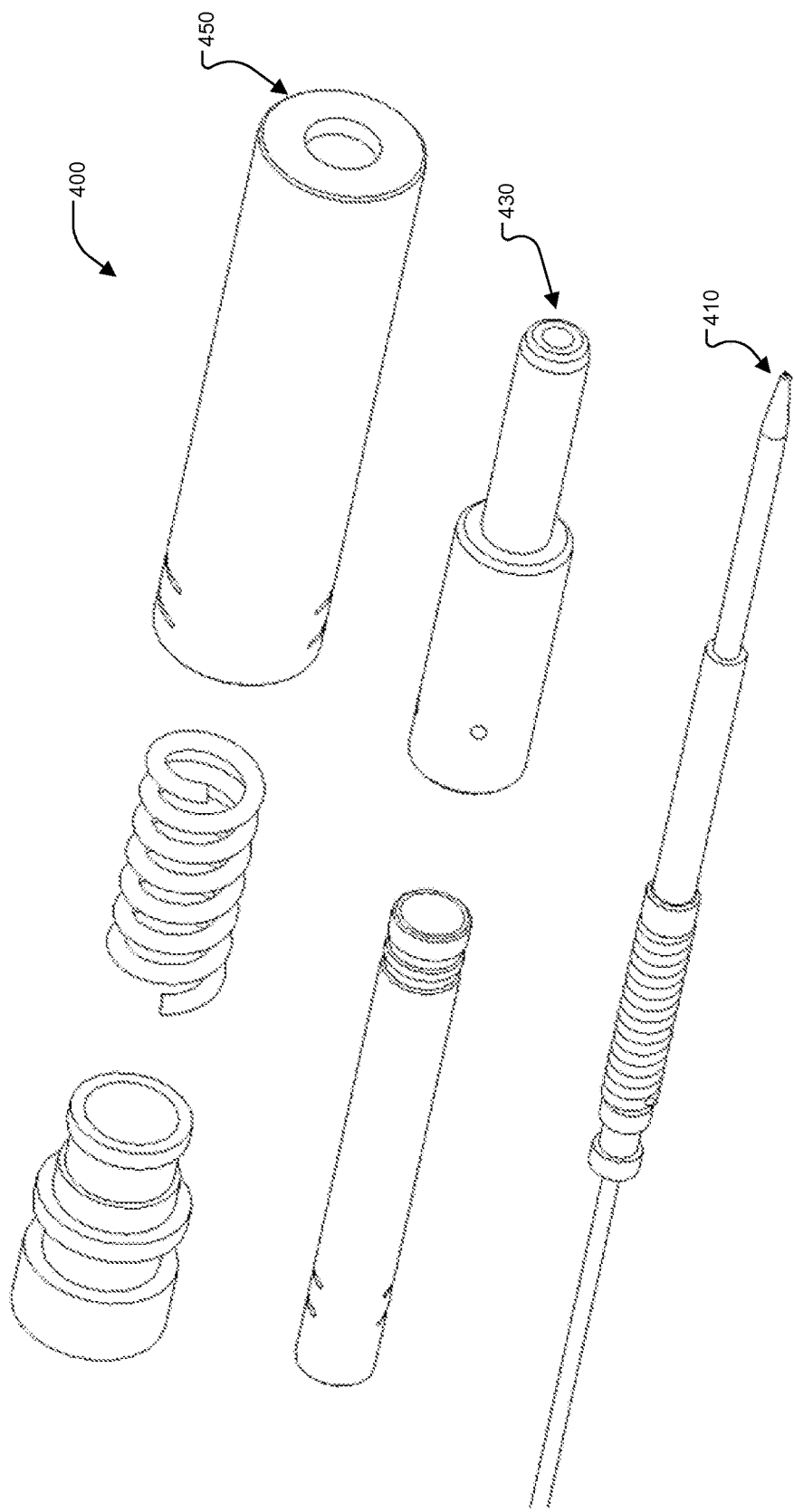
FIG. 10 is an exploded isometric view of a needle barrel assembly of the fluidic coupling apparatus.
Figure 11:
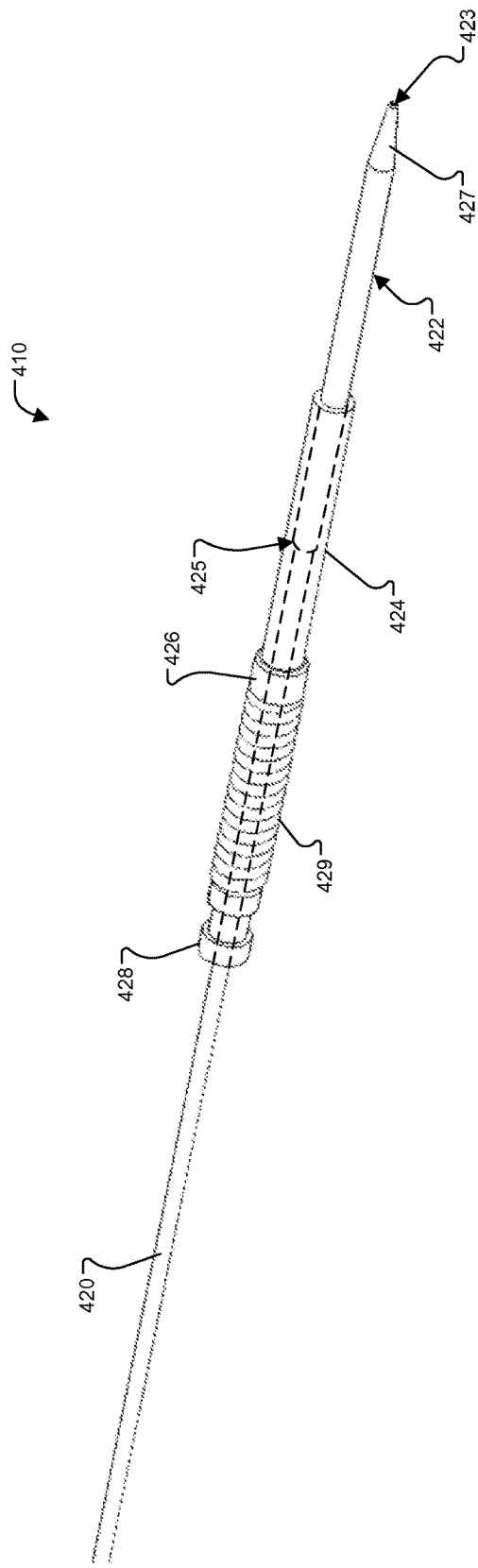
FIG. 11 is an isometric view of an outlet tubing sub-assembly of the needle barrel assembly of FIG. 10.

The needle barrel assembly 400 is received within the cylindrical bore 339 of the carriage body 332. Referring to FIG. 10, the needle barrel assembly 400 is a fluidic assembly that includes (i) an outlet tubing sub-assembly 410; (ii) an inner barrel sub-assembly 430; and (iii) an outer barrel sub-assembly 450. Referring to FIG. 11, the outlet tubing sub-assembly 410 includes an outlet capillary tubing 420, a hollow outlet needle 422, a metal tube sleeve 424, a bushing 426, an inner spring retainer 428, and an inner spring 429. The outlet capillary tubing 420 can be metallic or polymeric tubing having an inside diameter of approximately 0.011 inches or less and an outside diameter (OD) of approximately 0.025 inches or less. The outlet needle 422 includes a fluid passage 423 that extends from a first end 425 of the outlet needle 422 to a tapered, second end 427. The outlet needle 422 can be formed (e.g., drawn, molded, machined, etc.) from metal. A first end of the outlet capillary tubing 420 is received within a counterbore hole at the first end 425 of the outlet needle 422 and is secured therein, e.g., by adhesive, welding, or deformation (e.g., crimping) of the outlet needle 422. The metal tube sleeve 424 is disposed circumferentially about a shank of the outlet needle 422 and about a first end of the outlet capillary tubing 420 and is attached thereto, e.g., by welding or adhesive.

The bushing 426 is disposed circumferentially about the metal tube sleeve 424 and is fixed thereto, e.g., by welding, adhesive, or deformation of the bushing 426. The bushing 426 being molded, machined or otherwise formed from a suitable material such as thermoplastic resin, or a metal. Alternatively, the bushing 426 may be formed as an integral part of the metal tube sleeve 424. The inner spring retainer 428 is disposed circumferentially about the capillary tubing 420 and is slidable relative thereto. The inner spring 429 is disposed circumferentially about the capillary tubing 420 between the bushing 426 and the inner spring retainer 428.

Figure 13:
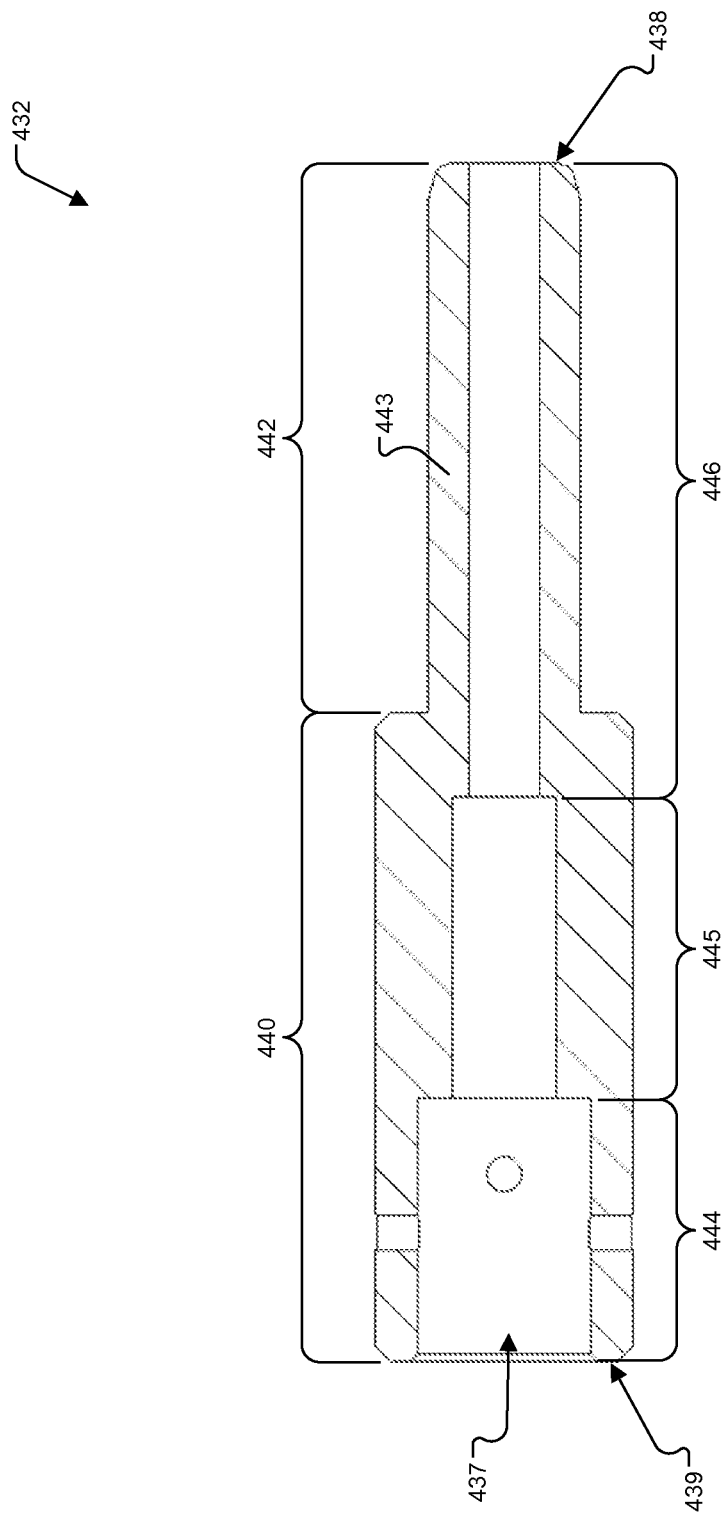
FIG. 13 is a cross-sectional side view of an inner barrel of the inner barrel sub-assembly of FIG. 12.

Referring to FIG. 12, the inner barrel sub-assembly 430 includes an inner barrel 432 and a pilot retainer 436. As shown in FIG. 13, the inner barrel 432 includes a first region 440 having a first diameter, and a second region 442 that is smaller in diameter than the first region 440 and which defines an outlet pilot 443. The inner barrel 432 also has a central bore 437 that extends through the inner barrel 432 from a distal end 438 through the proximal end 439. The central bore 437 includes a first portion 444 having a first diameter, a second portion 445 having a second diameter that is smaller than the first diameter, and a third portion 446 having a third diameter that is smaller than the second diameter. The inner barrel 432 can have a single piece construction, being molded, machined or otherwise formed from a suitable material such as thermoplastic resin, or a metal; or, in some cases, may be formed from multiple parts connected together.

Figure 14:
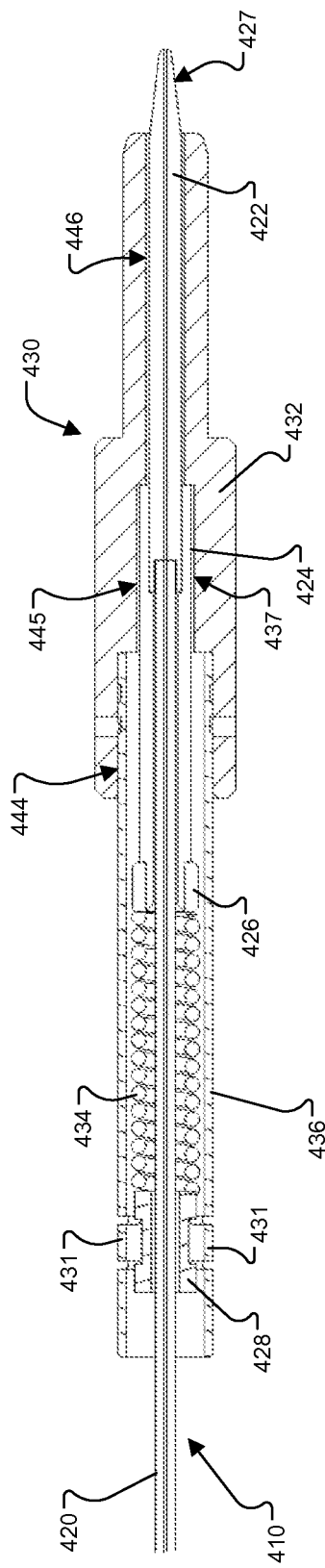
FIG. 14 is a cross-sectional side view of the outlet tubing sub-assembly assembled into the inner barrel sub-assembly.

As shown in FIG. 14, the outlet tubing sub-assembly 410 is assembled with the inner barrel sub-assembly 430 by passing the outlet needle 422 through the central bore 437 until the distal end of the metal tube sleeve 424 abuts a shoulder formed by the junction of the second portion 445 and the third portion 446 of the central bore 437. The inner spring 434 is disposed around the outlet capillary tubing 420 and is positioned such that a first end of the inner spring 434 abuts against the bushing 426. The inner spring retainer 428 is positioned adjacent a second, opposite end of the inner spring 434. The pilot retainer 436 is attached to the inner barrel 432, e.g., press fit or welded within the first portion 444 of the central bore 437, and a pair of tabs 431 in the pilot retainer 436 are swaged into contact with the inner spring retainer 428 to retain inner spring retainer 428 in place relative to the inner barrel sub-assembly 430 such that the inner spring 434 biases the outlet needle 422 outwardly from the central bore 437. In this regard, the inner spring 434 is pre-loaded against the bushing 426 such that the tapered end 427 of the outlet needle 422 is biased outward through the central bore 437. Following assembly, the capillary tubing 420 and the outlet needle 422 are displaceable relative to the inner barrel sub-assembly 430. The outlet tubing sub-assembly 410 and the inner barrel sub-assembly 430 can then be assembled with the outer barrel sub-assembly 450.

Figure 15:
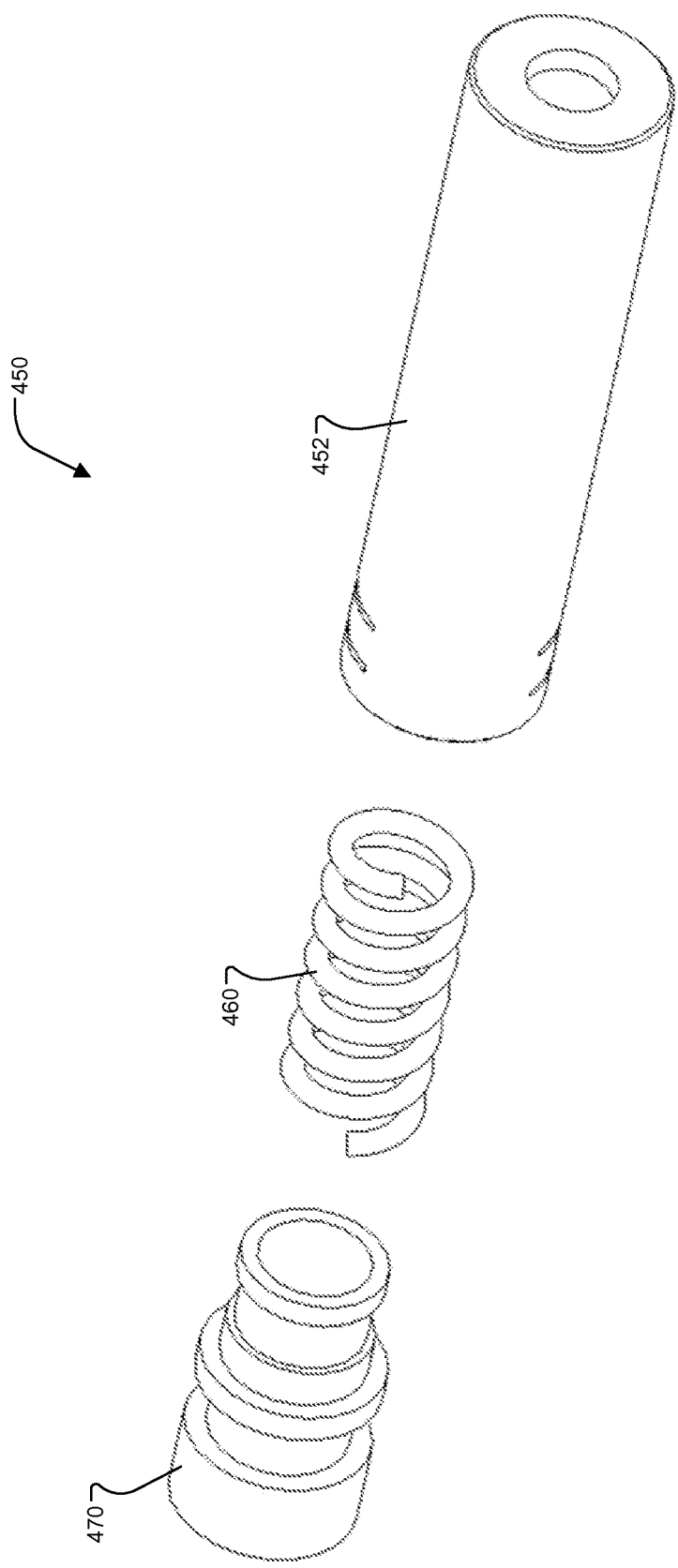
FIG. 15 is an isometric view of an outer barrel sub-assembly of the needle barrel assembly of FIG. 10.
Figure 16:
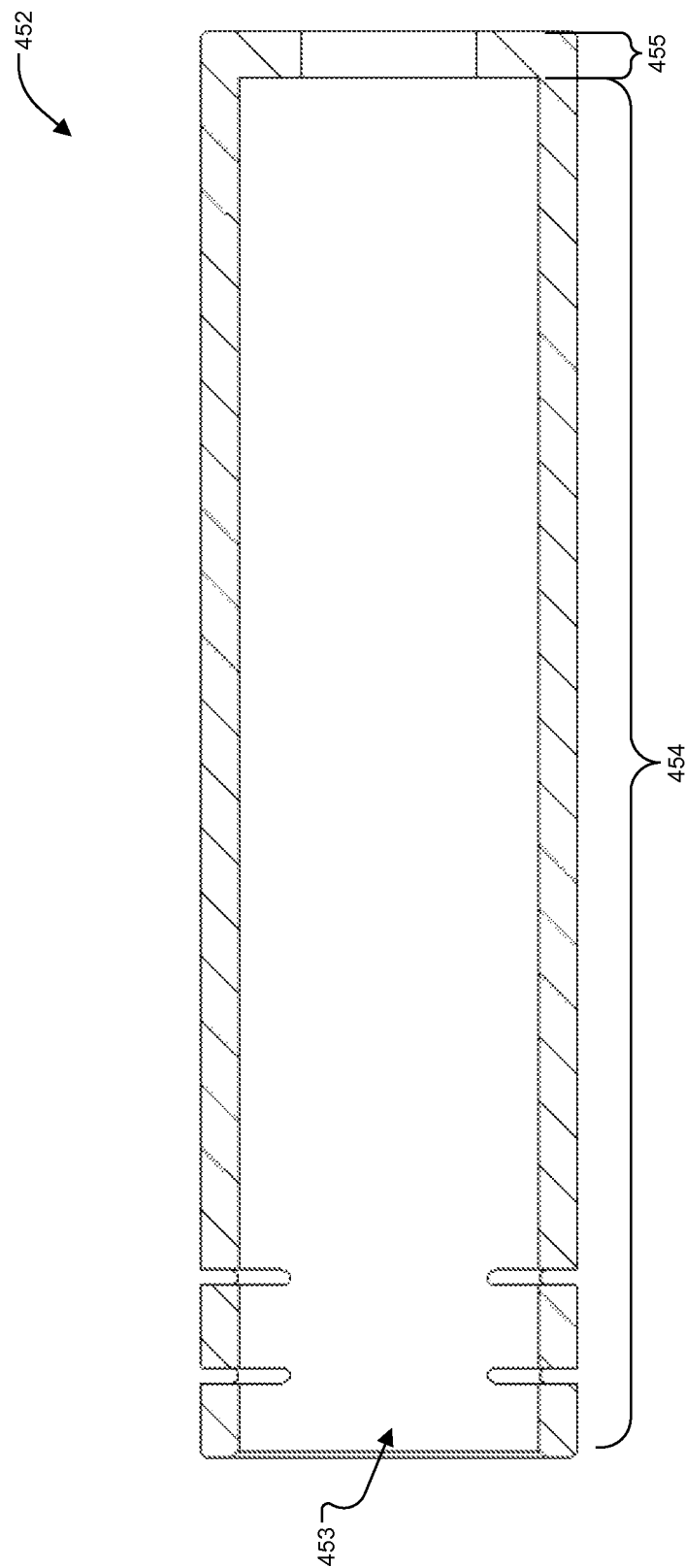
FIG. 16 is a cross-sectional side view of an outer barrel of the outer barrel sub-assembly of FIG. 15.

Referring to FIG. 15, the outer barrel sub-assembly 450 includes an outer barrel 452, an outer spring 460, and an outer spring retainer 470. As shown in FIG. 16, the outer barrel 452 includes a central opening 453 that includes a first portion 454 having a first diameter, and a second portion 455 having a second diameter that is smaller than the first diameter. The outer barrel 452 can have a single piece construction, being molded, machined or otherwise formed from a suitable material such as thermoplastic resin, or a metal.

Figure 17:
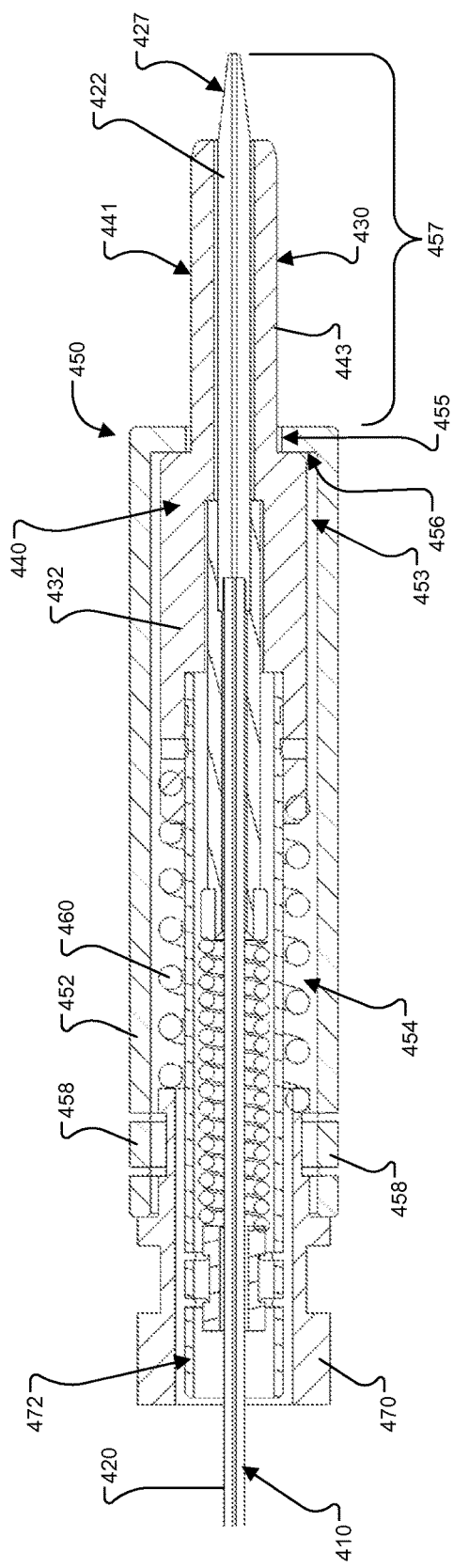
FIG. 17 is a cross-sectional side view of the needle barrel assembly.

As shown in FIG. 17, the outlet tubing sub-assembly 410 and inner barrel sub-assembly 430 are assembled with the outer barrel sub-assembly 450 by passing the outlet needle 422 and outlet pilot 443 through the central opening 453 until a distal end of the first region 440 of the inner barrel 432 abuts a shoulder 456 formed by the junction of the first portion 454 and the second portion 455 of the central opening 453 thereby preventing further forward movement of the inner barrel sub-assembly 430 relative to the outer barrel sub-assembly 450. When assembled, the outlet pilot 443 extends beyond the distal end of the outer barrel 452, and the tapered, second end 427 of the outlet needle 422 extends beyond the distal end of the outlet pilot 443. The outlet needle 422 and the outlet pilot 443 together forming an outlet column fitting 457.

The outer barrel 452 includes a pair of deformable tabs 458 which are swaged into contact with the outer spring retainer 470 to attach the outer spring retainer 470 to the outer barrel 452 such that the outer spring 460 is retained within the first portion 454 of the central opening 453. The outer spring retainer 470 includes a through hole 472 through which the outlet capillary tubing 420 and the proximal end of the pilot retainer 436 can pass. The outer spring retainer 470 also provides a surface against which the outer spring 460 can act and is positioned to pre-load the outer spring 460 against the inner barrel 432 such that the outlet pilot 443 of the inner barrel 432 is biased outward through the central opening 453. Following assembly, the inner barrel sub-assembly 430 is displaceable relative to the outer barrel sub-assembly 450, and the outlet needle 422 and the outlet capillary tubing 420 of the outlet tubing sub-assembly 410 remain displaceable relative to the inner barrel sub-assembly 430.

Figure 18:
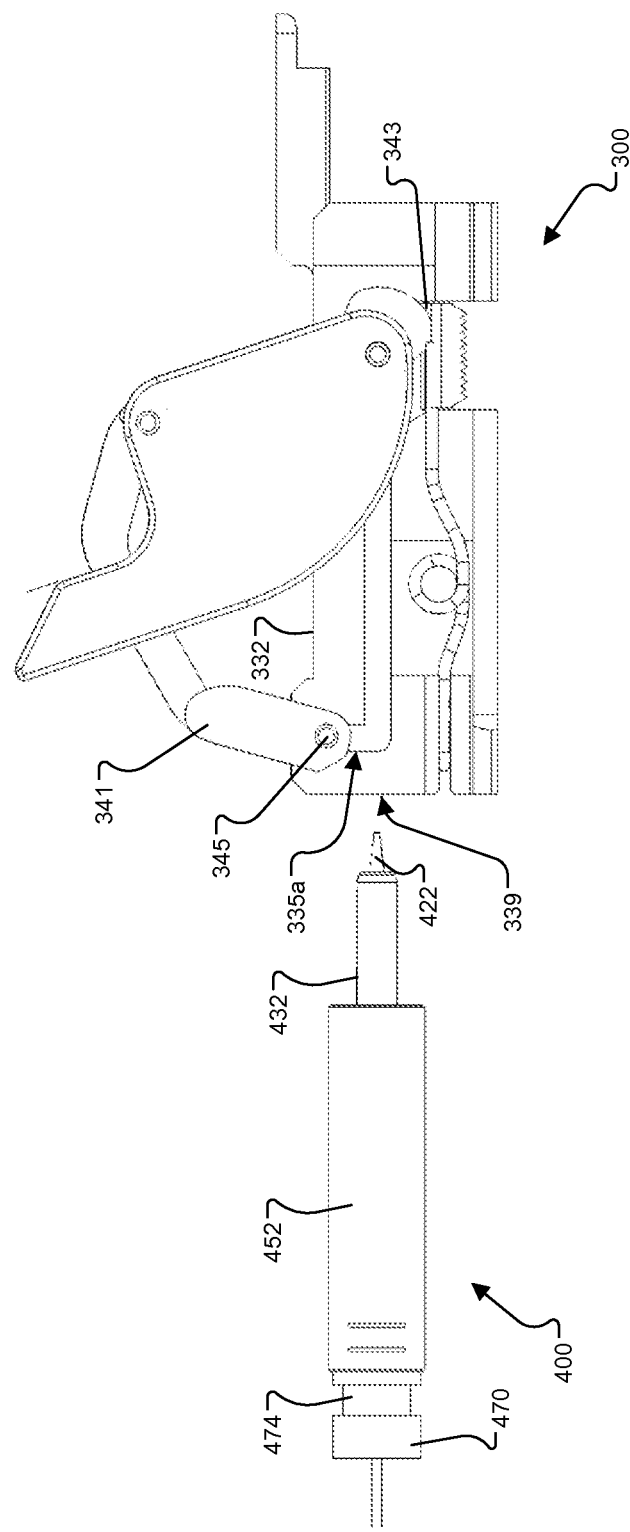
FIG. 18 is a side view illustrating insertion of the needle barrel assembly into the carriage.
Figure 19A:
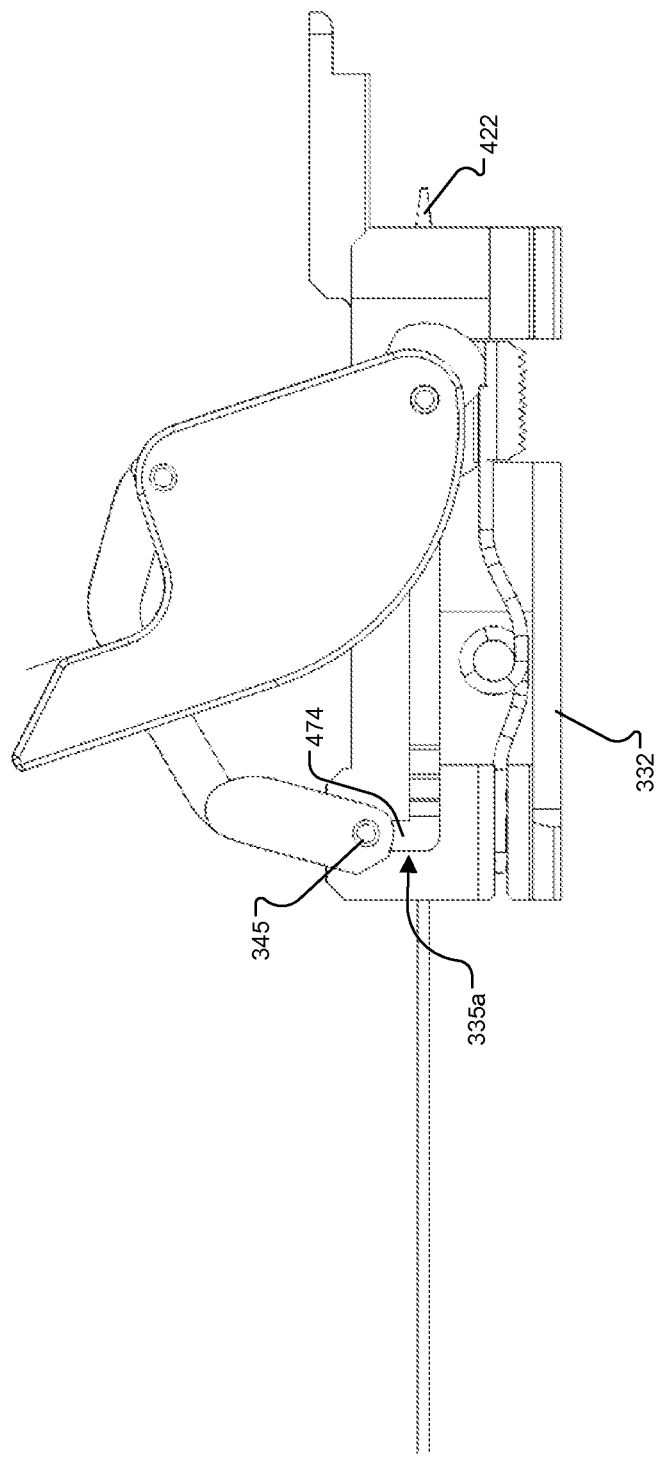
FIG. 19A is a side view of the needle barrel assembly loaded in the carriage.
Figure 19B:
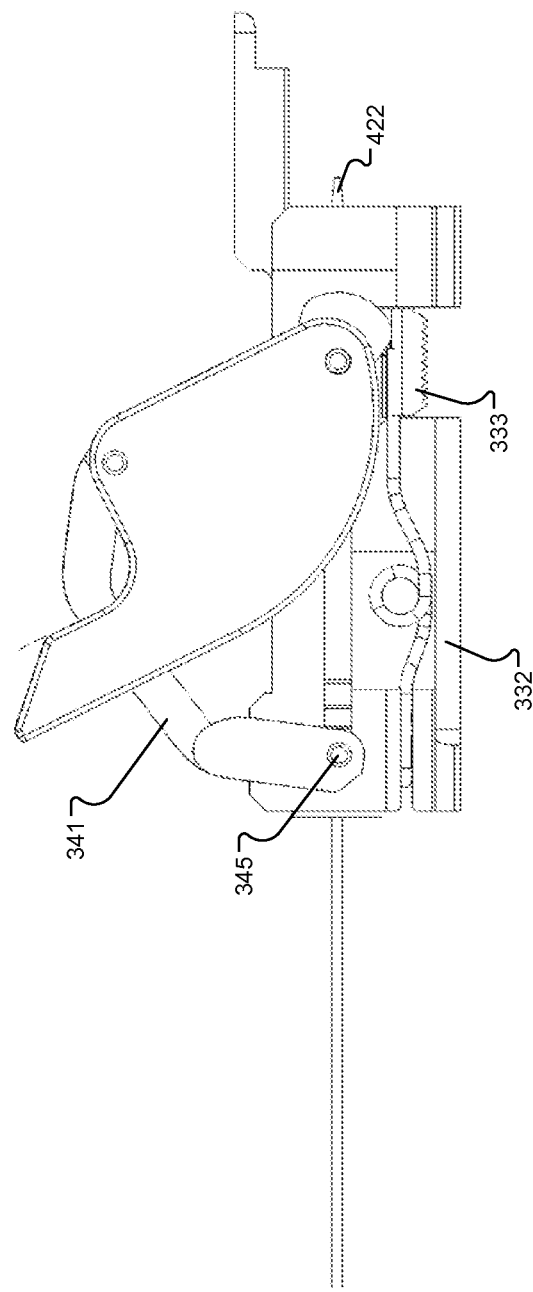
FIG. 19B is a side view of the carriage and needle barrel assembly showing a lever of the carriage in a disengaged position.

With reference to FIG. 18, the needle barrel assembly 400 is assembled with the clamp assembly 300 by inserting the needle barrel assembly 400, outlet needle 422 first, into the cylindrical bore 339 in the carriage body 332 until the distal end of the outer barrel 452 abuts against the upwardly extending protrusion 343 on the foot 333. In this position, an annular recess 474 in the outer spring retainer 470 will be aligned with a vertical segment 335a of the slot 335 in the carriage body 332 and positioned to receive the pins 345 on the arm 341, as shown in FIG. 19A. The pins 345 slide down the vertical segment 335a of the slot 335 and are received in annular recess 474, as shown in FIG. 19B, for controlling movement of the needle barrel assembly 400 relative to the clamp assembly 300.

Figure 19C:
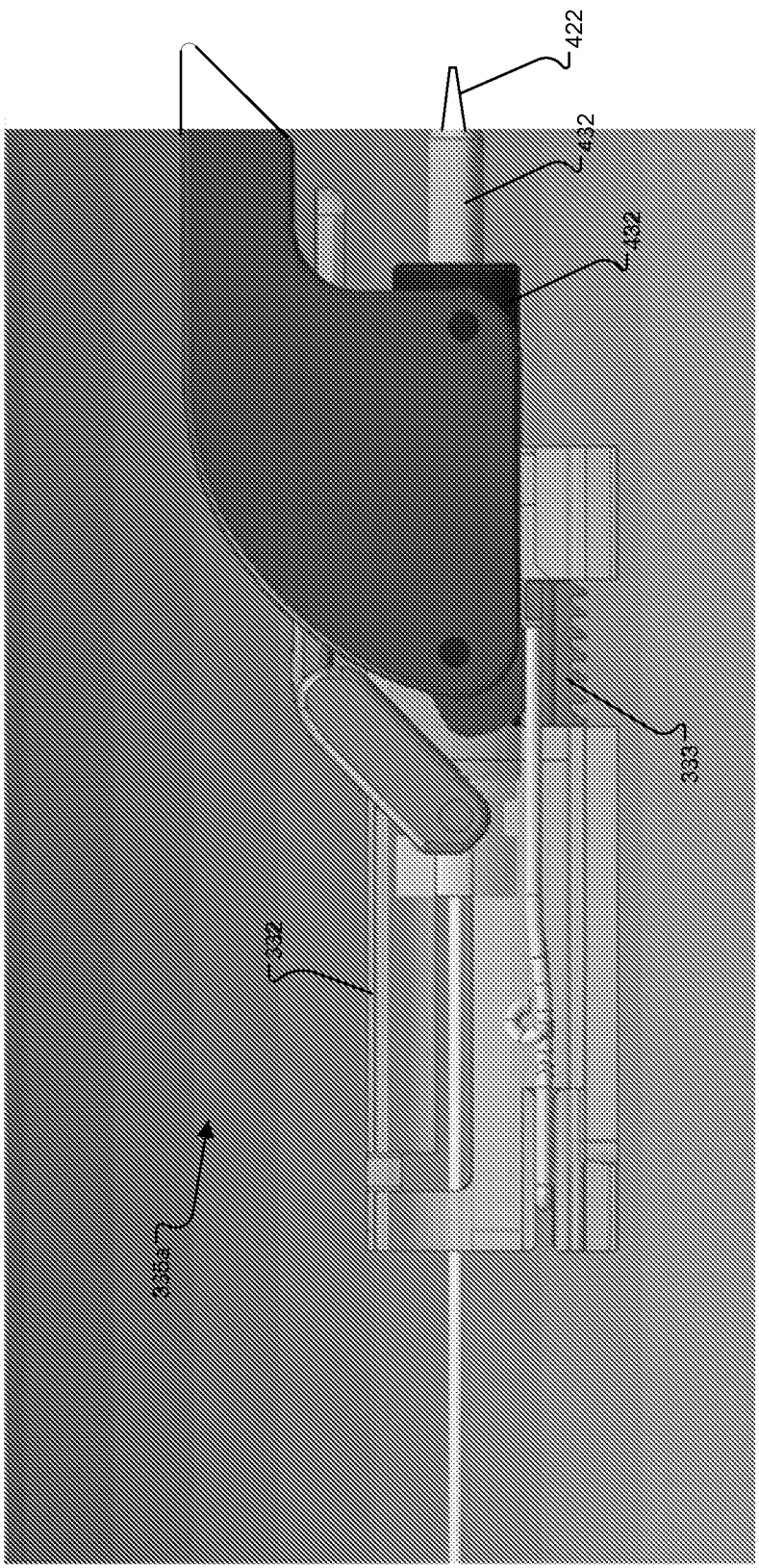
FIG. 19C is a side view of the carriage and needle barrel assembly showing a lever of the carriage in an engaged position.

The lever 338 of the clamp assembly 300 is displaceable between a disengaged position (FIG. 19B) and an engaged position (FIG. 19C). The displacement of the lever 338 from the disengaged position to the engaged position displaces the needle barrel assembly 400 such that, in the engaged position, the distal ends of the inner and outer barrels 432, 452 and the outlet needle 422 protrude further outwardly from the carriage body 332. Displacement of the lever 338 also displaces foot 333 downward, away from the carriage body 332, such that, when the carriage 330 is mated with the rail 310 (FIG. 8), the teeth 342 on the foot 333 engage the teeth 322 on the rail 310 to lock the carriage 310 in place relative to the rail 310.

Figure 20:
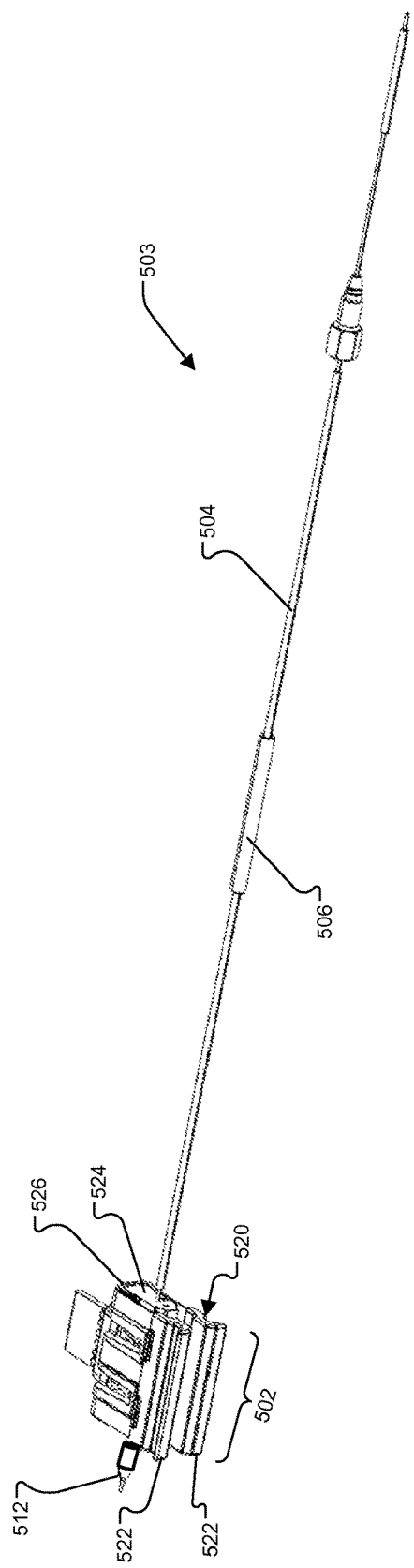
FIG. 20 is an isometric view of an active pre-heater assembly.

Turning now to the active pre-heater assembly 500, which is a fluidic assembly that is utilized to heat liquid before the liquid reaches the column assembly 600 retained within the clamp assembly 300. FIG. 20 shows an isometric view of an implementation of the active pre-heater assembly 500 which includes a heater block sub-assembly 502 and an inlet tubing sub-assembly 503. The inlet tubing sub-assembly 503 includes inlet capillary tubing 504, a polymeric tube sleeve 506 shrink-wrapped around a section of the inlet capillary tubing 504, and an inlet column fitting 512. The heater block sub-assembly 502 comprises a spring carrier 520 made of a pair of opposing prongs 522 spaced apart by a rear wall 526, a heater block 524 disposed between the prongs 522, and a printed circuit board 528 extending from a reverse side of the rear wall 526. The inlet capillary tubing 504 passes into a channel 530 in one side of the heater block 524. The heater block 524 is made of aluminum or some other thermally conductive alloy. The active pre-heater assembly 500 can be constructed as a single inseparable unit or as multiple separable components that snap together.

The inlet capillary tubing 504 fluidically connects the active pre-heater assembly 500 to the sample manager for receiving a sample-solvent composition therefrom. The inlet column fitting 512 is for connecting the other end of the inlet capillary tubing 504 to a liquid chromatography column disposed within the trough compartment 120.

Figure 21:
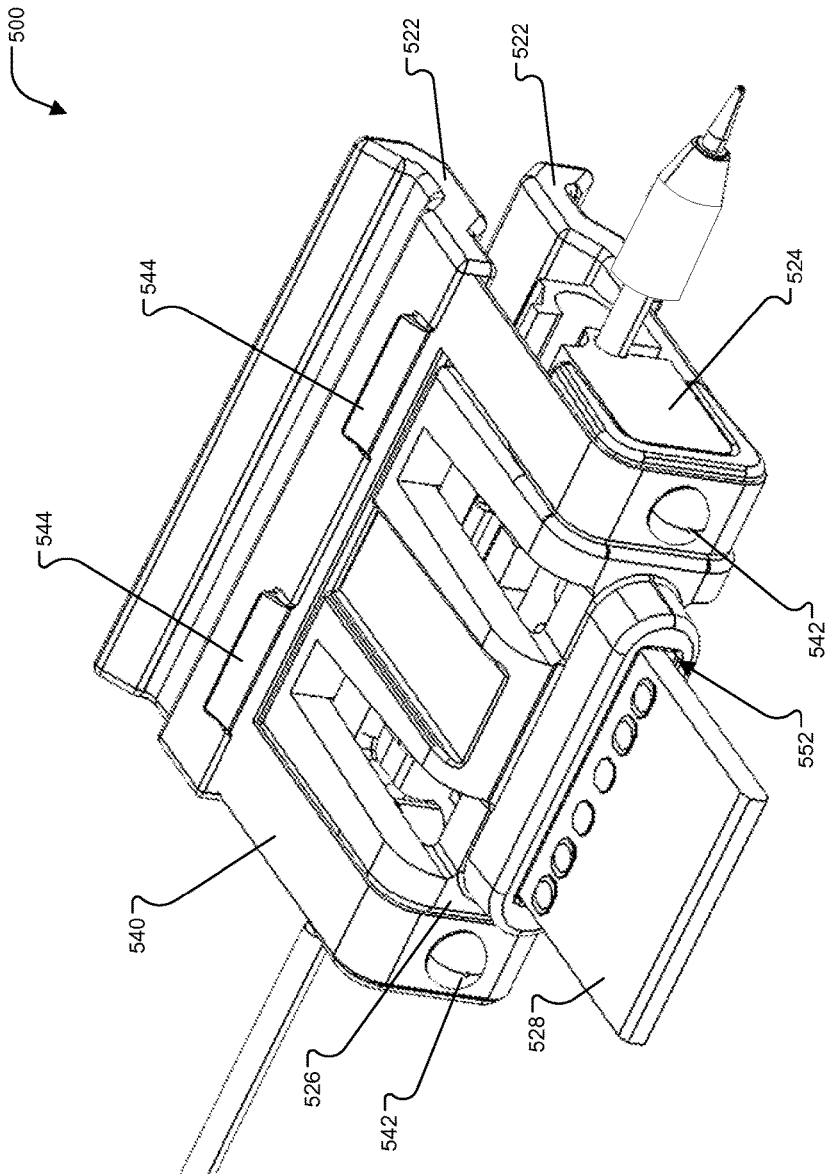
FIG. 21 is a reverse isometric view of the active pre-heater assembly.

FIG. 21 is a reverse view of the active pre-heater assembly 500. The opposing prongs 522 of the spring carrier 520 are integrally formed with a metallic leaf-spring 540. The leaf-spring 540 is a flat, rectangular window of metallic material that is curved into an arcuate shape defined by the prongs 522. The leaf-spring 540 biases the prongs 522 of the spring carrier 520 apart and bends when the prongs 522 are pinched together.

The leaf-spring 540 has openings through which project molded posts 542, which are melted to hold the leaf-spring 540. Each prong 522 of the spring carrier 520 has a pair of raised ramps 544 that snap into openings in interior surfaces of the receptacle 140 (FIG. 5). A raised edge 542 of each prong 522 provides a finger grip that a user can use to pinch the prongs 522 together in order to decouple the ramps 544 from the receptacle 140 so that the spring carrier 520 can be removed.

The printed circuit board 528 of the heater block sub-assembly 502 is aligned to project through a rear side opening 552 in the rear wall 526 of the spring carrier 520 for electrical connection with one of the electrical sockets 190 of the trough compartment 120. Electronics connected to the circuit board 528 can include a temperature sensor (e.g., a thermistor) and a heater cartridge. Both the temperature sensor and the heater cartridge can be embedded (e.g., embedded in epoxy filled cavities) in the heater block 524 with electrical connections to the circuit board 528. Circuitry on the circuit board 528 uses temperature measured by the temperature sensor to limit operation of the heater cartridge and thus the maximum temperature reached by the heater block 524. Additional details of the heater block 524 and printed circuit board 528 are described in International Patent Application No. PCT/US11/20803, filed Jan. 11, 2011, the complete disclosure of which is incorporated herein by reference.

Figure 22:
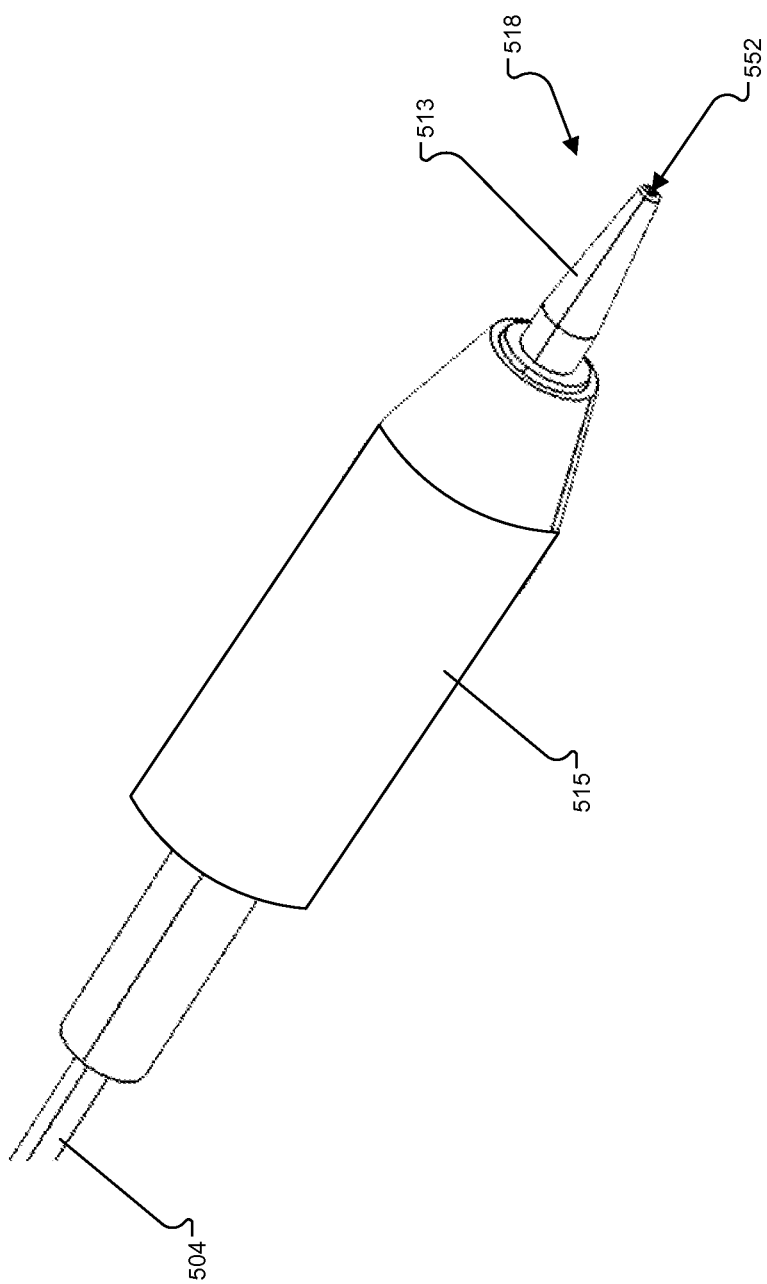
FIG. 22 is an isometric view of an inlet column fitting.

Referring to FIG. 22, the inlet column fitting 512 includes a hollow inlet needle 513 and an inlet pilot 515. The inlet needle 513 includes a fluid passage 516 that extends from a first end of the inlet needle 513 to a tapered, second end 518. The inlet needle 513 being metal. A first end of the inlet capillary tubing 504 is received within a counterbore hole at the first end of the inlet needle 513 and is secured therein, e.g., by adhesive, welding, or deformation (e.g., crimping) of the inlet needle 513. The inlet capillary tubing 504 can be metallic or polymeric tubing having an inside diameter of approximately 0.011 inches or less and an outside diameter (OD) of approximately 0.025 inches or less. The inlet pilot 515 is disposed circumferentially about a distal end portion of the capillary tubing 504 and about a shank 521 of the inlet needle 513 such that the tapered, second end 518 of the inlet needle 513 extends outwardly from the inlet pilot 515. The inlet pilot 515 can be fixed to the inlet needle 513, e.g., by welding, adhesive, or deformation of the inlet pilot 515. Alternatively or additionally, the inlet pilot 515 may be fixed to the heater block 524 such as by welding, or may be formed as an integral part of the heater block 524. The inlet pilot 515 can be molded, machined or otherwise formed from a metal (e.g., aluminum). The inlet capillary tubing 504, itself, is soldered in place within a serpentine path through the heater block 524 as described in International Patent Application No. PCT/US11/20803, filed Jan. 11, 2011.

During assembly, the heater block sub-assembly 502 is installed in the exposed one of the sockets 190-1, 190-2 in the trough compartment 120 depending on the position of the trough 128. When installed, the inlet pilot 515 is received and retained in the fitting recess 318 of the rail end cap 316 on the rail 310 and the inlet capillary tubing 504 extends through the rail end cap 316, inlet needle 513 first, for connection with the column assembly 600. The rail end cap 316 keeps the inlet needle 513 and the inlet pilot 515 aligned, relative to the trough, in position for receiving an end of the column assembly 600.

Figure 23:
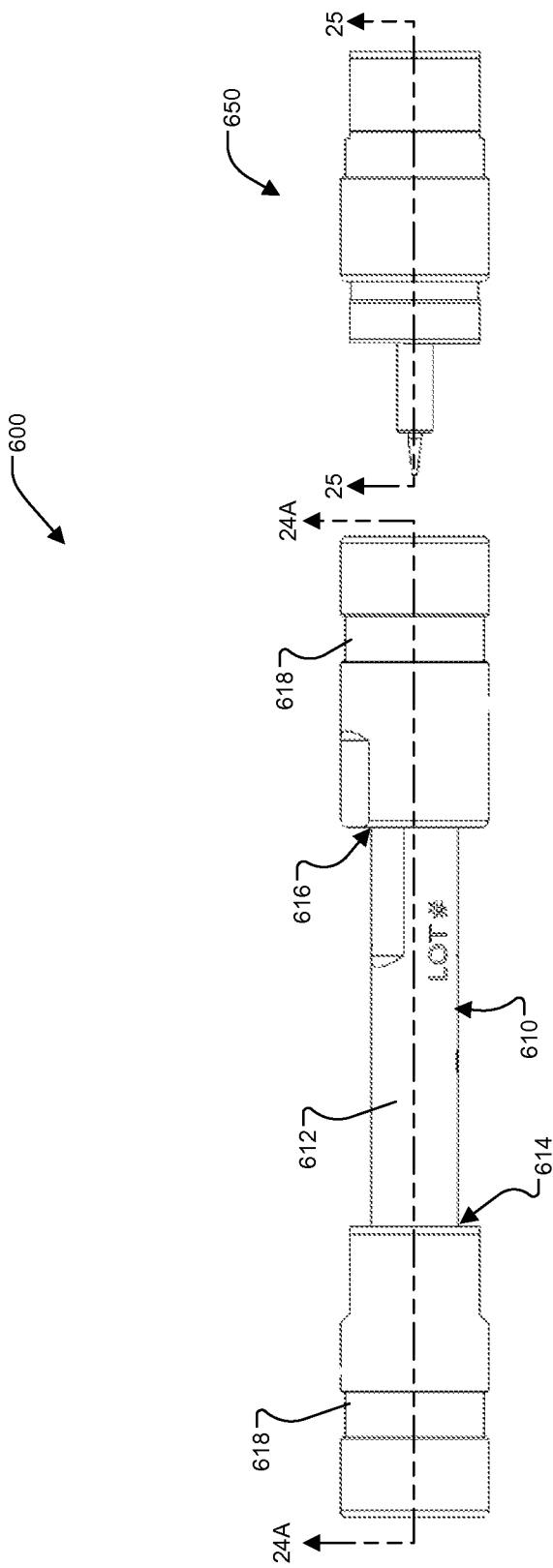
FIG. 23 is an exploded side view of a column assembly.
Figure 24A:
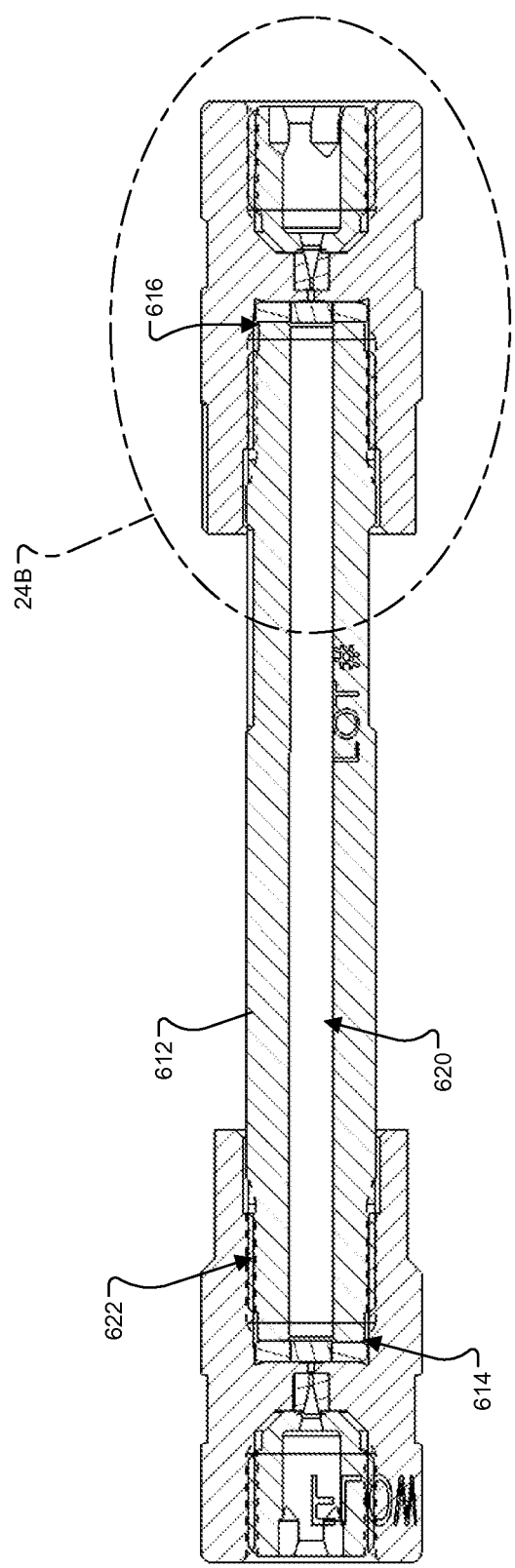
FIG. 24A is a cross-sectional side view of a chromatography column, taken along line 24A-24A of FIG. 23.
Figure 24B:
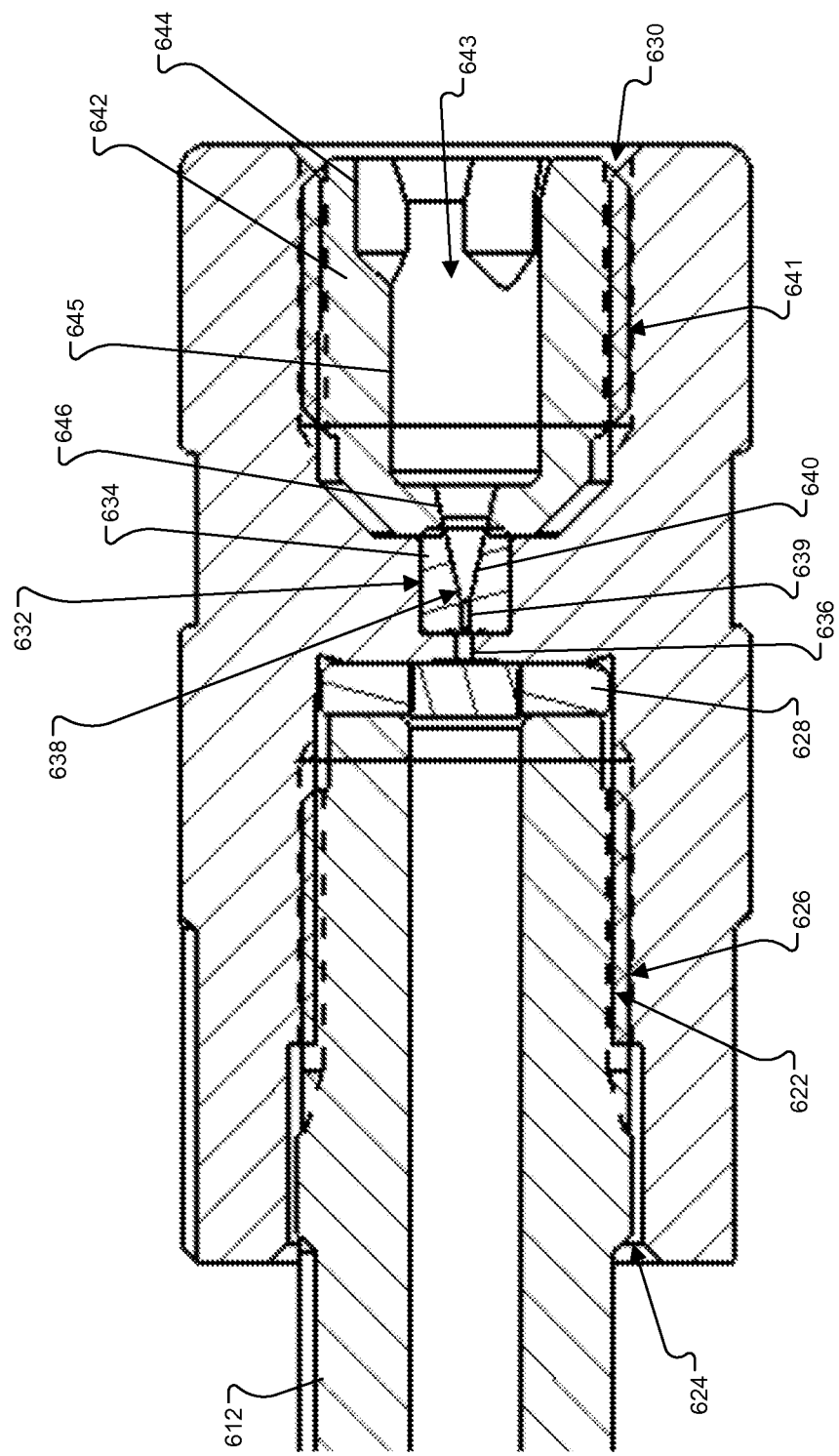
FIG. 24B is a detail view of an end fitting from FIG. 24A.

FIG. 23 illustrates an implementation of the column assembly 600 which includes a chromatography column 610 and a cartridge sub-assembly 650. The chromatography column 610 includes an elongate body 612 that extends between first and second ends 614, 616 with an end fitting 618 disposed at each end. Referring to FIGS. 24A & 24B, the elongate body 612 includes a cylindrical bore 620 which extends the length of the elongate body 612 from the first end 614 to the second end 616. The cylindrical bore 620 receives and retains a packing material. Each of the ends 614, 616 includes a threaded section 622 for mounting the end fittings 618. The elongate body 612 and end fittings 618 each being molded, machined or otherwise formed from a suitable material such as a metal.

Referring to FIG. 24B, each of the end fittings 618 defines a first cavity 624 which receives one of the ends 614, 616 of the elongate body 612. The first cavity 624 includes a threaded portion 626 which mates with the threaded section 622 of the elongate body 612. Alternatively or additionally, the end fittings 618 can be welded to the elongate body 612 or attached with adhesive. A column frit 628, e.g., a porous metal disk, is disposed within the first cavity 624 and is secured against the open end of the elongate body 612 when the end fitting 618 is attached thereto. The end fittings 618 also define a second cavity 630 and a seal recess 632 which extends from the second cavity 630 toward the first cavity 624. The seal recess 632 receives a compliant seal 634, which may be formed of polyimide such as DuPont™ Vespel®, polyether-ether-ketone such as PEEK™ polymer (available from Victrex PLC, Lancashire, United Kingdom), or a deformable metal such as annealed stainless steel. A through-hole 636 extends from the first cavity 624 into the seal recess 632 to provide for fluid communication between the cylindrical bore 620 and a fluid passage 638 defined by the seal 634. The fluid passage 638 includes a small diameter portion 639 which aligns with the through-hole 636, and a tapered portion 640 which extends from an interface with the small diameter portion 639 to an opposite end of the seal 634. The tapered portion 640 has an included angle of less than 40 degrees. The second cavity 630 defines a threaded region 641 which threadingly receives a retainer 642 for retaining the seal 634 within the seal recess 632. This threaded arrangement allows the retainer 642 to be removed for replacing the seal 634 when and if it becomes worn or damaged. The retainer 642 being molded, machined or otherwise formed from a suitable material such as thermoplastic resin, or a metal. The retainer 642 is threaded into the second cavity 630 and includes a central passage 643 which allows for fluid communication between the cylindrical bore 620 and one of the column fittings. The central passage 643 includes a first region 645 that is sized to accommodate a pilot of one of the column fittings, and a second, tapered region 646 to accommodate a needle of one of the column fittings. The retainer 642 may also include a hexagonal or star-shaped counterbore 644 to allow the retainer to be screwed into the second cavity 630 using a tool such as an Allen key. Both end fittings 618 can have the same construction.

Figure 25:
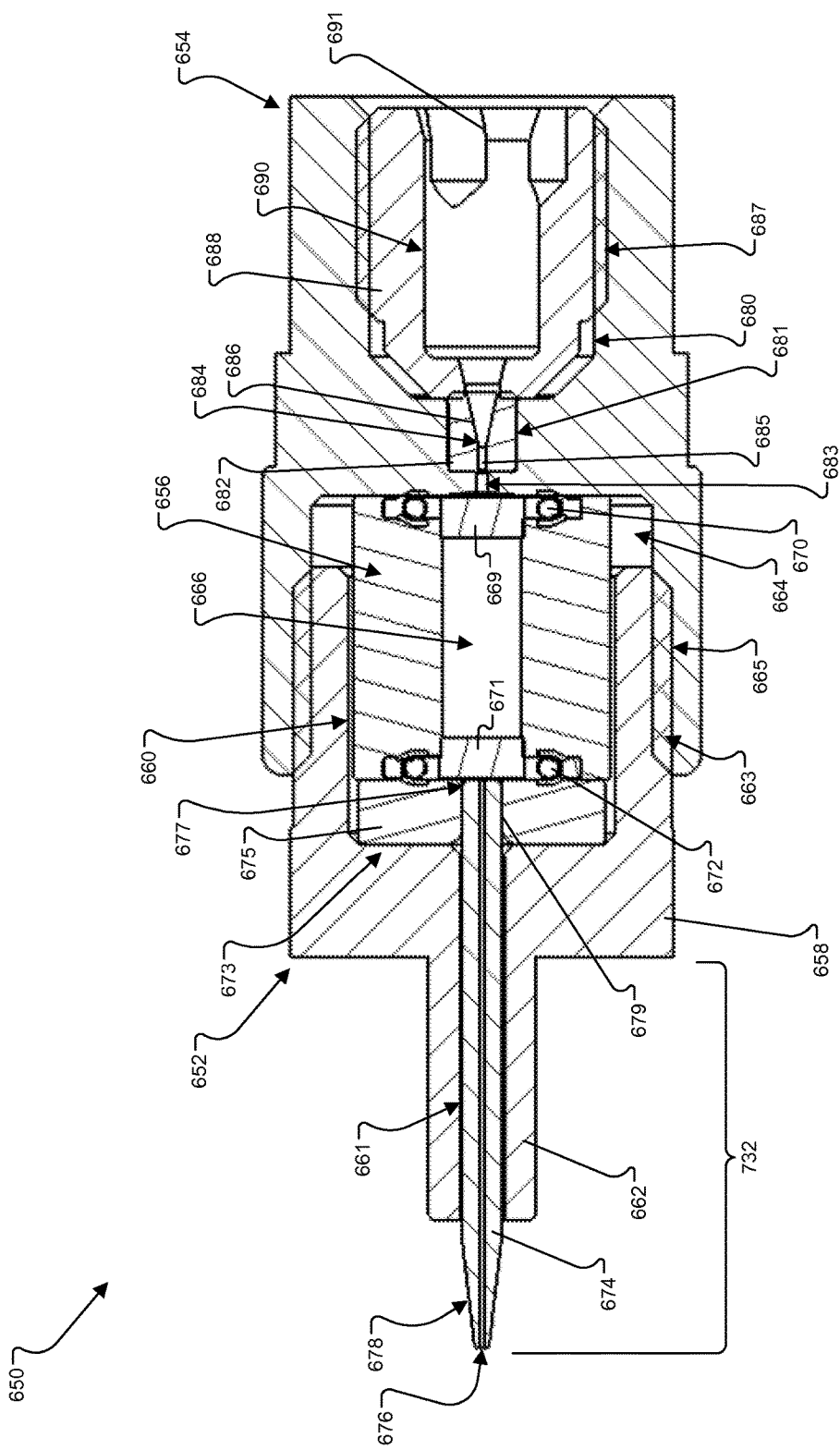
FIG. 25 is a cross-sectional side view of a cartridge sub-assembly, taken along line 25-25 of FIG. 23.

Referring to FIG. 25, the cartridge sub-assembly 650 includes a first member 652, a second member 654, and a cartridge 656 (e.g., a guard cartridge or a filter cartridge) disposed therebetween. The first member 652 includes a cylindrical body 658 which defines a cartridge cavity 660 for receiving the cartridge 656. A cartridge pilot 662 extends outwardly from the cylindrical body 658 and an opening 661 extends through the cartridge pilot 662 and into the cartridge cavity 660. An outer surface of the cylindrical body 658 includes a threaded region 663 which threadingly engages the second member 654. The first member 652 being formed thermoplastic resin, or a metal.

The second member defines a first cavity 664 which includes a threaded portion 665 which mates with the threaded region 663 of the first member 652 to secure the cartridge body 656 within the cartridge cavity 660. The cartridge 656 includes a central bore 666 which extends from a first end of the cartridge 656 to a second, opposite end of the cartridge 656. A first cartridge frit 669, e.g., a porous metal disk, is disposed adjacent the first end of the cartridge 656. A first energized seal 670 surrounds the first cartridge frit 669 and serves to provide a fluid tight seal between the cartridge 656 and the second member 654. A second cartridge frit 671, e.g., a porous metal disk, is disposed adjacent the second end of the cartridge 656. A second energized seal 672 surrounds the second cartridge frit 671 and serves to provide a fluid tight seal between the cartridge 656 and a cartridge needle assembly 673 which is disposed within the cartridge cavity 660 adjacent the second end of the cartridge 656. The second member 654 can be formed thermoplastic resin, or a metal.

The cartridge needle assembly 673 includes a hollow cartridge needle 674 and a base 675. The cartridge needle 674 being formed thermoplastic resin, or a metal. The cartridge needle 674 includes a fluid passage 676 that extends from a first end 677 of the cartridge needle 674 to a tapered, second end 678. The first end 677 of the cartridge needle 674 is mounted within a hole 679 in the base 675. The base 675 can be molded, machined or otherwise formed from a suitable material such as a thermoplastic resin, or metal. The cartridge needle 674 can be secured to the base 675, e.g., by welding, adhesives, press-fit, etc. When installed within the cartridge cavity 660 the tapered end 678 of the cartridge needle 674 extends through the opening 661 and outward from the cartridge pilot 662. The cartridge needle 674 and the cartridge pilot 662 together form a cartridge sub-assembly fitting 732 for establishing a fluidic connection with one of the end fittings 618 on the chromatography column 610.

The second member 654 also defines a second cavity 680 and a seal recess 681 which extends from the second cavity 680 toward the first cavity 664. The seal recess 681 receives a compliant seal 682, which may be formed of polyimide such as DuPont™ Vespel®, polyether-ether-ketone such as PEEK™ polymer (available from Victrex PLC, Lancashire, United Kingdom), or a deformable metal such as annealed stainless steel. A through-hole 683 extends from the first cavity 664 into the seal recess 681 to provide for fluid communication between the central bore 666 of the cartridge 656 and a fluid passage 684 defined by the seal 682. The fluid passage 684 includes a small diameter portion 685 which aligns with the through-hole 683, and a tapered portion 686 which extends from an interface with the small diameter portion 685 to an opposite end of the seal 682. The tapered portion 686 has an included angle of less than 40 degrees. The second cavity 680 defines a threaded region 687 which threadingly receives a retainer 688 for retaining the seal 682 within the seal recess 681. As with the end fittings 618 discussed above, this threaded arrangement allows the retainer 688 to be removed for replacing the seal 682 when and if it becomes worn or damaged. The retainer 688 is threaded into the second cavity 680 and includes a central passage 690 which accommodates the inlet column fitting 512. The retainer 688 may also include a hexagonal or star-shaped counterbore 691 to allow the retainer to be screwed into the second cavity 680 using a tool such as an Allen key.

Figure 26:
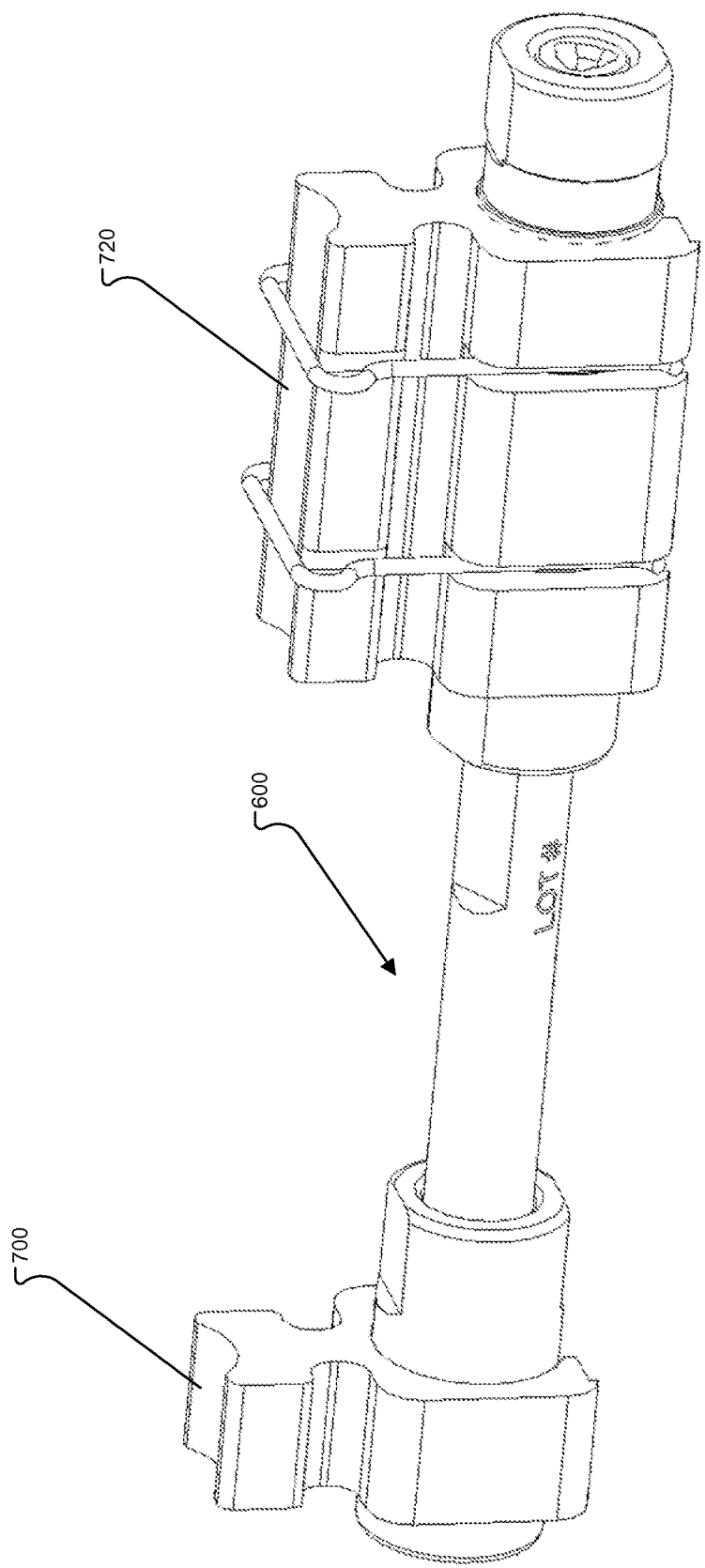
FIG. 26 is an isometric view of a column assembly including a column clip and a retainer clip.

Referring to FIG. 26, a column clip 700 and retainer clip 720 are provided for handling the column assembly 600. These clips 700, 720 can be used, for example, to insert the column assembly 600 into the clamp assembly 300 within the trough 128, and also for removing the column assembly 600 from the clamp assembly 300, e.g., for replacement. These clips 700, 720 also function to keep the column assembly 600 from directly contacting the heated trough 128, and help to align the column assembly 600 in position up, down and centered within the trough 128. The clips 700, 720 include a column clip 700 and a retainer clip 720.

Figure 27:
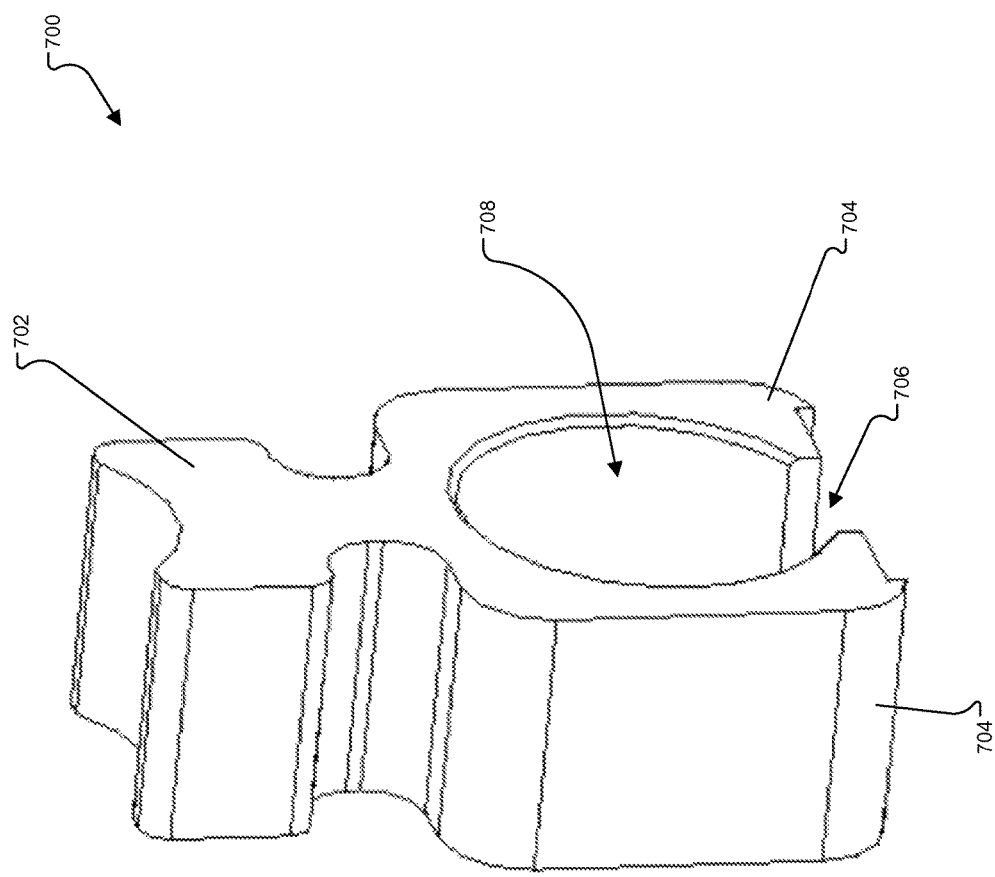
FIG. 27 is an isometric view of the column clip.

As shown in FIG. 27, the clip 700 generally includes a handle 702 and a pair of arcuate arms 704 which extend from the handle 702 and terminate at an open end 706. The arcuate arms 704 define a cylindrical central opening 708 sized to fit about the end fittings 618 of the column 610. The column clip 692 can be molded, machined or otherwise formed from a suitable material such as a thermoplastic resin, or metal.

Figure 28:
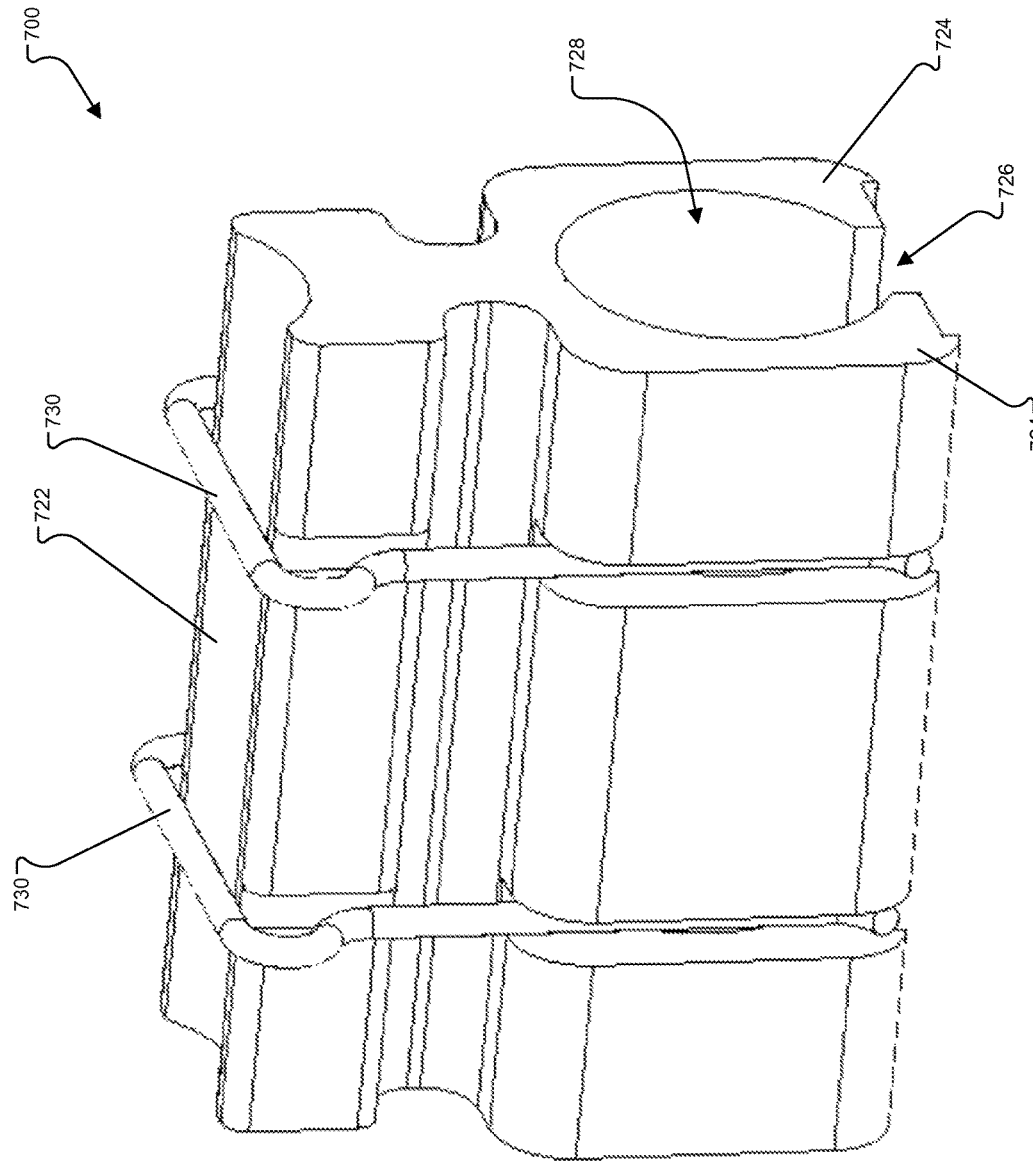
FIG. 28 is an isometric view of the retainer clip.

Referring to FIG. 28, the retainer clip 720 generally includes a handle 722 and a pair of arcuate arms 724 which extend from the handle 722 and terminate at an open end 726. The arcuate arms 724 define a cylindrical central opening 728 sized to fit about the end fitting 618 and the second member 654 of the cartridge sub-assembly 650. The handle 722 and arcuate arms 724 being molded, machined or otherwise formed from a suitable material such as a thermoplastic resin, or metal. The retainer clip 720 also includes a pair of spring elements 730 that maintain the cartridge sub-assembly 650 in place next to the column 610. In this regard, the spring elements 730 allow the cartridge subassembly 650 to slide slightly relative to column 610, but limit its travel to inhibit (e.g., prevent) the cartridge subassembly 650 from falling away during column loading and unloading. In situations in which no cartridge sub-assembly or filter is utilized, a second column clip 700 can be utilized at the inlet end of the column 610.

Figure 29A:
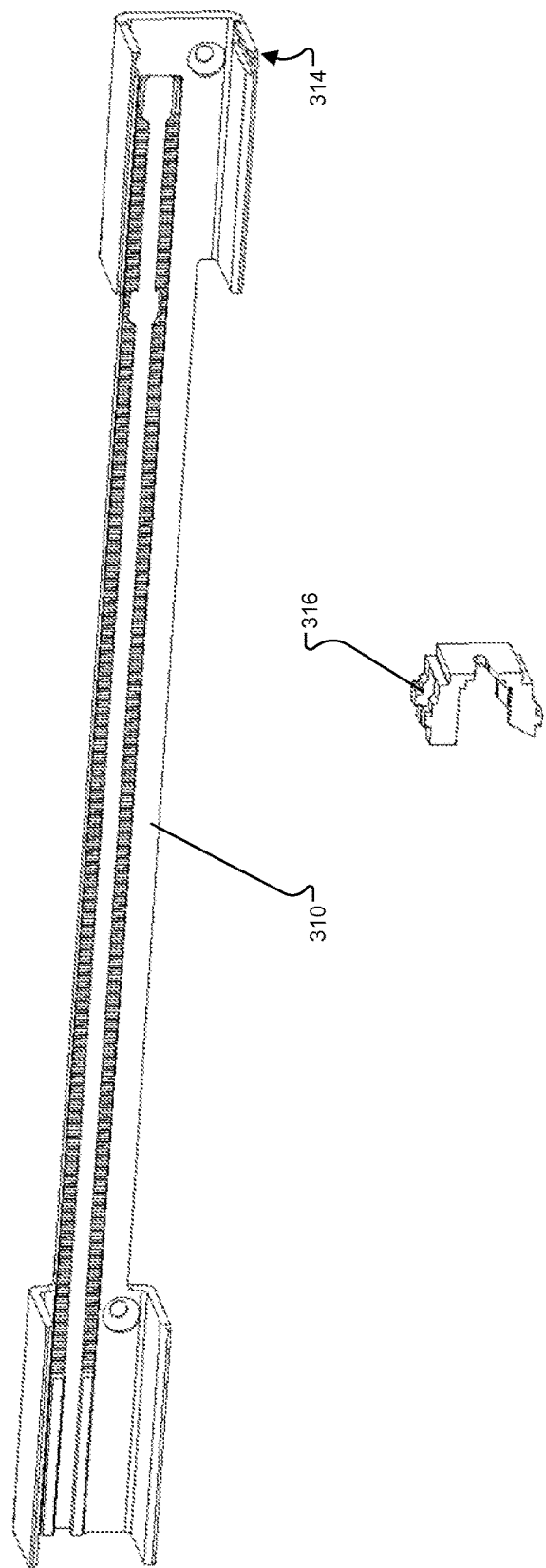
FIGS. 29A-29T illustrate sequential views showing one embodiment of assembly of the fluidic coupling apparatus into the thermal module.
Figure 29B:
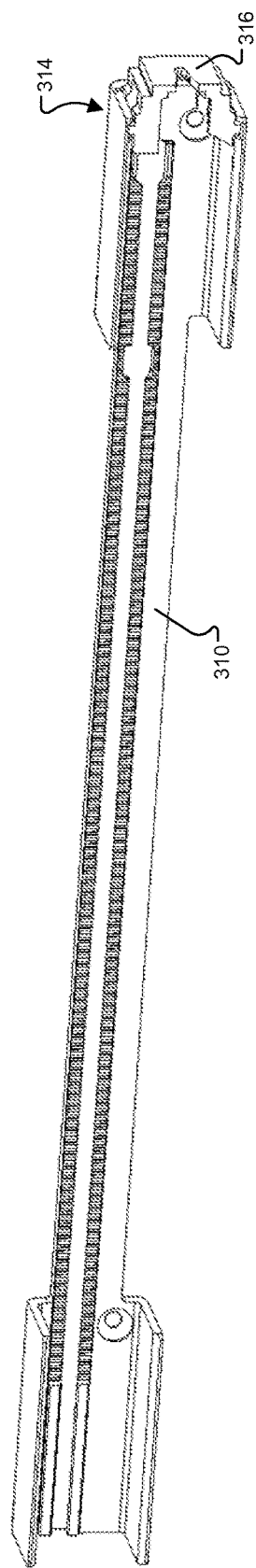
Figure 29C:
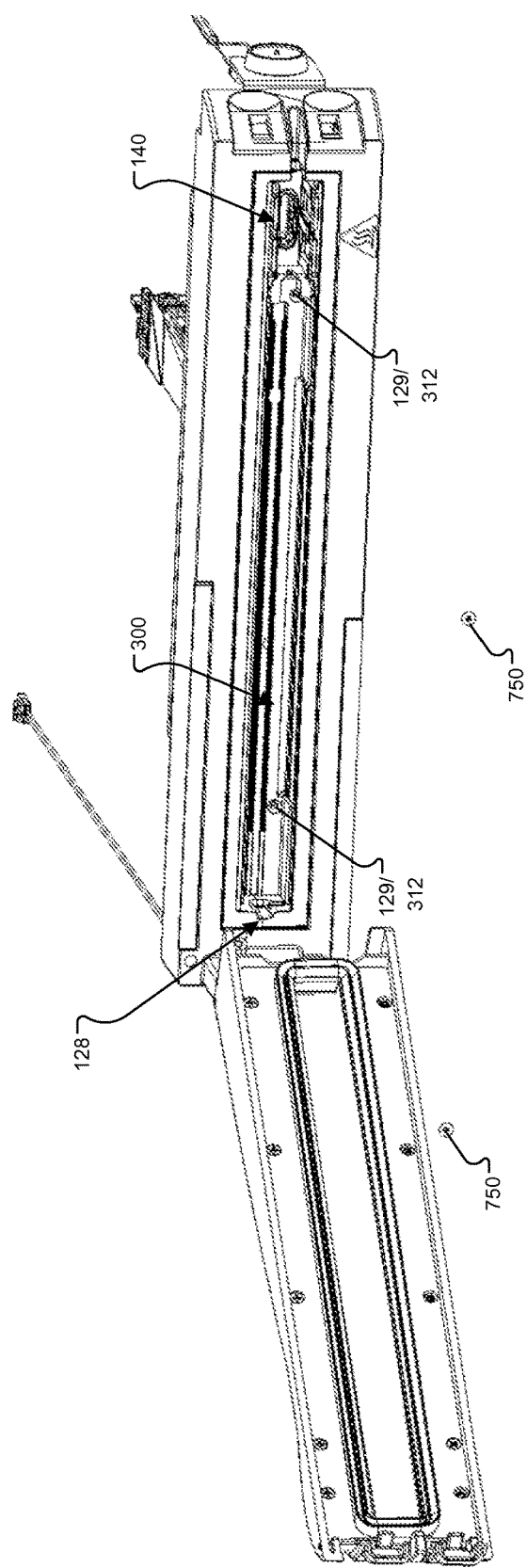
Figure 29D:
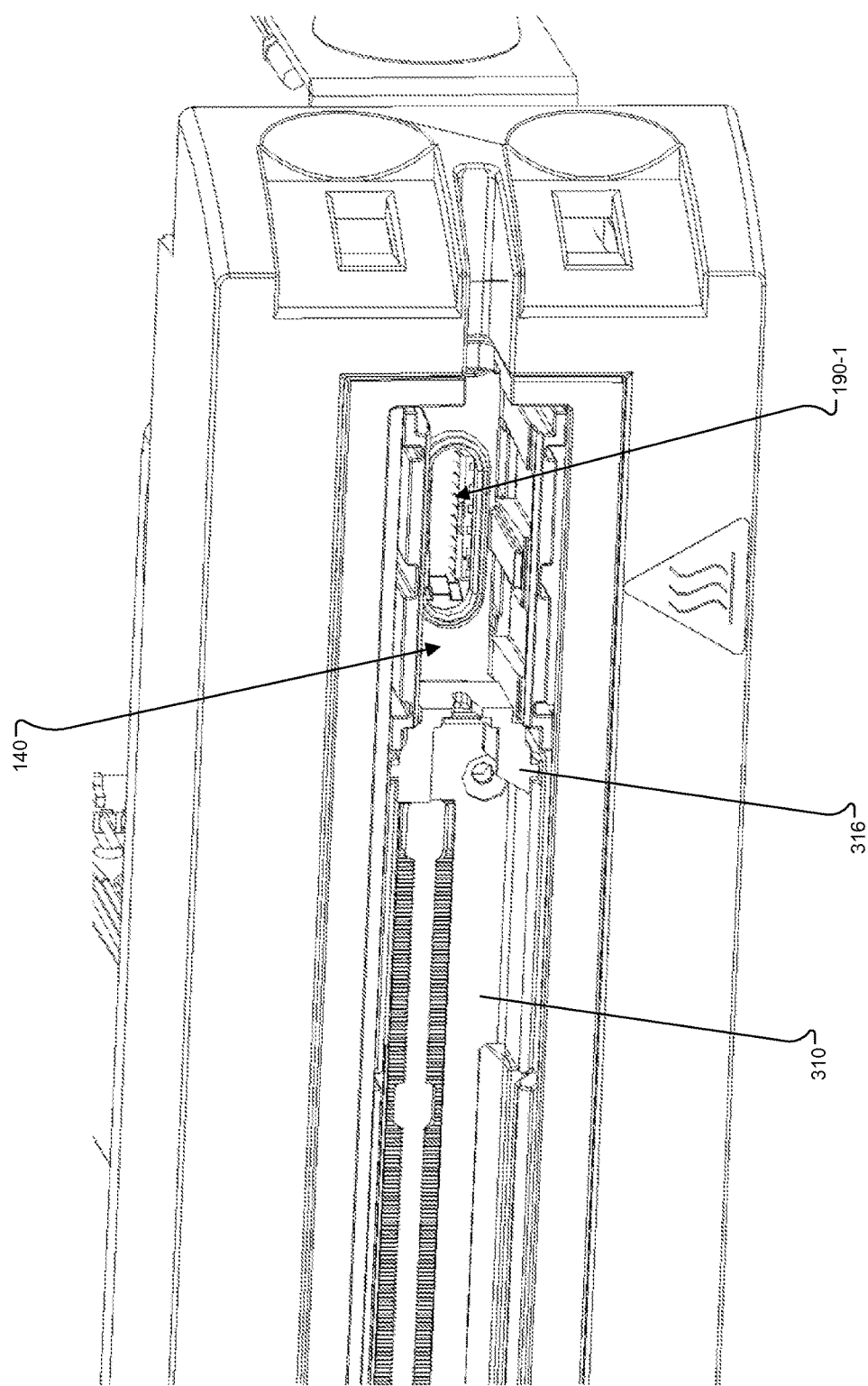

In use, the rail end cap 316 is installed by sliding and clicking the rail end cap 316 into a recess at the distal end 314 of the rail 310 (as illustrated in FIGS. 29A & 29B). The rail 310 is then inserted into the trough 128 by securing the rail 310, with fasteners 750 to mounting holes 129 located in either end of the trough 128, as illustrated in FIG. 29C. As shown in FIG. 29D, once the rail 310 is mounted in the trough 128, the rail end cap 316 aligns with the active pre-heater receptacle 140.

Figure 29E:
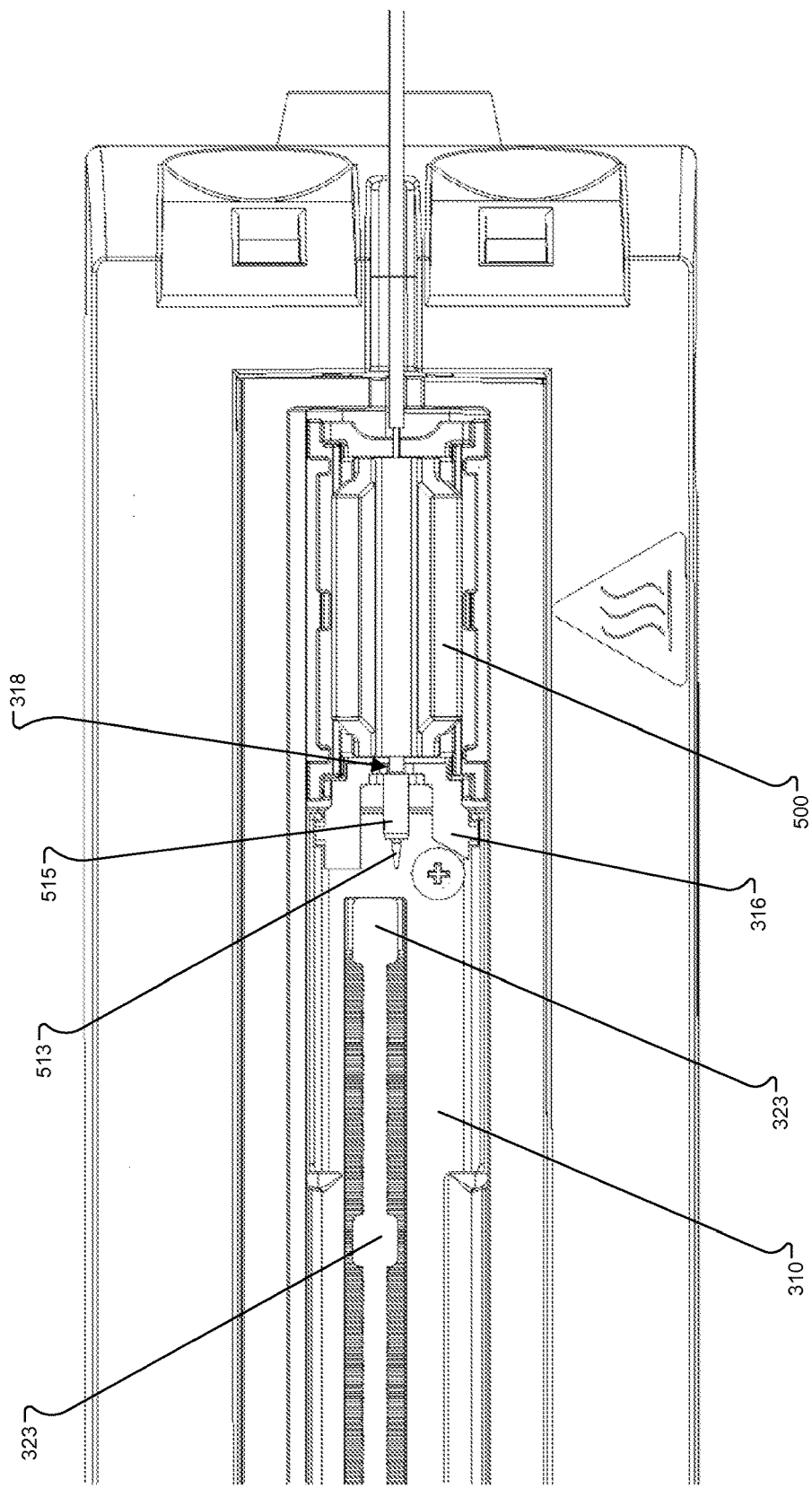

Next, the active pre-heater assembly 500 is plugged into the exposed one of the sockets 190-1, 190-2 (generally 190) at the end of the trough 128. (Note: the fluidic coupling apparatus installation may be reversed to reverse flow direction through the trough 128; i.e., such that the active pre-heater assembly 500 engages electrical socket 190-2 near the hinge 64). As shown in FIG. 29E, once the active pre-heater assembly 500 is installed in the socket 190, the inlet pilot 515 is received within the fitting recess 318 of the rail end cap 316.

Figure 29F:
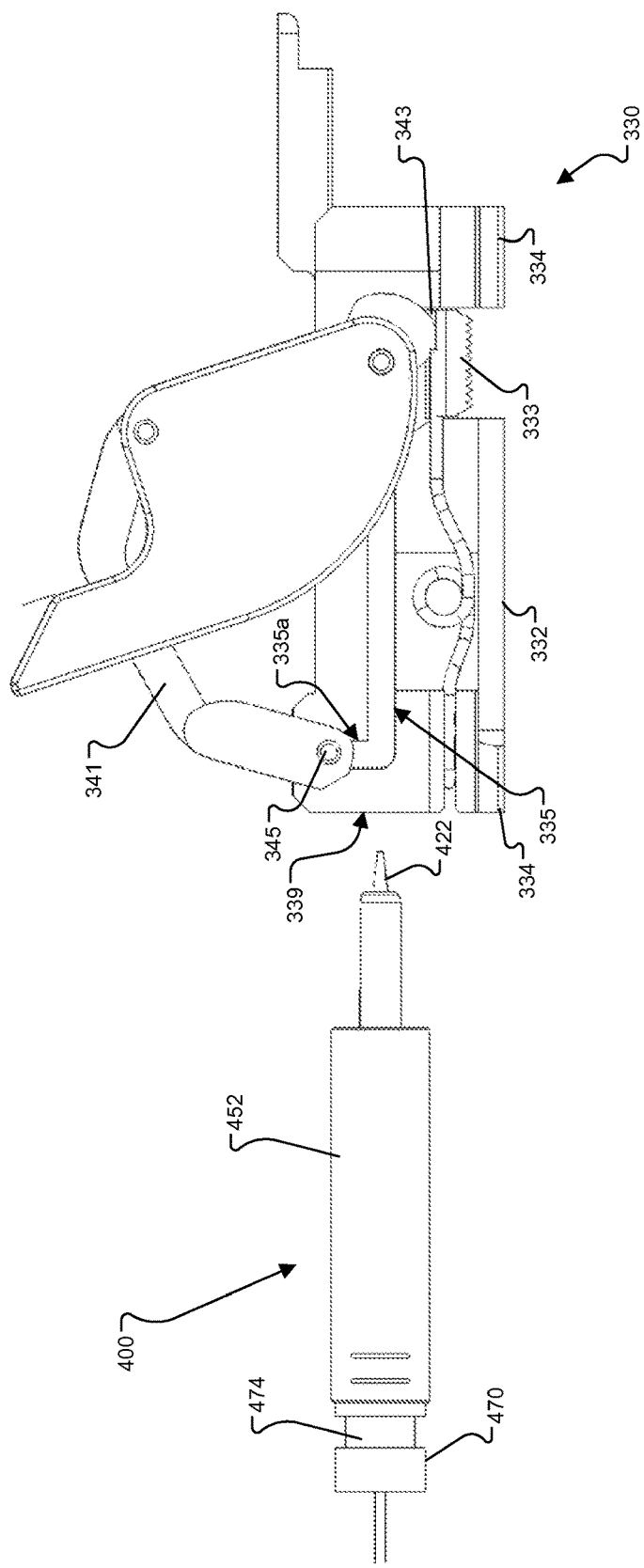
Figure 29G:
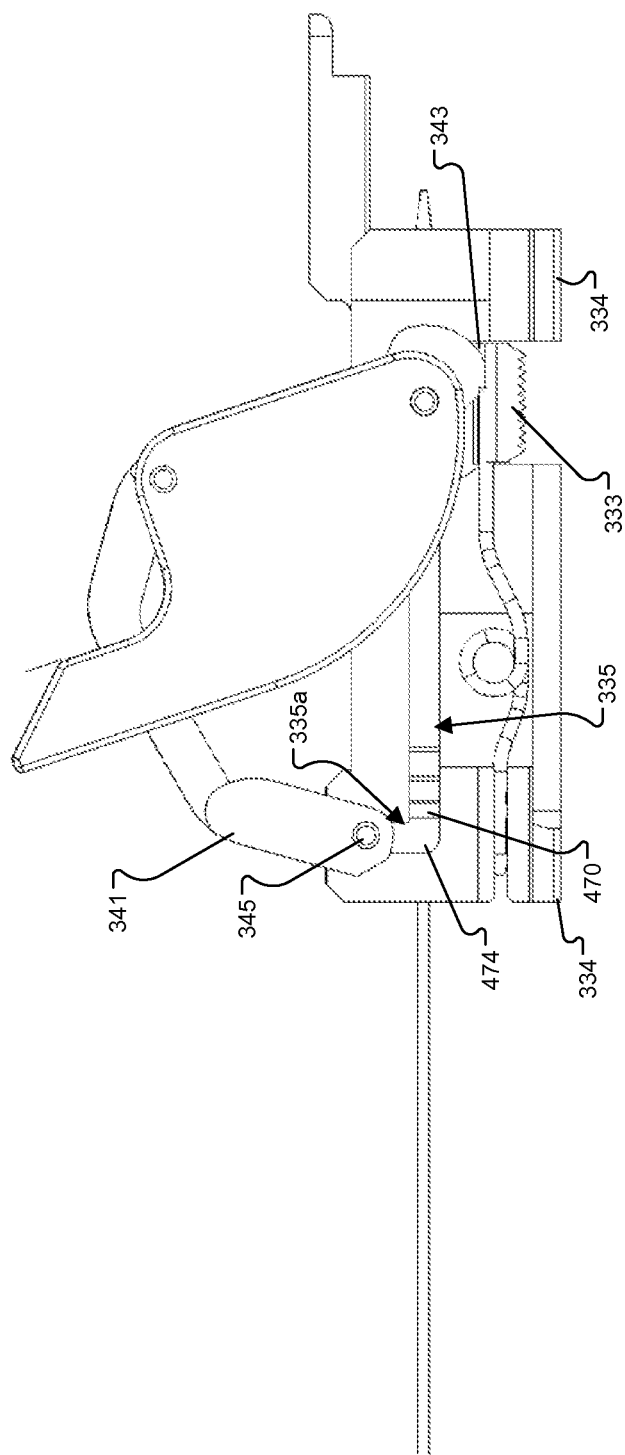
Figure 29H:
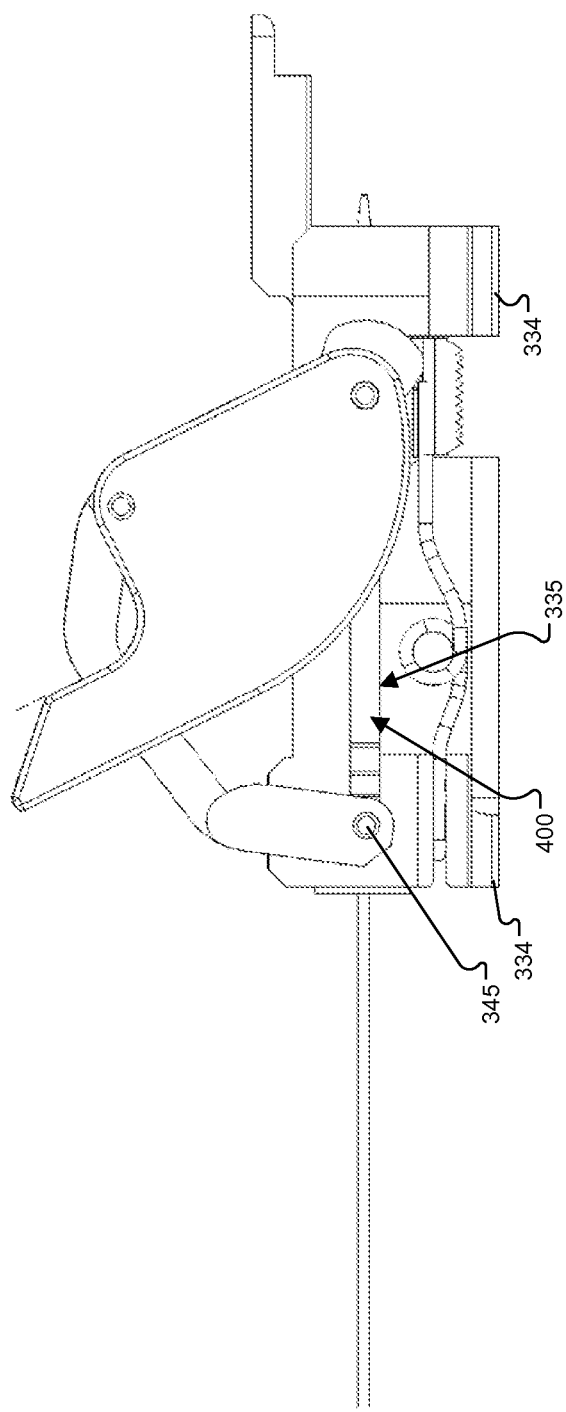

Next, the needle barrel assembly 400 is assembled into the carriage 330. In this regard, the needle barrel assembly 400 is inserted, outlet needle 422 first, into the cylindrical bore 339 in the carriage body 332. As shown in FIG. 29F, the pins 345 of the arm 341 are positioned up in the vertical segment 335a of the slot 335 to allow insertion of the needle barrel assembly 400. The needle barrel assembly 400 is slid forward into the cylindrical bore 339 until the distal end of the outer barrel 452 abuts against the upwardly extending protrusion 343 on the foot 333. In this position, an annular recess 474 in the outer spring retainer 470 will be aligned with the vertical segment 335a of the slot 335 and positioned to receive the pins 345 on the arm 341, as shown in FIG. 29G. The pins 345 slide down the vertical segment 335a of the slot 335 and are received in annular recess 474, as shown in FIG. 29H, for controlling movement of the needle barrel assembly 400 relative to the clamp assembly 300.

Figure 29I:
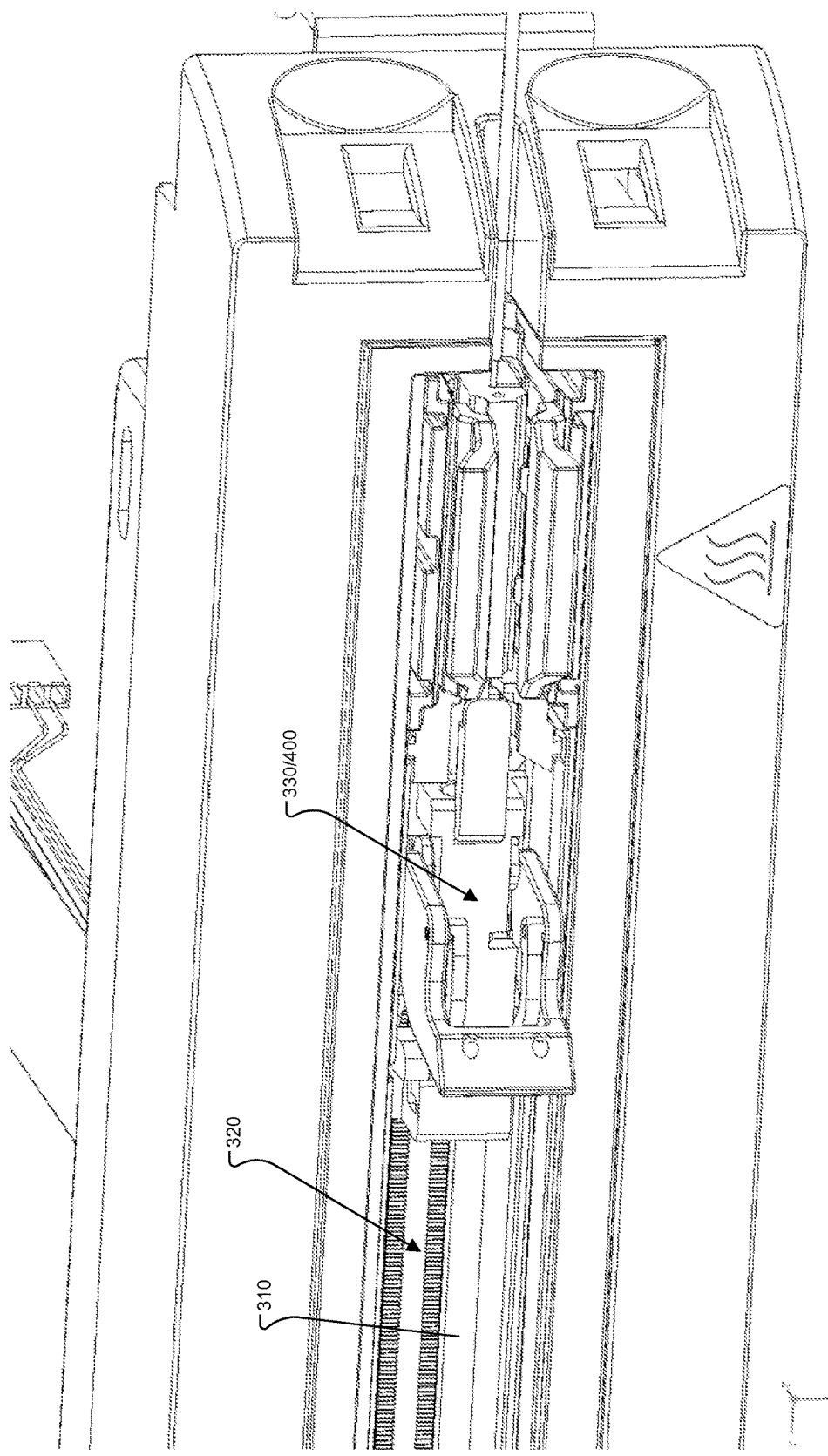
Figure 29J:
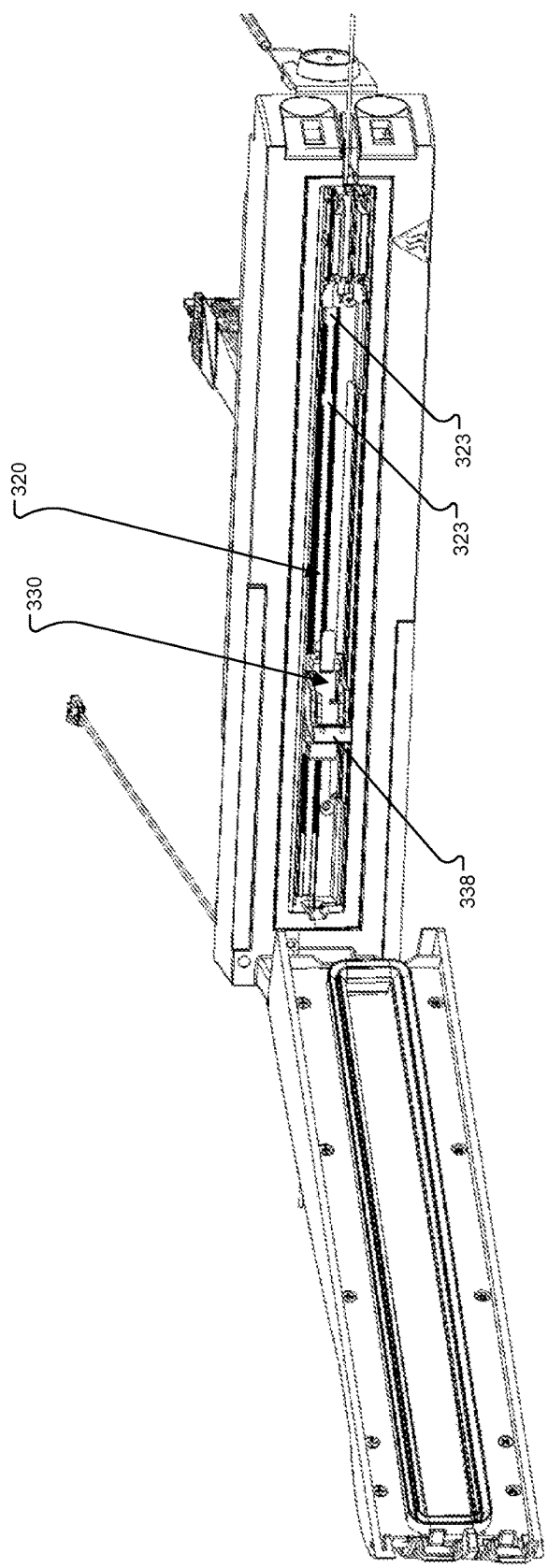

The assembled carriage 330 and needle barrel assembly 400 is then inserted into the rail 310 by inserting the dovetail projections 334 (FIGS. 9A & 29H) into the slots 323 (FIGS. 8 & 29E) in the rail 310, as shown in FIG. 29I, and then displacing the carriage 330 such that the dovetail projections 334 slide within the dovetail groove 320, as shown in FIG. 29J. The carriage 330, with the lever 338 of in the disengaged position, is moved to the appropriate position within the clamp assembly 300 for the length of column being used. The clamp assembly 300 may be configured to receive columns with inside diameters of 1.0, 2.1, 3.0 and 4.6 mm and lengths of 30, 50, 75, 100 and 150 mm.

Figure 29K:
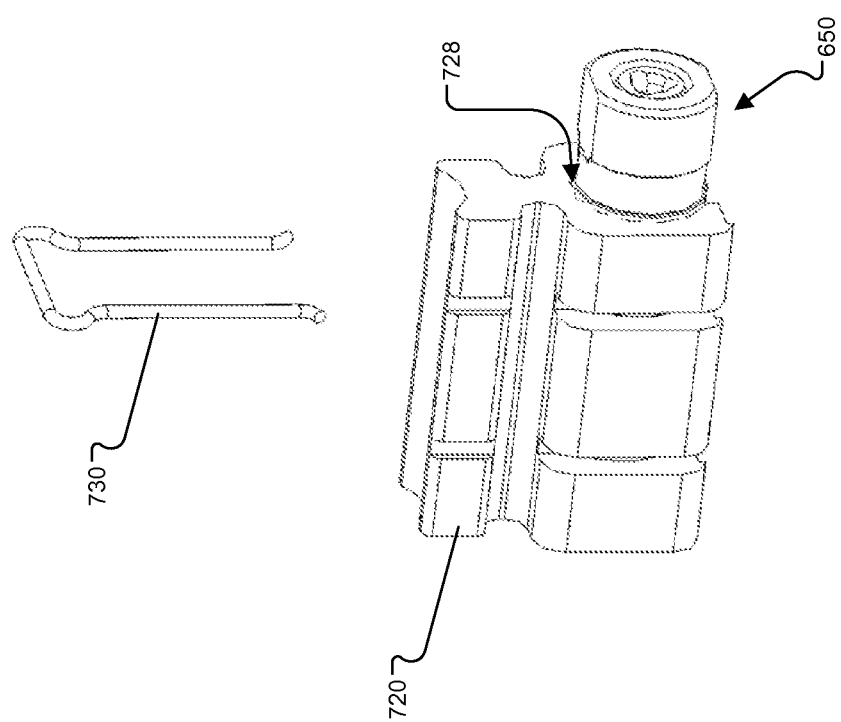
Figure 29M:
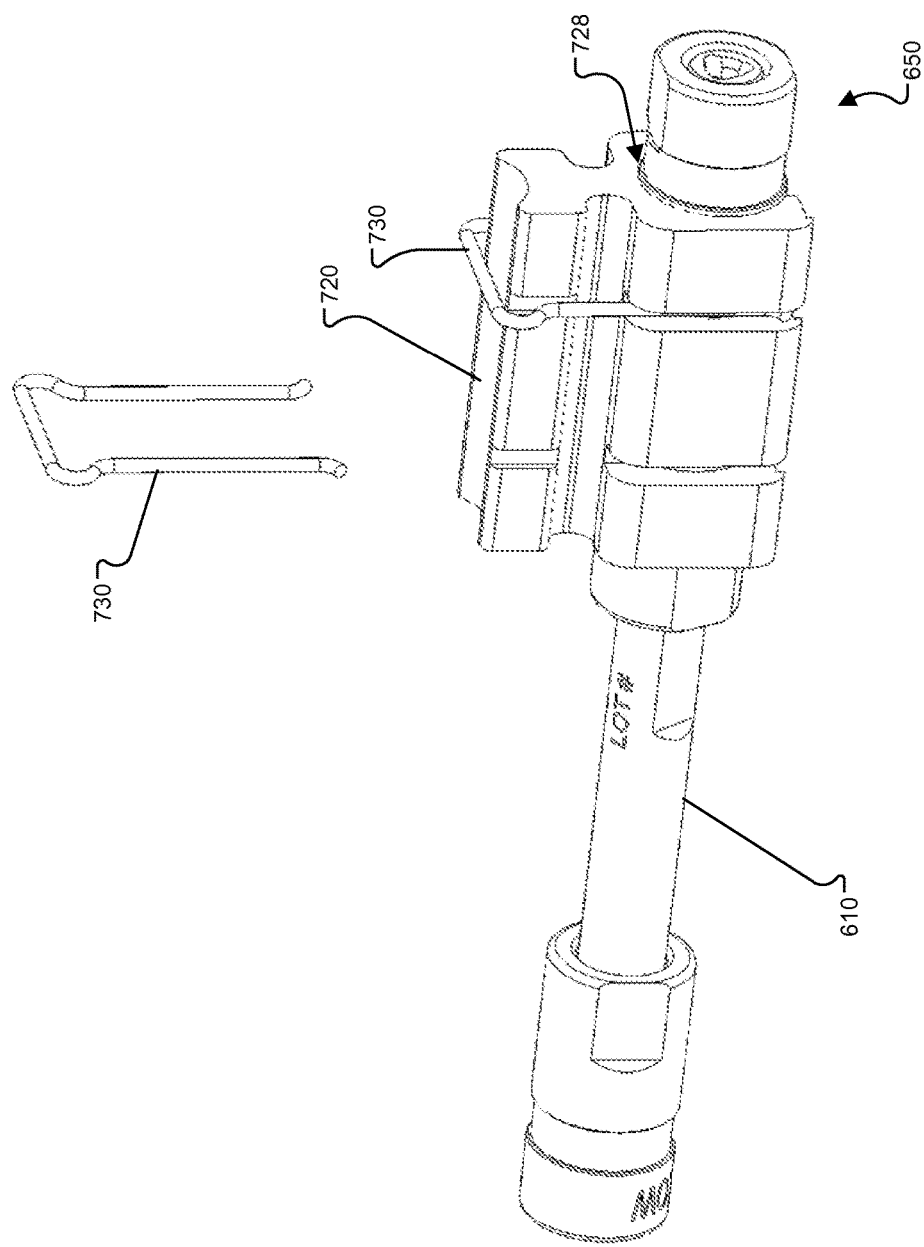

Next, the clips 700, 720 are attached to either end of the chromatography column 610 and to the cartridge sub-assembly 650 (if used), and are used to position and aid insertion of the chromatography column 610 and the cartridge sub-assembly 650 within the clamp assembly 300. The retainer clip 720 is attached to the cartridge sub-assembly 650 by inserting the cartridge sub-assembly 650, cartridge needle 674 (FIG. 25) first, into the cylindrical central opening 728 in the retainer clip 720, as shown in FIG. 29K. A first one of the spring elements 730 is then secured into place to retain the cartridge sub-assembly 650 within the cylindrical central opening 728, as shown in FIG. 29L. Then, the inlet end of the chromatography column 610 is inserted into the opposite, open end of the cylindrical central opening 728 in the retainer clip 720, and a second one of the spring elements 730 is secured in place to retain the inlet end of the chromatography column 610 within the central opening 728, as shown in FIG. 29M.

Figure 29N:
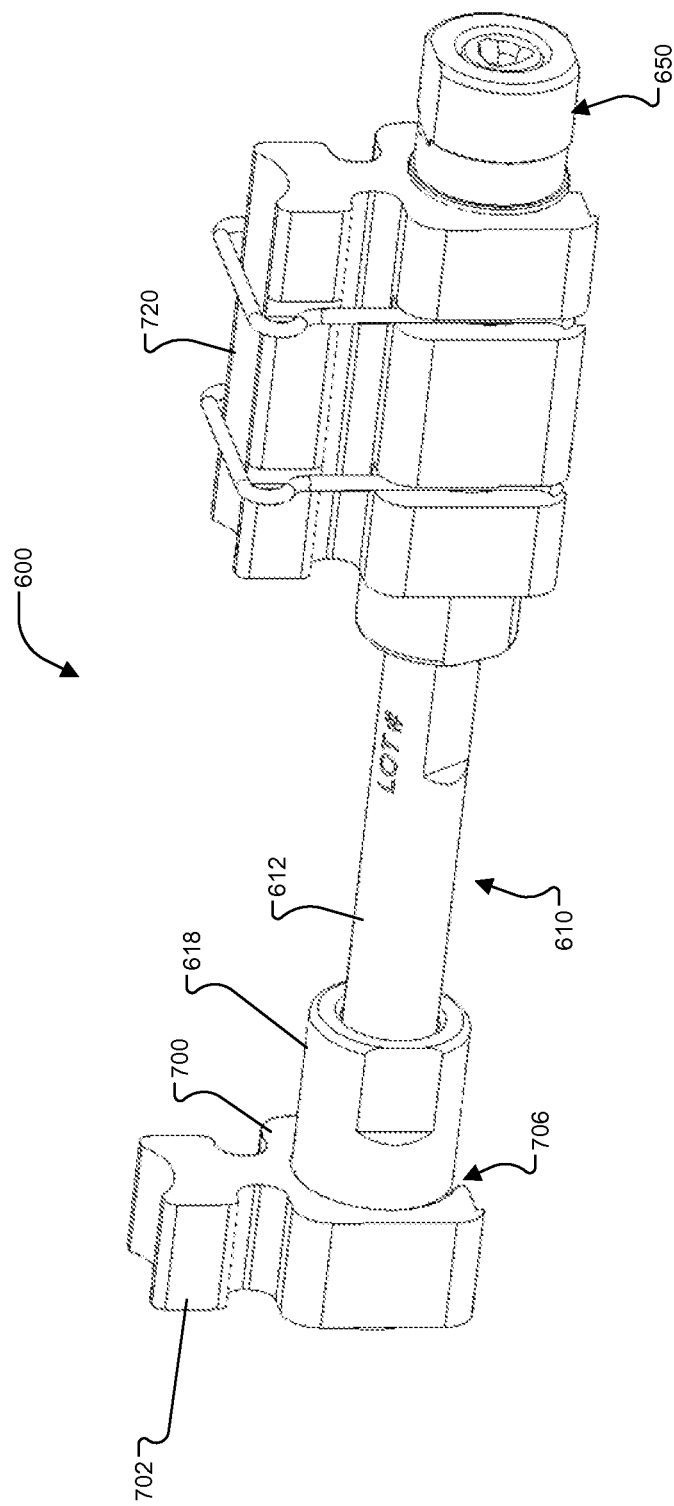

The column clip 700 is connected to the outlet end of the chromatography column 610 by placing the open end 706 of the clip 700 about the elongate body 612 of the chromatography column 610 such that the elongate body 612 is substantially coaxial with the cylindrical central opening 708. The handle 702 can then be displaced axially along the elongate body 612 into position about the end fitting 618 at the outlet end of the chromatography column 610, as shown in FIG. 29N.

Figure 29O:
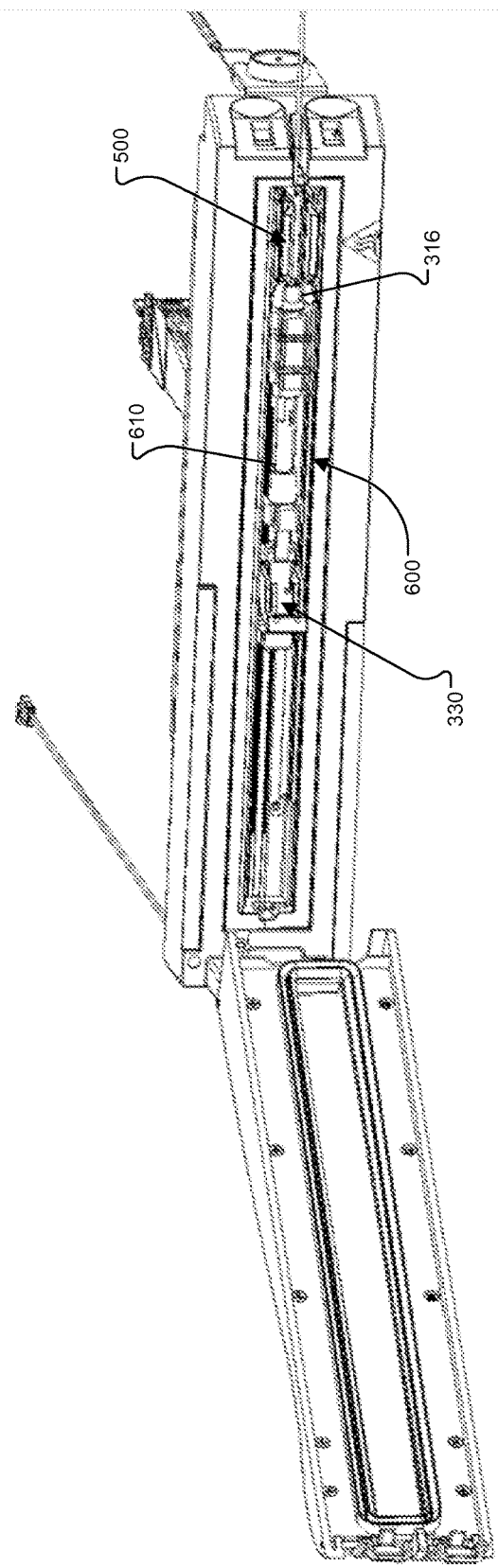
Figure 29P:
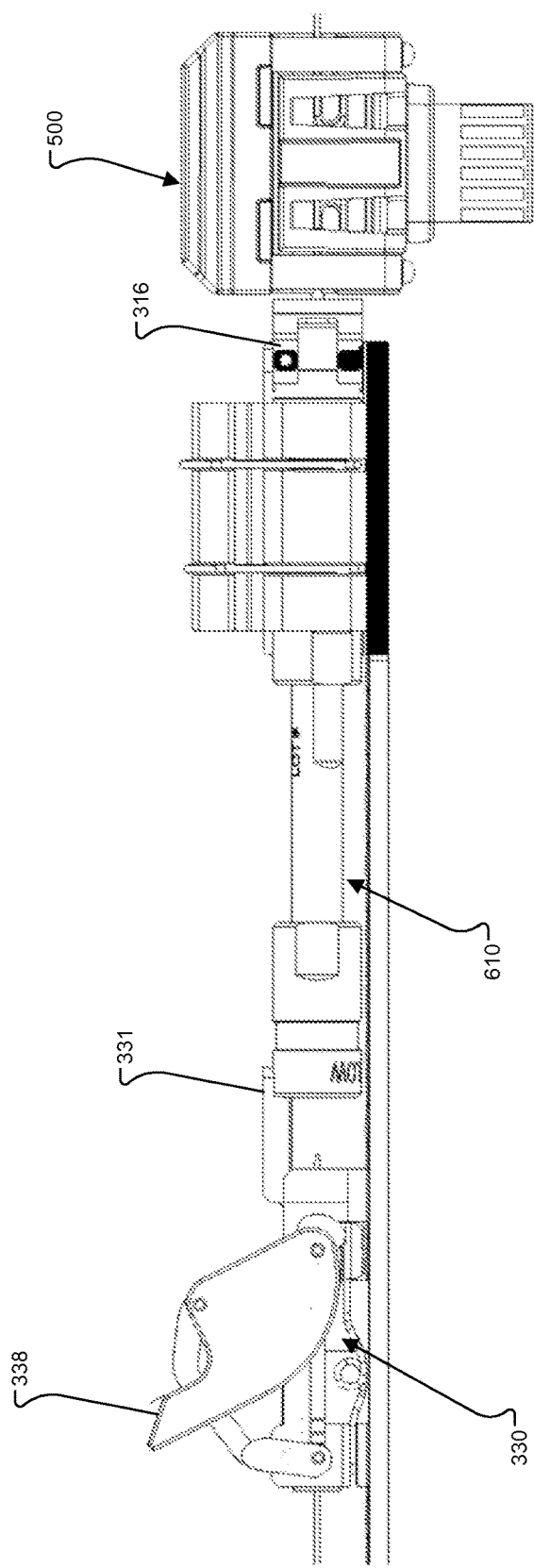

Next, the column assembly 600 is inserted between the carriage 330 and the rail end cap 316, as shown in FIG. 29O, and is slid towards the active pre-heater assembly 500, such that the inlet needle 513 (FIG. 29E) enters the central passage 690 (FIG. 25) of the cartridge sub-assembly 650. The carriage 330 is then slid towards the chromatography column 610 until the stop feature 331 contacts the outlet end of the chromatography column 610, as shown in FIG. 29P (the column-heater enclosure 16 and the column clip 700 have been removed for clarity).

Figure 29Q:
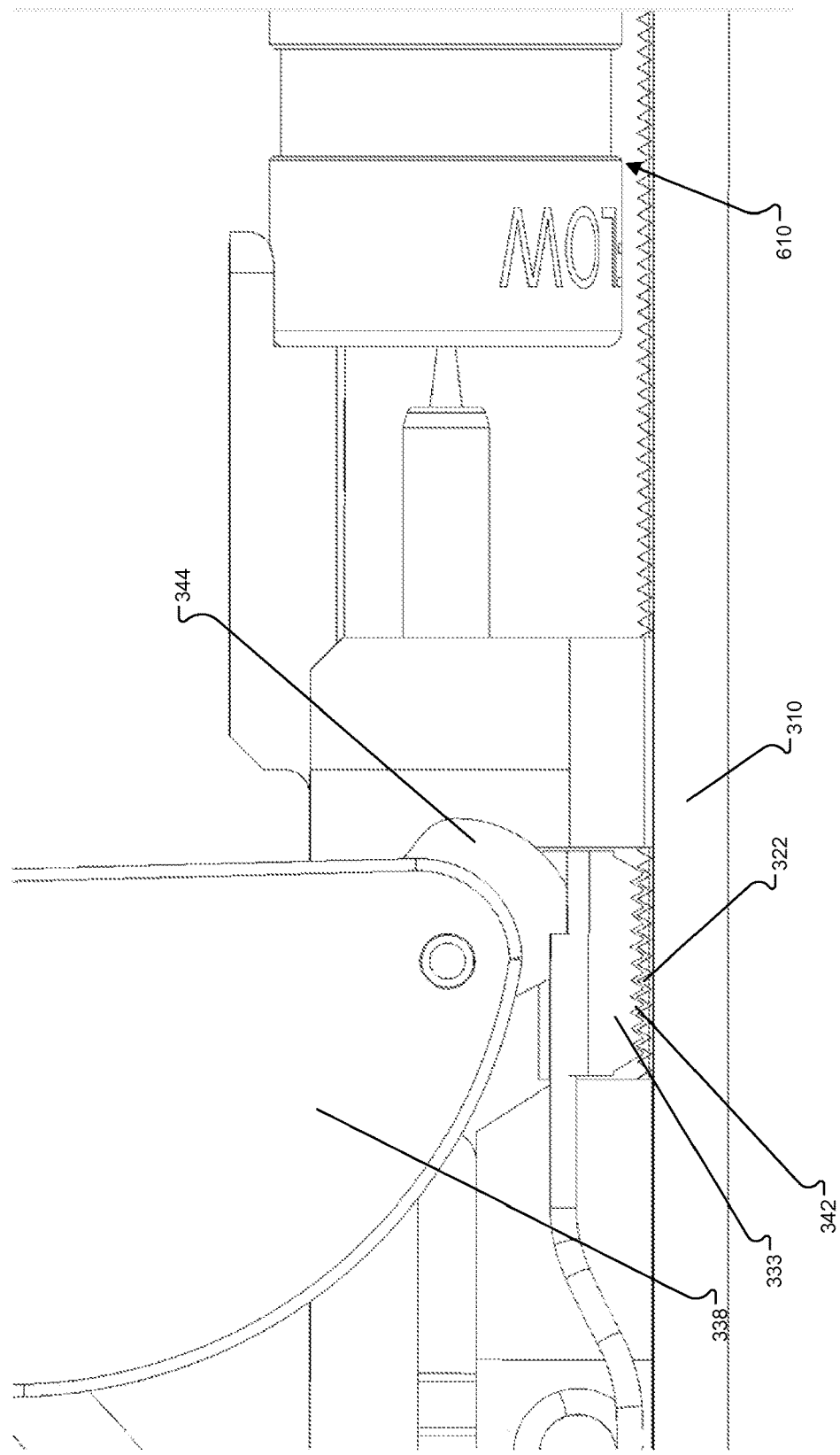
Figure 29R:
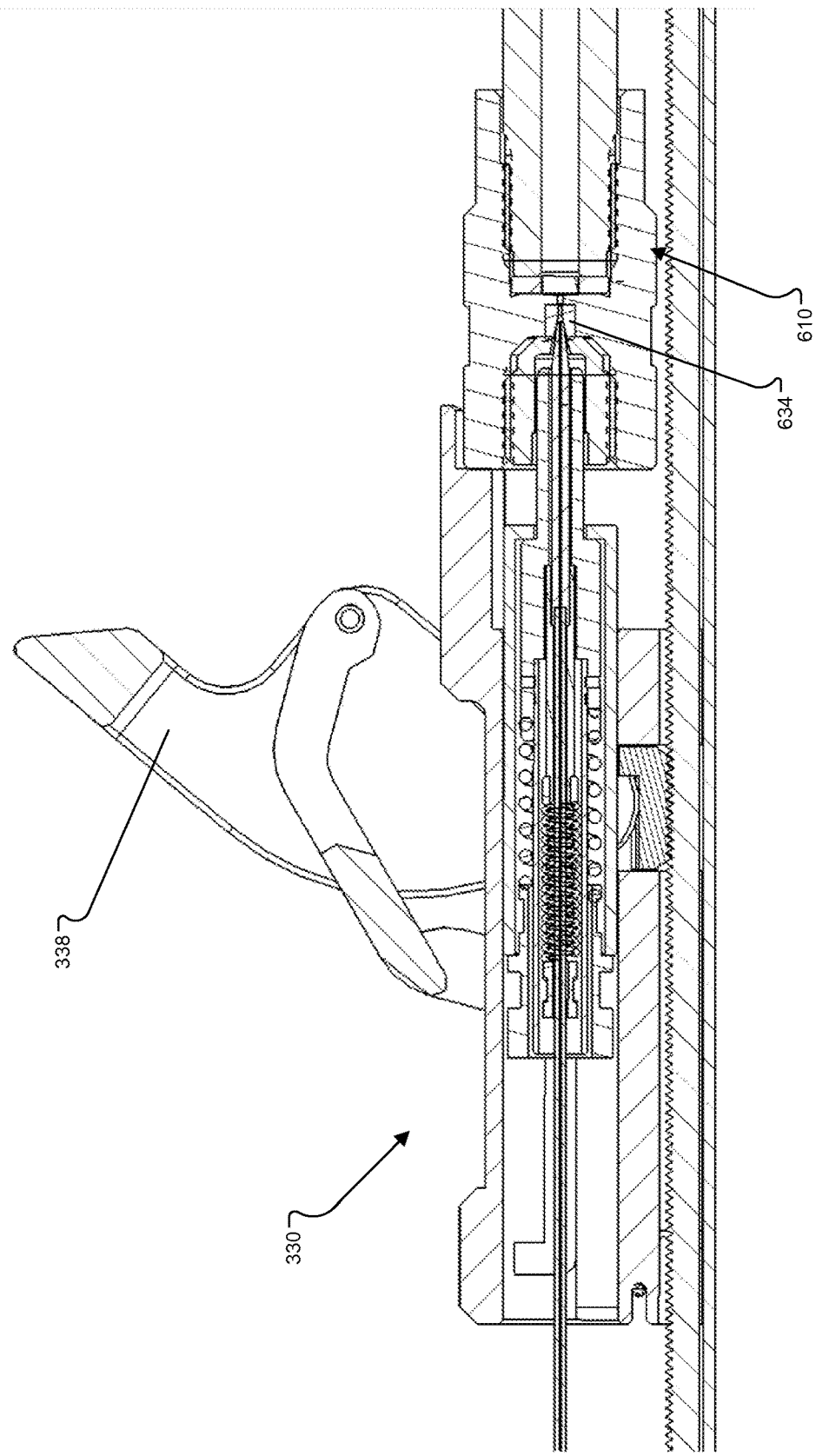

Once the column assembly 600 and the carriage 330 are so positioned, the lever 338 is displaced from the disengaged position (shown, for example, in FIG. 29P) toward the engaged position. As illustrated in FIG. 29Q, when the lever 338 starts to rotate between positions, the cam 344 displaces the foot 333, thereby pushing the teeth 342 of the foot 333 into engagement with the teeth 322 of the rail 310. The lever 338 continues to rotate to cause the barrel assembly to transition toward the seal 634 at the outlet end of the chromatography column 610, as shown in the cross-sectional side view of FIG. 29R.

Figure 29S:
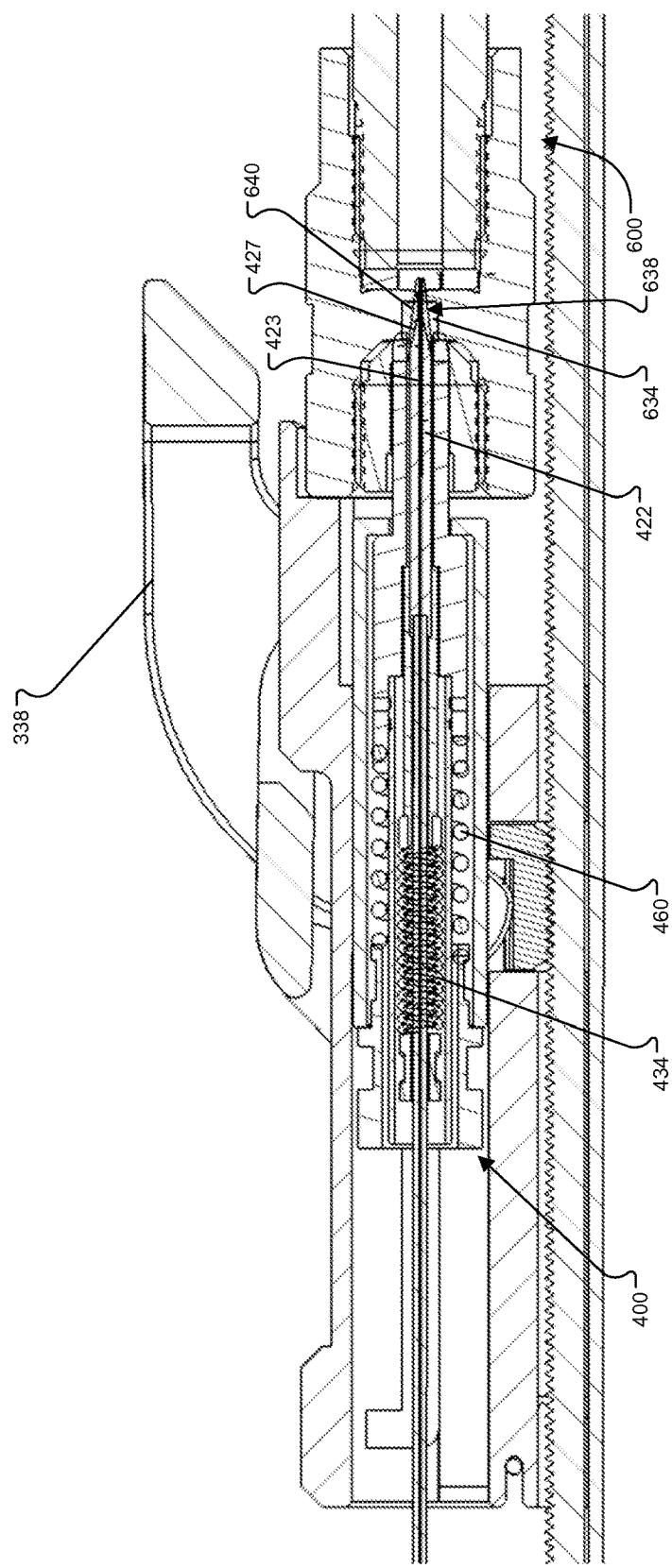

With reference to FIG. 29S, the lever 338 is further rotated toward the fully engaged position such that the fluid passage 423 of the outlet needle 422 aligns with the fluid passage 638 of the seal 634 and such that the tapered end 427 outlet needle 422 contacts the tapered portion 640 of the seal 634 at the outlet end of the chromatography column 610 to form a fluid tight seal (e.g., up to 20,000 psi) therebetween. The tapered end of the needle mates with the tapered portion 640 at a diameter less than 0.030 inches. Unlike conventional fitting connections, which typically rely on a ferrule to establish a fluid tight seal, the fluid tight seal provided at the tapered end of the needle is just outside the fluid path's outer diameter so that it may be as small and tight as possible. This can help to eliminate dead volume and minimize seal force. The inner spring 434 assists with biasing the outlet needle 422 towards the seal 634, thereby reducing dead volume, and helps to accommodate for dimensional tolerances. The load provided by the inner spring 434 of the needle barrel assembly 400 establishes the contact, sealing force with the outlet end of the column assembly 600.

Figure 29T:
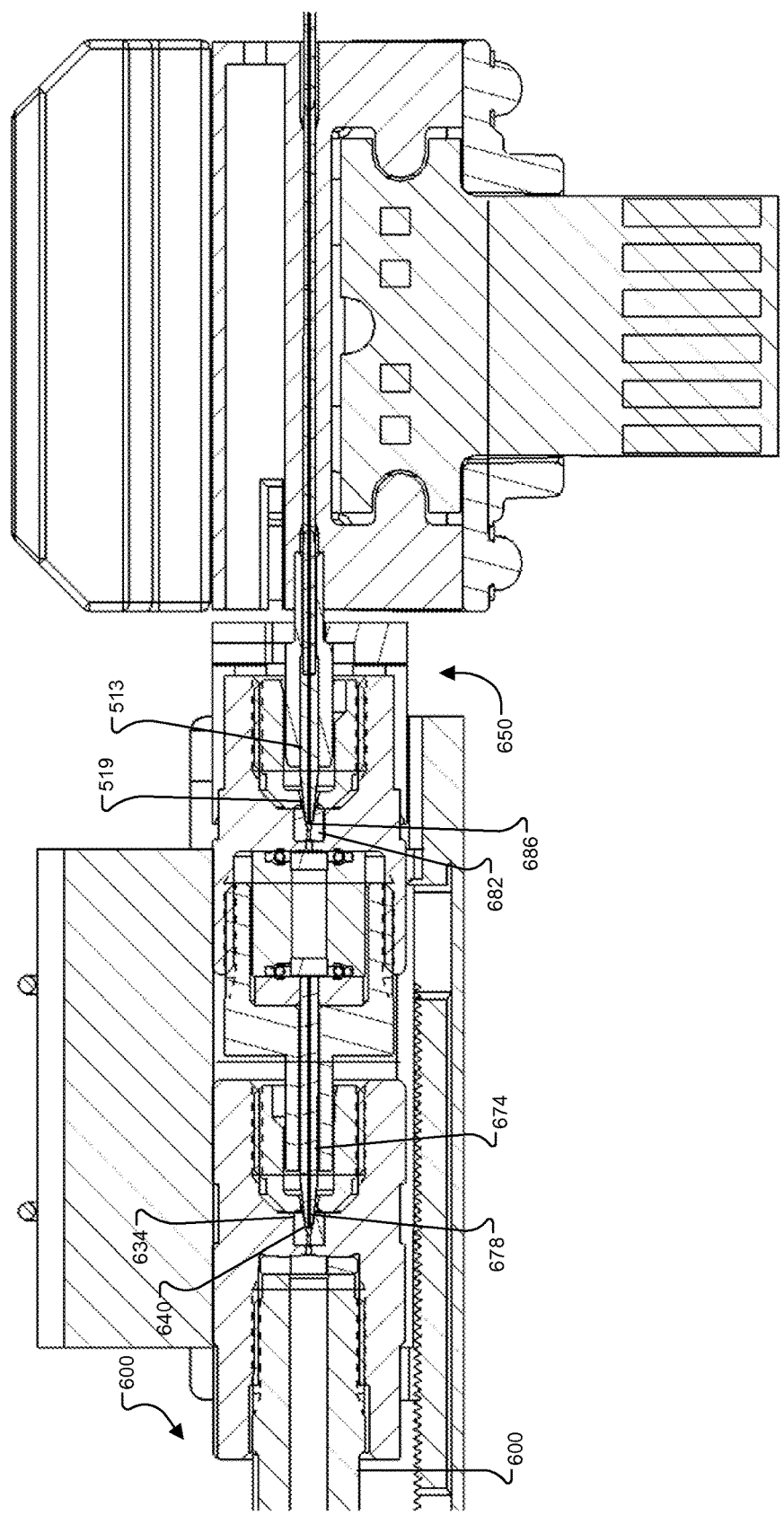

The rotation of the lever 338 into the engaged position also establishes the fluidic seals at the opposite, inlet end of the column assembly 600. That is, referring to FIG. 29T, the rotation of the lever 338 into the engaged position also establishes the fluidic seal between the tapered end 678 of the cartridge needle 674 and the tapered portion 640 of the seal 634 at the inlet end of the chromatography column 610, and the fluidic seal between the tapered end 519 of the inlet needle 513 and the tapered portion 686 of the seal 682 in the cartridge sub-assembly 650. Once again, fluid tight seals are established just outside the fluid path's outer diameter, at the tapered ends of cartridge needle 674 and the inlet needle 513, so that those seals may be as small and tight as possible. This can help to eliminate dead volume and minimize seal force. The load provided by the outer spring 460 (FIG. 29S) of the needle barrel assembly 400 establishes the contact, sealing forces at the inlet end of the column assembly 600 allowing the sealing forces at the inlet and outlet ends of the column assembly to 600 to be independent of each other.

As a result, fluid connections between the chromatography column 610, the cartridge sub-assembly 650, and the inlet and outlet capillary tubing 504, 410 are established and maintained via operation of the lever 338. The fluidic coupling apparatus 200 is capable of running at pressures of up to 20,000 pounds per square inch. This configuration can help to ensure repeatability of connection. This configuration can also help to ensure ease of connection, and helps to provide a fluid connection which does not require highly skilled operators to ensure that the connection is properly established. In addition, less mechanical force may be required to establish the fluid connections as compared to conventional threaded fittings or bayonet fittings which require application of torque, e.g., by hand alone or with the use of tools, to establish a fluid tight connection.

Although a few implementations have been described in detail above, other modifications are possible. For example, in some implementations, the distal end of the carriage body may also include a layer of compliant material in the region below the stop feature. The use of the compliant material can help to alleviate stress on fluid seals in situations in which the teeth on the foot of the carriage do not line up precisely with the teeth on the rail such that, as the foot is displaced into engagement with the rail (via operation of the level), the interaction between the teeth on the foot of the carriage and the teeth on the rail causes the carriage itself to displace slightly toward the column assembly.

In certain implementations, adapters can be provided for converting chromatography columns with conventional ferrule type fitting connections.

Although a clamp assembly has been described for use in a thermal module, in some implementations, the clamp assembly may alternatively or additionally be configured for use in a column manager, such as the ACQUITY UPLC Column Manager available from Waters Corporation of Milford Mass.

Accordingly, other implementations are within the scope of the following claims.

What is claimed is:

1. A clamp assembly comprising:
    a rail configured to receive a first fluidic assembly; and
    a carriage including a carriage body, a lever, a foot displaceably coupled to the carriage body, a hinge about which the lever is configured to rotate when the lever is actuated, and a cam operably attached to the hinge and configured to rotate when the lever is actuated, the cam configured to engage with the foot to displace the foot into engagement with the rail, the carriage being slidably mounted to the rail and configured to receive a second fluidic assembly,
    wherein the foot is configured to selectively engage the rail to inhibit movement of the carriage relative to the rail,
    wherein actuation of the lever is configured:
        to establish a first fluid tight seal between the first fluidic assembly and the chromatography column,
        to establish a second fluid tight seal between the second fluidic assembly and the chromatography column, and
        to displace the foot into engagement with the rail.

2. The clamp assembly of claim 1, wherein the lever is a hand-operable lever.

3. The clamp assembly of claim 1, wherein the carriage body receives the second fluidic assembly.

4. The clamp assembly of claim 1, wherein the lever is configured to establish the first fluid tight seal between the first fluidic assembly and the chromatography column received within the clamp assembly, and to establish the second fluid tight seal between the second fluidic assembly and the chromatography column such that the first and second fluid tight seals are established simultaneously.

5. The clamp assembly of claim 1, wherein the carriage body comprises one or more projections, and wherein the rail comprises a groove for receiving the one or more projections such that the carriage body is slidable along the groove.

6. The clamp assembly of claim 5, wherein the rail comprises one or more slots which allow the one or more projections of the carriage body to be inserted into the groove.

7. The clamp assembly of claim 5, wherein the rail comprises a plurality of teeth arranged along the groove, and wherein the foot is configured to engage the teeth of the rail, thereby to inhibit movement of the carriage relative to the rail.

8. The clamp assembly of claim 1, wherein the rail comprises a rail body and an end cap connected to the rail body and configured to receive the first fluidic assembly.

9. The clamp assembly of claim 1, wherein the clamp assembly accommodates chromatography columns having at least one of various column lengths and various column diameters.

10. A clamp assembly comprising:
    a rail configured to receive a first fluidic assembly; and
    a carriage including a carriage body, a lever assembly, and a foot coupled to the carriage body, the carriage being slidably mounted to the rail and configured to receive a second fluidic assembly;
    wherein the foot is configured to move between a first position, in which the foot is clear of the rail to permit movement of the carriage relative to the rail, and a second position, in which the foot engages the rail to inhibit movement of the carriage relative to the rail;
    wherein actuation of the lever assembly is configured to
        move a chromatography column received within the clamp assembly relative to the rail to create a first fluid tight seal between the chromatography column and the first fluidic assembly,
        move the second fluidic assembly relative to the carriage body to create a second fluid tight seal between the second fluidic assembly and the chromatography column, and
        move the foot from the first position to the second position.

11. The clamp assembly of claim 10, wherein the foot is biased toward the first position.

12. The clamp assembly of claim 10, wherein the carriage body includes at least one slot for receiving a portion of the lever assembly, and
    wherein the slot guides the portion of the lever assembly to move the second fluidic assembly within the carriage body.

13. A clamp assembly comprising:
    a rail configured to receive a first fluidic assembly; and
    a carriage including a carriage body, a lever, an arm coupled to the lever and the carriage body, and a foot coupled to the carriage body, the carriage being slidably mounted to the rail and configured to receive a second fluidic assembly;

wherein actuation of the lever moves the foot relative to the carriage body between a first position, in which the foot is clear of the rail, to a second position, in which the foot engages the rail and inhibits movement of the carriage relative to the rail;

wherein actuation of the lever moves a chromatography column received within the clamp assembly relative to the rail to create a first fluid tight seal between the chromatography column and the first fluidic assembly;

wherein actuation of the lever moves the second fluidic assembly relative to the carriage body to create a second fluid tight seal between the second fluidic assembly and the chromatography column.

14. The clamp assembly of claim 13, wherein the foot is biased away from the rail.

15. The clamp assembly of claim 13, wherein the carriage body includes at least one slot for receiving a portion of the arm, and wherein the slot guides the portion of the arm to advance the second fluidic assembly within the carriage body.

16. The clamp assembly of claim 1, wherein the carriage further includes:

an opening configured to receive the second fluidic assembly.

17. The clamp assembly of claim 10, wherein the lever assembly is hand-operable.

18. The clamp assembly of claim 10, wherein the carriage body receives the second fluidic assembly.

19. The clamp assembly of claim 10, wherein the lever assembly is configured to establish the first fluid tight seal between the first fluidic assembly and the chromatography column received within the clamp assembly, and to establish the second fluid tight seal between the second fluidic assembly and the chromatography column such that the first and second fluid tight seals are established simultaneously.

20. The clamp assembly of claim 10, wherein the carriage body comprises one or more projections, and wherein the rail comprises a groove for receiving the one or more projections such that the carriage body is slidable along the groove.

21. The clamp assembly of claim 20, wherein the rail comprises one or more slots which allow the one or more projections of the carriage body to be inserted into the groove.

22. The clamp assembly of claim 20, wherein the rail comprises a plurality of teeth arranged along the groove, and wherein the foot is configured to engage the teeth of the rail, thereby to inhibit movement of the carriage relative to the rail.

23. The clamp assembly of claim 10, wherein the rail comprises a rail body and an end cap connected to the rail body and configured to receive the first fluidic assembly.

24. The clamp assembly of claim 10, wherein the clamp assembly accommodates chromatography columns having at least one of various column lengths and various column diameters.

* * * * *